(12) United States Patent
Roth et al.

(10) Patent No.: US 7,605,176 B2
(45) Date of Patent: Oct. 20, 2009

(54) β-KETOAMIDE COMPOUNDS WITH MCH ANTAGONISTIC ACTIVITY

(75) Inventors: Gerald Juergen Roth, Biberach (DE); Philipp Lustenberger, Warthausen (DE); Dirk Stenkamp, Biberach (DE); Stephan Georg Mueller, Warthausen (DE); Thorsten Lehmann-Lintz, Ochsenhausen (DE); Marcus Schindler, Biberach (DE); Leo Thomas, Biberach (DE); Ralf R. H. Lotz, Schemmerhofen (DE); Marco Santagostino, Magenta (IT)

(73) Assignee: Boehringer Ingelheim International GmbH, Ingelheim (DE)

( * ) Notice: Subject to any disclaimer, the term of this patent is extended or adjusted under 35 U.S.C. 154(b) by 567 days.

(21) Appl. No.: 11/071,797

(22) Filed: Mar. 3, 2005

(65) Prior Publication Data

US 2005/0245500 A1 Nov. 3, 2005

Related U.S. Application Data

(60) Provisional application No. 60/554,229, filed on Mar. 18, 2004.

(30) Foreign Application Priority Data

Mar. 6, 2004 (DE) ...................... 10 2004 010 893

(51) Int. Cl.
  *A01N 43/36* (2006.01)
  *C07D 207/00* (2006.01)
  *C07D 295/00* (2006.01)
(52) U.S. Cl. ...................... 514/408; 548/400
(58) Field of Classification Search .................. None
  See application file for complete search history.

(56) References Cited

U.S. PATENT DOCUMENTS

| | | | |
|---|---|---|---|
| 2004/0063686 A1 | 4/2004 | Johnson et al. | |
| 2004/0077628 A1 | 4/2004 | Ishihara et al. | |
| 2005/0059651 A1 | 3/2005 | Armstrong et al. | |

FOREIGN PATENT DOCUMENTS

| | | |
|---|---|---|
| EP | 1 283 199 A1 | 2/2003 |
| EP | 1 285 651 A1 | 2/2003 |
| EP | 1 539 667 A1 | 11/2005 |
| WO | WO 98/38156 | 9/1998 |
| WO | WO 01/21577 A2 | 3/2001 |
| WO | WO 02/10146 A1 | 2/2002 |
| WO | WO 03/033476 A1 | 4/2003 |
| WO | WO 2004/024702 A1 | 3/2004 |
| WO | WO 2004/039764 A1 | 5/2005 |
| WO | WO 2005/063239 A1 | 7/2005 |

OTHER PUBLICATIONS

Hervieu, G. Expert Opinion in Therapeutic Targets, 2003, 7(4), 495-511.*
Crow, S. Expert Opinion in Investigational Drugs, 1997, 6(4), 427-36.*
Pennini, R. et al; "Condensation of n-alkyl-o-phenylenediamine With Ethyl Benzoylacetate", Farmaco, Edizione, Scientifica, Bd. 31 ,Nr. 2, 1976, pp. 120-125, XP002334423.

* cited by examiner

*Primary Examiner*—James O Wilson
*Assistant Examiner*—Noble Jarrell
(74) *Attorney, Agent, or Firm*—Michael P. Morris; Mary-Ellen M. Devlin; Timothy X. Wltkowski

(57) ABSTRACT

Compounds of formula I

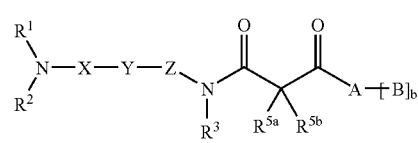

wherein the groups and residues A, B, b, X, Y, Z, $R^1$, $R^2$, $R^3$, $R^{5a}$ and $R^{5b}$ have the meanings given in claim 1. The invention further relates to pharmaceutical compositions containing at least one amide according to the invention. As a result of their MCH-receptor antagonistic activity the pharmaceutical compositions according to the invention are suitable for the treatment of metabolic disorders and/or eating disorders, particularly obesity, bulimia, anorexia, hyperphagia, and diabetes.

18 Claims, No Drawings

β-KETOAMIDE COMPOUNDS WITH MCH ANTAGONISTIC ACTIVITY

RELATED APPLICATIONS

This application claims benefit of U.S. Provisional Application 60/554,229, filed Mar. 18, 2004, and priority to German patent application DE 10 2004 010 893.5, filed Mar. 6, 2004, each of which is incorporated herein by reference in its entirety.

FIELD OF THE INVENTION

The present invention relates to new β-ketoamide compounds, the physiologically acceptable salts thereof as well as their use as MCH antagonists and their use in preparing a pharmaceutical preparation which is suitable for the prevention and/or treatment of symptoms and/or diseases caused by MCH or causally connected with MCH in some other way. The invention further relates to the use of a compound according to the invention for influencing eating behavior and for reducing body weight and/or for preventing an increase in the body weight of a mammal. The invention also relates to compositions and medicaments containing a compound according to the invention, and processes for preparing them. Further objects of this invention relate to processes for preparing the compounds according to the invention.

BACKGROUND OF THE INVENTION

The intake of food and its conversion in the body is an essential part of life for all living creatures. Therefore, deviations in the intake and conversion of food generally lead to problems and also illness. The changes in the lifestyle and nutrition of humans, particularly in industrialized countries, have promoted morbid excess weight (also known as corpulence or obesity) in recent decades. In affected people, obesity leads directly to restricted mobility and a reduction in the quality of life. There is the additional factor that obesity often leads to other diseases such as, for example, diabetes, dyslipidemia, high blood pressure, arteriosclerosis, and coronary heart disease. Moreover, high body weight alone puts an increased strain on the support and mobility apparatus, which can lead to chronic pain and diseases such as arthritis or osteoarthritis. Thus, obesity is a serious health problem for society.

The term obesity means an excess of adipose tissue in the body. In this connection, obesity is fundamentally to be seen as the increased level of fatness which leads to a health risk. There is no sharp distinction between normal individuals and those suffering from obesity, but the health risk accompanying obesity is presumed to rise continuously as the level of fatness increases. For simplicity's sake, in the present invention, individuals with a Body Mass Index (BMI), which is defined as the body weight measured in kilograms divided by the height (in meters) squared, above a value of 25 and more particularly above 30, are preferably regarded as suffering from obesity.

Apart from physical activity and a change in nutrition, there is currently no convincing treatment option for effectively reducing body weight. However, as obesity is a major risk factor in the development of serious and even life-threatening diseases, it is all the more important to have access to pharmaceutical active substances for the prevention and/or treatment of obesity. One approach which has been proposed very recently is the therapeutic use of MCH antagonists (cf inter alia WO 01/21577 and WO 01/82925).

Melanin-concentrating hormone (MCH) is a cyclic neuropeptide consisting of 19 amino acids. It is synthesized predominantly in the hypothalamus in mammals and from there travels to other parts of the brain by the projections of hypothalamic neurons. Its biological activity is mediated in humans through two different G-protein-coupled receptors (GPCRs) from the family of rhodopsin-related GPCRs, namely the MCH receptors 1 and 2 (MCH-1R and MCH-2R).

Investigations into the function of MCH in animal models have provided good indications for a role of the peptide in regulating the energy balance, i.e., changing metabolic activity and food intake (D. Qu, et al., *A role for melanin-concentrating hormone in the central regulation of feeding behaviour*, Nature, 1996, 380 (6571), pp. 243-7; M. Shimada, et al., *Mice lacking melanin-concentrating hormone are hypophagic and lean*, Nature, 1998, 396 (6712), pp. 670-4). For example, after intraventricular administration of MCH in rats, food intake was increased compared with control animals. Additionally, transgenic rats which produce more MCH than control animals, when given a high-fat diet, responded by gaining significantly more weight than animals without an experimentally altered MCH level. It was also found that there is a positive correlation between phases of increased desire for food and the quantity of MCH mRNA in the hypothalamus of rats. However, experiments with MCH knock-out mice are particularly important in showing the function of MCH. Loss of the neuropeptide results in lean animals with a reduced fat mass, which take in significantly less food than control animals.

The anorectic effects of MCH are presumably mediated in rodents through the $G_{\alpha s}$-coupled MCH-1R (B. Borowsky, et al., *Antidepressant, anxiolytic and anorectic effects of a melanin-concentrating hormone-1 receptor antagonist*, Nat Med, 2002, 8 (8), pp. 825-30; Y. Chen, et al., *Targeted disruption of the melanin-concentrating hormone receptor-1 results in hyperphagia and resistance to diet-induced obesity*, Endocrinology, 2002, 143 (7), pp. 2469-77; D. J. Marsh, et al., *Melanin-concentrating hormone 1 receptor-deficient mice are lean, hyperactive, and hyperphagic and have altered metabolism*, Proc Natl Acad Sci USA, 2002. 99 (5), pp. 3240-5; S. Takekawa, et al., T-226296: *a novel, orally active and selective melanin-concentrating hormone receptor antagonist*, Eur J Pharmacol, 2002, 438 (3), pp. 129-35), as, unlike primates, ferrets and dogs, no second MCH receptor subtype has hitherto been found in rodents. Loss of the MCH-1R in knock-out mice leads to a lower fat mass, an increased energy conversion and, when fed on a high fat diet, no increase in weight, compared with control animals. Another indication of the importance of the MCH system in regulating the energy balance results from experiments with a receptor antagonist (SNAP-7941) (B. Borowsky, et al., Nat Med, 2002, 8 (8), pp. 825-30). In long term trials the animals treated with the antagonist lose significant amounts of weight.

In addition to its anorectic effect, the MCH-1R antagonist SNAP-7941 also achieves additional anxiolytic and antidepressant effects in behavioral experiments on rats (B. Borowsky, et al., Nat Med, 2002, 8 (8), pp. 825-30). Thus, there are clear indications that the MCH-MCH-1R system is involved not only in regulating the energy balance but also in affectivity.

In the patent literature certain amine compounds are proposed as MCH antagonists. Thus, WO 01/21577 (Takeda) describes compounds of formula

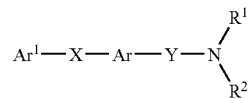

wherein $Ar^1$ denotes a cyclic group, X denotes a spacer, Y denotes a bond or a spacer, Ar denotes an aromatic ring which may be fused with a non-aromatic ring, $R^1$ and $R^2$ independently of one another denote H or a hydrocarbon group, while $R^1$ and $R^2$ together with the adjacent N atom may form an N-containing hetero ring and $R^2$ with Ar may also form a spirocyclic ring, R together with the adjacent N atom and Y may form an N-containing hetero ring, as MCH antagonists for the treatment of obesity, inter alia.

Moreover WO 01/82925 (Takeda) also describes compounds of formula

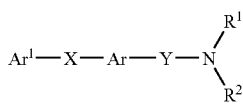

wherein $Ar^1$ denotes a cyclic group, X and Y represent spacer groups, Ar denotes an optionally substituted fused polycyclic aromatic ring, $R^1$ and $R^2$ independently of one another represent H or a hydrocarbon group, while $R^1$ and $R^2$ together with the adjacent N atom may form an N-containing heterocyclic ring and $R^2$ together with the adjacent N atom and Y may form an N-containing hetero ring, as MCH antagonists for the treatment of obesity.

The aim of the present invention is to provide new β-ketoamide compounds, particularly those which are effective as MCH antagonists.

The invention also sets out to provide new β-ketoamide compounds which can be used to influence the eating habits of mammals and achieve a reduction in body weight, particularly in mammals, and/or prevent an increase in body weight.

The present invention further sets out to provide new pharmaceutical compositions which are suitable for the prevention and/or treatment of symptoms and/or diseases caused by MCH or otherwise causally connected to MCH. In particular, the aim of this invention is to provide pharmaceutical compositions for the treatment of metabolic disorders such as obesity and/or diabetes as well as diseases and/or disorders which are associated with obesity and diabetes. Other objectives of the present invention are concerned with demonstrating advantageous uses of the compounds according to the invention. The invention also sets out to provide a process for preparing the amide compounds according to the invention. Other aims of the present invention will be immediately apparent to the skilled man from the foregoing remarks and those that follow.

SUMMARY OF THE INVENTION

The invention relates firstly to β-ketoamide compounds of general formula I

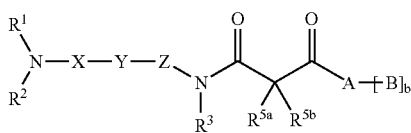

wherein:

$R^1$ and $R^2$ independently of one another denote H, a $C_{1-8}$-alkyl, or $C_{3-7}$-cycloalkyl group optionally mono- or polysubstituted by the group $R^{11}$, while a —$CH_2$— group in position 3 or 4 of a 5-, 6-, or 7-membered cycloalkyl group may be replaced by —O—, —S—, or —$NR^{13}$—, or a phenyl or pyridinyl group optionally mono- or polysubstituted by the group $R^{20}$ and/or monosubstituted by nitro, or $R^1$ and $R^2$ form a $C_{2-8}$-alkylene bridge, wherein one or two —$CH_2$— groups independently of one another may be replaced by —CH=N— or —CH=CH— and/or one or two —$CH_2$— groups independently of one another may be replaced by —O—, —S—, —SO—, —$(SO_2)$—, —C(=$CH_2$)—, or —$NR^{13}$— in such a way that heteroatoms are not directly joined together, and that a group —CO— is not directly linked to the group $R^1R^2N$—, while in the alkylene bridge defined hereinbefore one or more H atoms may be replaced by $R^{14}$, and the alkylene bridge defined hereinbefore may be substituted by one or two identical or different carbo- or heterocyclic groups Cy such that the bond between the alkylene bridge and the group Cy is made via a single or double bond, via a common C atom forming a spirocyclic ring system, via two common adjacent C and/or N atoms forming a fused bicyclic ring system or via three or more C and/or N atoms forming a bridged ring system;

$R^3$ denotes H, $C_{1-6}$-alkyl, $C_{3-7}$-cycloalkyl, $C_{3-7}$-cycloalkyl-$C_{1-4}$-alkyl, or phenyl-$C_{1-3}$-alkyl;

X denotes a $C_{1-8}$-alkylene bridge, wherein a —$CH_2$— group which is not directly linked to the group $R^1R^2N$— may be replaced by —CH=CH— or —C≡C— and/or one or two non-adjacent —$CH_2$— groups, which are not directly linked to the group $R^1R^2N$—, may be replaced independently of one another by —O—, —S—, —(SO)—, —$(SO_2)$—, —CO—, or —$NR^4$— in such a way that in each case two O, S, or N atoms or an O and an S atom are not directly joined together, while the bridge X may be connected to $R^1$ including the N atom linked to $R^1$ and X, forming a heterocyclic group, while the bridge X may additionally also be connected to $R^2$ including the N atom connected to $R^2$ and X, forming a heterocyclic group, and while two C atoms or a C and an N atom of the alkylene bridge may be joined together by an additional $C_{1-4}$-alkylene bridge, and a C atom not directly connected to a heteroatom may be substituted by $R^{10}$ and/or one or two C atoms may be substituted in each case by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl, and $C_{4-7}$-cycloalkenyl-$C_{1-3}$-alkyl, while two alkyl and/or alkenyl substituents may be joined together, forming a carbocyclic ring system;

Z denotes a single bond or —$CR^{7a}R^{7b}$—$CR^{7c}R^{7d}$—;

Y has one of the meanings given for Cy, while $R^1$ may be connected to Y including the group X and the N atom connected to $R^1$ and X, forming a heterocyclic group fused to Y, and/or X may be connected to Y forming a carbo- or heterocyclic group fused to Y;

A has one of the meanings given for Cy;

B has one of the meanings given for Cy;

b has the value 0 or 1;

Cy denotes a carbo- or heterocyclic group selected from one of the following meanings:

a saturated 3- to 7-membered carbocyclic group, an unsaturated 4- to 7-membered carbocyclic group, a phenyl group, a saturated 4- to 7-membered or unsaturated 5- to 7-membered heterocyclic group with an N, O, or S atom as heteroatom, a saturated or unsaturated 5- to 7-membered heterocyclic group with two or more N atoms or with one or two N atoms and one O or S atom as heteroatoms, an aromatic heterocyclic 5- or 6-membered group with one or more identical or different heteroatoms selected from N, O, and/or S, while the abovementioned 4-, 5-, 6-, or 7-membered groups may be fused to a phenyl or pyridine ring via two common adjacent C atoms, and in the abovementioned 5-, 6-, or 7-membered groups one or two non-adjacent —CH$_2$ groups may be replaced independently of one another by a —CO—, —C(=CH$_2$)—, —(SO)—, or —(SO$_2$)— group, and the abovementioned saturated 6- or 7-membered groups may also be present as bridged ring systems with an imino, N—(C$_{1-4}$-alkyl)-imino, methylene, C$_{1-4}$-alkyl-methylene, or di-(C$_{1-4}$-alkyl)-methylene bridge, and the abovementioned cyclic groups may be mono- or polysubstituted by R$^{20}$ at one or more C atoms, in the case of a phenyl group may also additionally be monosubstituted by nitro, and/or one or more NH groups may be substituted by R$^{21}$;

R$^4$ has one of the meanings given for R$^{17}$ or denotes C$_{3-6}$-alkenyl or C$_{3-6}$-alkynyl, R$^{5a}$ and R$^{5b}$ independently of one another denote H, C$_{1-3}$-alkyl, C$_{3-7}$-cycloalkyl, C$_{3-7}$-cycloalkyl-C$_{1-3}$-alkyl, CF$_3$, F, or Cl, while R$^{5a}$ and R$^{5b}$ representing alkyl may be joined together such that a C$_{3-7}$-cycloalkyl group is formed together with the C atom to which R$^{5a}$ and R$^{5b}$ are linked, R$^{7a}$ and R$^{7c}$ independently of one another denote H, F, Cl, C$_{1-4}$-alkyl, or CF$_3$, R$^{7b}$ and R$^{7d}$ independently of one another denote H, F, C$_{1-4}$-alkyl, C$_{3-7}$-cycloalkyl, C$_{3-7}$-cycloalkyl-C$_{1-3}$-alkyl, or CF$_3$, while R$^{7a}$ and R$^{7b}$ representing alkyl may be joined together such that a C$_{3-7}$-cycloalkyl group is formed together with the C atom to which R$^{7a}$ and R$^{7b}$ are linked, and/or R$^{7c}$ and R$^{7d}$ representing alkyl may be joined together such that a C$_{3-7}$-cycloalkyl group is formed together with the C atom to which R$^{7c}$ and R$^{7d}$ are linked, or R$^{7b}$ and R$^{7d}$ representing alkyl may be joined together such that a C$_{3-7}$-cycloalkyl group is formed together with the two C atoms to which R$^{7b}$ and R$^{7d}$ are linked;

R$^{10}$ denotes hydroxy, hydroxy-C$_{1-3}$-alkyl, C$_{1-4}$-alkoxy, (C$_{1-4}$-alkoxy)-C$_{1-3}$-alkyl, carboxy, C$_{1-4}$-alkoxycarbonyl, amino, C$_{1-4}$-alkyl-amino, di-(C$_{1-4}$-alkyl)-amino, cyclo-C$_{3-6}$-alkyleneimino, amino-C$_{1-3}$-alkyl, C$_{1-4}$-alkyl-amino-C$_{1-3}$-alkyl, di-(C$_{1-4}$-alkyl)-amino-C$_{1-3}$-alkyl, cyclo-C$_{3-6}$-alkyleneimino-C$_{1-3}$-alkyl, amino-C$_{1-3}$-alkoxy, C$_{1-4}$-alkyl-amino-C$_{1-3}$-alkoxy, di-(C$_{1-4}$-alkyl)-amino-C$_{1-3}$-alkoxy, cyclo-C$_{3-6}$-alkyleneimino-C$_{1-3}$-alkoxy, aminocarbonyl, C$_{1-4}$-alkyl-aminocarbonyl, di-(C$_{1-4}$-alkyl)-aminocarbonyl, or cyclo-C$_{3-6}$-alkyleneimino-carbonyl;

R$^{11}$ denotes C$_{1-3}$-alkyl, C$_{2-6}$-alkenyl, C$_{2-6}$-alkynyl, R$^{15}$—O—, R$^{15}$—O—C$_{1-3}$-alkyl-, R$^{15}$—O—CO—, R$^{15}$—CO—O—, cyano, R$^{16}$R$^{17}$N—, R$^{18}$R$^{19}$N—CO—, or Cy;

R$^{13}$ has one of the meanings given for R$^{17}$;

R$^{14}$ denotes halogen, C$_{1-6}$-alkyl, C$_{2-6}$-alkenyl, C$_{2-6}$-alkynyl, R$^{15}$—O—, R$^{15}$—O—CO—, R$^{15}$—CO, R$^{15}$—CO—O—, R$^{16}$R$^{17}$N—, R$^{18}$R$^{19}$N—CO—, R$^{15}$—O—C$_{1-3}$-alkyl, R$^{15}$—O—CO—C$_{1-3}$-alkyl, R$^{15}$—O—CO—NH—, R$^{15}$—SO$_2$—NH, R$^{15}$—O—CO—NH—C$_{1-3}$-alkyl, R$^{15}$—SO$_2$—NH—C$_{1-3}$-alkyl, R$^{15}$—CO—C$_{1-3}$-alkyl, R$^{15}$—CO—O—C$_{1-3}$-alkyl, R$^{16}$R$^{17}$N—C$_{1-3}$-alkyl, R$^{18}$R$^{19}$N—CO—C$_{1-3}$-alkyl, or Cy—C$_{1-3}$-alkyl-;

R$^{15}$ denotes H, C$_{1-4}$-alkyl, C$_{3-7}$-cycloalkyl, C$_{3-7}$-cycloalkyl-C$_{1-3}$-alkyl, phenyl, phenyl-C$_{1-3}$-alkyl, pyridinyl, or pyridinyl-C$_{1-3}$-alkyl;

R$^{16}$ denotes H, C$_{1-6}$-alkyl, C$_{3-7}$-cycloalkyl, C$_{3-7}$-cycloalkyl-C$_{1-3}$-alkyl, C$_{4-7}$-cycloalkenyl, C$_{4-7}$-cycloalkenyl-C$_{1-3}$-alkyl, hydroxy-C$_{2-3}$-alkyl, C$_{1-4}$-alkoxy-C$_{2-3}$-alkyl, amino-C$_{2-6}$-alkyl, C$_{1-4}$-alkyl-amino-C$_{2-6}$-alkyl, di-(C$_{1-4}$-alkyl)-amino-C$_{2-6}$-alkyl, or cyclo-C$_{3-6}$-alkyleneimino-C$_{2-6}$-alkyl;

R$^{17}$ has one of the meanings given for R$^{16}$ or denotes phenyl, phenyl-C$_{1-3}$-alkyl, pyridinyl, dioxolan-2-yl, C$_{1-4}$-alkylcarbonyl, hydroxy-carbonyl-C$_{1-3}$-alkyl, C$_{1-4}$-alkoxycarbonyl, C$_{1-4}$-alkoxycarbonyl-C$_{1-3}$-alkyl, C$_{1-4}$-alkylcarbonylamino-C$_{2-3}$-alkyl, N—(C$_{1-4}$-alkylcarbonyl)-N—(C$_{1-4}$-alkyl)-amino-C$_{2-3}$-alkyl, C$_{1-4}$-alkylsulfonyl, C$_{1-4}$-alkylsulfonylamino-C$_{2-3}$-alkyl, or N—(C$_{1-4}$-alkylsulfonyl)-N—(C$_{1-4}$-alkyl)-amino-C$_{2-3}$-alkyl-, R$^{18}$ and R$^{19}$ independently of one another denote H or C$_{1-6}$-alkyl;

R$^{20}$ denotes halogen, hydroxy, cyano, C$_{1-6}$-alkyl, C$_{2-6}$-alkenyl, C$_{2-6}$-alkynyl, C$_{3-7}$-cycloalkyl, C$_{3-7}$-cycloalkyl-C$_{1-3}$-alkyl, hydroxy-C$_{1-4}$-alkyl, R$^{22}$—C$_{1-3}$-alkyl, or has one of the meanings given for R$^{22}$;

R$^{21}$ denotes C$_{1-4}$-alkyl, hydroxy-C$_{2-3}$-alkyl, C$_{1-4}$-alkoxy-C$_{2-6}$-alkyl, C$_{1-4}$-alkyl-amino-C$_{2-6}$-alkyl, di-(C$_{1-4}$-alkyl)-amino-C$_{2-6}$-alkyl, cyclo-C$_{3-6}$-alkyleneimino-C$_{2-6}$-alkyl, phenyl-C$_{1-3}$-alkyl, C$_{1-4}$-alkyl-carbonyl, C$_{1-4}$-alkoxy-carbonyl, or C$_{1-4}$-alkylsulfonyl; and R$^{22}$ denotes phenyl-C$_{1-3}$-alkoxy, cyclo-C$_{3-6}$-alkyleneimino-C$_{2-4}$-alkoxy, C$_{1-4}$-alkoxy, C$_{1-4}$-alkylthio, carboxy, C$_{1-4}$-alkylcarbonyl, C$_{1-4}$-alkoxycarbonyl, aminocarbonyl, C$_{1-4}$-alkylaminocarbonyl, di-(C$_{1-4}$-alkyl)-aminocarbonyl, cyclo-C$_{3-6}$-alkyl-amino-carbonyl, cyclo-C$_{3-6}$-alkyleneimino-carbonyl, cyclo-C$_{3-6}$-alkyleneimino-C$_{2-4}$-alkyl-aminocarbonyl, phenylaminocarbonyl, C$_{1-4}$-alkyl-sulfonyl, C$_{1-4}$-alkyl-sulfinyl, C$_{1-4}$-alkyl-sulfonylamino, amino, C$_{1-4}$-alkylamino, di-(C$_{1-4}$-alkyl)-amino, C$_{1-4}$-alkyl-carbonyl-amino, cyclo-C$_{3-6}$-alkyleneimino, phenyl-C$_{1-3}$-alkylamino, N—(C$_{1-4}$-alkyl)-phenyl-C$_{1-3}$-alkylamino, acetylamino, propionylamino, phenylcarbonylamino, phenylcarbonylmethylamino, hydroxy-C$_{1-3}$-alkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, aminocarbonyl-amino, or C$_{1-4}$-alkylaminocarbonyl-amino, while in the abovementioned groups and radicals, particularly in X, R$^1$ to R$^4$, R$^{10}$, R$^{11}$, and R$^{13}$ to R$^{22}$, in each case one or more C atoms may additionally be mono- or polysubstituted by F and/or in each case one or two C atoms independently of one another may additionally be monosubstituted by Cl or Br and/or in each case one or more phenyl rings may independently of one another additionally comprise one, two, or three substituents selected from the group F, Cl, Br, I, C$_{1-4}$-alkyl, C$_{1-4}$-alkoxy, difluoromethyl, trifluoromethyl, hydroxy, amino, C$_{1-3}$-alkylamino, di-(C$_{1-3}$-alkyl)-amino, acetylamino, aminocarbonyl, cyano, difluoromethoxy, trifluoromethoxy, amino-C$_{1-3}$-alkyl, C$_{1-3}$-alkylamino-C$_{1-3}$-alkyl, and di-(C$_{1-3}$-alkyl)-amino-C$_{1-3}$-alkyl and/or may be monosubstituted by nitro, and the H atom of a carboxy group present or an H atom bound to an N atom in each case may be replaced by a group which can be cleaved in vivo, the tautomers, the diastereomers, the enantiomers, the mixtures thereof, and the salts thereof.

The compounds according to the present invention, including the physiologically acceptable salts, are especially effective as antagonists of the MCH receptor, particularly the MCH-1 receptor, and exhibit very good affinity in MCH receptor binding studies. In addition, the compounds according to the invention have a high to very high selectivity with regard to the MCH receptor. Generally the compounds according to the invention have low toxicity, they are well absorbed by oral route and have good intracerebral transitivity, particularly brain accessibility.

The invention also relates to the compounds in the form of the individual optical isomers, mixtures of the individual diastereomers, enantiomers, or racemates, in the form of the tautomers and in the form of the free bases or the corresponding acid addition salts with pharmacologically safe acids. The subject of the invention also includes the compounds according to the invention, including their salts, wherein one or more hydrogen atoms are replaced by deuterium.

This invention also includes the physiologically acceptable salts of the β-ketoamide compounds according to the invention as described above and hereinafter.

Also covered by this invention are compositions containing at least one β-ketoamide compound according to the invention and/or a salt according to the invention optionally together with one or more physiologically acceptable excipients.

Also covered by this invention are pharmaceutical compositions containing at least one β-ketoamide compound according to the invention and/or a salt according to the invention optionally together with one or more inert carriers and/or diluents.

The invention also relates to the use of at least one β-ketoamide compound according to the invention and/or a salt according to the invention for influencing the eating behavior of a mammal.

The invention also relates to the use of at least one β-ketoamide compound according to the invention and/or a salt according to the invention for reducing the body weight and/or for preventing an increase in the body weight of a mammal.

The invention also relates to the use of at least one β-ketoamide compound according to the invention and/or a salt according to the invention for preparing a pharmaceutical composition with an MCH-receptor-antagonistic activity, particularly with an MCH-1-receptor-antagonistic activity.

Moreover, the invention relates to the use of at least one β-ketoamide compound according to the invention and/or a salt according to the invention for preparing a pharmaceutical composition which is suitable for the prevention and/or treatment of symptoms and/or diseases which are caused by MCH or are otherwise causally connected with MCH.

The invention also relates to the use of at least one β-ketoamide compound according to the invention and/or a salt according to the invention for preparing a pharmaceutical composition which is suitable for the prevention and/or treatment of metabolic disorders and/or eating disorders, particularly obesity, bulimia, bulimia nervosa, cachexia, anorexia, anorexia nervosa, and hyperphagia.

This invention also relates to the use of at least one β-ketoamide compound according to the invention and/or a salt according to the invention for preparing a pharmaceutical composition which is suitable for the prevention and/or treatment of diseases and/or disorders associated with obesity, particularly diabetes, especially type II diabetes, complications of diabetes including diabetic retinopathy, diabetic neuropathy, diabetic nephropathy, insulin resistance, pathological glucose tolerance, encephalorrhagia, cardiac insufficiency, cardiovascular diseases, particularly arteriosclerosis and high blood pressure, arthritis, and gonitis.

Moreover, the invention relates to the use of at least one β-ketoamide compound according to the invention and/or a salt according to the invention for preparing a pharmaceutical composition which is suitable for the prevention and/or treatment of hyperlipidemia, cellulitis, fat accumulation, malignant mastocytosis, systemic mastocytosis, emotional disorders, affective disorders, depression, anxiety, sleep disorders, reproductive disorders, sexual disorders, memory disorders, epilepsy, forms of dementia, and hormonal disorders.

Another object of the invention is the use of at least one β-ketoamide compound according to the invention and/or a salt according to the invention for preparing a pharmaceutical composition which is suitable for the prevention and/or treatment of micturition disorders, such as, for example, urinary incontinence, hyperactive urinary bladder, urgency, nycturia, and enuresis.

The invention further relates to the use of at least one β-ketoamide compound according to the invention and/or a salt according to the invention for preparing a pharmaceutical composition which is suitable for the prevention and/or treatment of dependencies and/or withdrawal symptoms.

Furthermore the invention relates to processes for preparing a pharmaceutical composition according to the invention, characterized in that at least one β-ketoamide compound according to the invention and/or a salt according to the invention is incorporated in one or more inert carriers and/or diluents by a non-chemical method.

The invention further relates to a pharmaceutical composition containing a first active substance selected from the β-ketoamide compounds according to the invention and/or the corresponding salts and a second active substance selected from the group consisting of active substances for the treatment of diabetes, active substances for the treatment of diabetic complications, active substances for the treatment of obesity, preferably other than MCH antagonists, active substances for the treatment of high blood pressure, active substances for the treatment of dyslipidemia or hyperlipidemia, including arteriosclerosis, active substances for the treatment of arthritis, active substances for the treatment of anxiety states, and active substances for the treatment of depression, optionally together with one or more inert carriers and/or diluents.

The invention also relates to a process for preparing β-ketoamide compounds of formula I

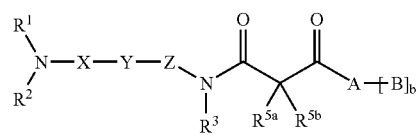

wherein A, B, b, X, Y, Z, $R^1$, $R^2$, $R^3$, $R^{5a}$, and $R^{5b}$ have the meanings given hereinbefore and hereinafter, wherein an amine compound of formula A1

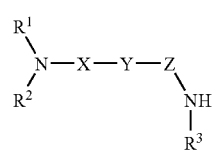

where X, Y, Z, $R^1$, $R^2$, and $R^3$ have the meanings given hereinbefore and hereinafter, is reacted with a carboxylic acid compound or a carboxylic acid derivative of formula A2

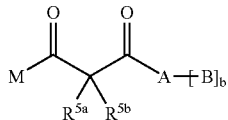

where A, B, b, $R^{5a}$, and $R^{5b}$ are as hereinbefore defined, and the group M denotes OH, Cl, $C_{1-6}$-alkoxy, $C_{1-6}$-alkylthio, or $C_{1-6}$-alkyl-COO—, in the presence of at least one base, in a solvent or mixture of solvents.

This invention further relates to a process for preparing β-ketoamide compounds of formula I

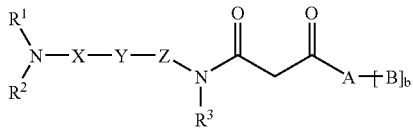

where A, B, b, X, Y, Z, $R^1$, $R^2$, and $R^3$ have the meanings given hereinbefore and hereinafter, wherein a propynoic acid amide compound of formula B1

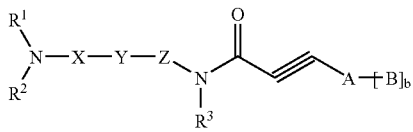

where A, B, b, X, Y, Z, $R^1$, $R^2$, and $R^3$ are as hereinbefore defined, is hydrolyzed by the addition of an acid or base in a solvent or mixture of solvents and optionally in the presence of an activating nucleophile.

The starting materials and intermediate products used in the synthesis according to the invention, particularly the compounds of formula A1, A2, and B1, are also a subject of this invention.

DETAILED DESCRIPTION OF THE INVENTION

Unless otherwise specified, the groups, residues and substituents, particularly A, B, X, Y, Z, $R^1$ to $R^4$, $R^{5a}$, $R^{5b}$, $R^{7a}$, $R^{7b}$, $R^{7c}$, $R^{7d}$, $R^{10}$, $R^{11}$, $R^{13}$ to $R^{22}$, and the index b have the meanings given hereinbefore.

If groups, residues and/or substituents occur more than once in a compound, they may have the same or different meanings in each case.

According to the invention the tautomers of the compounds of formula I, particularly the enol tautomers of the keto form represented by formula I, are also included.

In the event that $R^{5b}$ denotes a H atom, the following compounds are included according to the invention, while formula I (keto) indicates the keto form and formula I (enol) indicates the associated enol form:

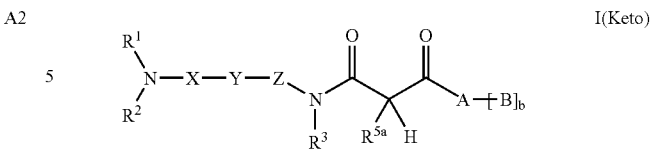

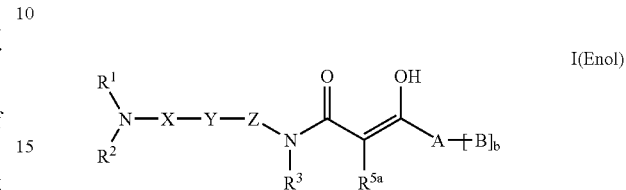

In the embodiments and Examples described hereinafter, only the keto form is explicitly mentioned; the corresponding enol form which is readily obtainable by anyone skilled in the art is also included in every case, according to the invention.

Particularly preferred definitions of the groups $R^{5a}$, $R^{5b}$ are in each case independently of one another H, F, Cl, $CF_3$, methyl, and ethyl, particularly H, F, methyl, and ethyl, particularly preferably H, F, and methyl. According to another preferred embodiment $R^{5a}$ and $R^{5b}$ representing methyl are joined together in such a way that a cyclopropyl group is formed together with the C atom to which $R^{5a}$ and $R^{5b}$ are linked.

Most particularly preferably $R^{5a}$ and $R^{5b}$ denote H.

Preferred meanings of the substituent $R^3$ are H, $C_{1-4}$-alkyl, $C_{3-6}$-cycloalkyl, or $C_{3-6}$-cycloalkyl-$C_{1-3}$-alkyl; particularly H or $C_{1-3}$-alkyl. Particularly preferably $R^3$ denotes H or methyl, particularly H.

The substituents $R^1$ and $R^2$ may have the meanings given above and hereinafter as separate groups or may be connected to one another as a bridge. For simplicity's sake, the preferred meanings of $R^1$ and $R^2$ as separate groups will be described first of all and then the preferred meanings of the groups $R^1$ and $R^2$ connected to one another to form a bridge will be given. Preferred compounds according to the invention therefore have one of the preferred meanings of $R^1$ and $R^2$, described below, as separate groups, combined with one of the preferred meanings of $R^1$ and $R^2$, described hereinafter, as groups connected to one another to form a bridge.

If $R^1$ and $R^2$ are not joined together via an alkylene bridge, $R^1$ and $R^2$ independently of one another preferably denote a $C_{1-8}$-alkyl or $C_{3-7}$-cycloalkyl group optionally mono- or polysubstituted by the group $R^{11}$, while a —$CH_2$— group in position 3 or 4 of a 5-, 6-, or 7-membered cycloalkyl group may be replaced by —O—, —S—, or —$NR^{13}$—, or a phenyl or pyridinyl group optionally mono- or polysubstituted by the group $R^{20}$ and/or monosubstituted by nitro, while one of the groups $R^1$ and $R^2$ may also represent H.

In the groups $R^1$ and $R^2$ one or more C atoms may be mono- or polysubstituted by F and/or one or two C atoms independently of one another may be monosubstituted by Cl, Br, or CN.

Preferred meanings of the group $R^{11}$ are $C_{1-3}$-alkyl, $C_{2-6}$-alkenyl, $C_{2-6}$-alkynyl, $R^{15}$—O—, cyano, $R^{16}R^{17}N$—, $C_{3-7}$-cycloalkyl, cyclo-$C_{3-6}$-alkyleneimino, pyrrolidinyl, —N—($C_{1-4}$-alkyl)-pyrrolidinyl, piperidinyl, N—($C_{1-4}$-alkyl)-piperidinyl, phenyl, and pyridyl, while in the abovementioned groups and residues one or more C atoms may be mono- or polysubstituted by F and/or one or two C atoms independently of one another may be monosubstituted by Cl, Br, or CN, and the abovementioned cyclic groups may be mono- or polysubstituted by $R^{20}$ at one or more C atoms, in the case of a phenyl group may also additionally be monosubstituted by nitro, and/or one or more NH groups may be substituted by $R^{21}$. If $R^{11}$ has one of the meanings $R^{15}$—O—, cyano, $R^{16}R^{17}N$— or cyclo-$C_{3-6}$-alkyleneimino, the C atom of the alkyl or cycloalkyl group substituted by $R^{11}$ is preferably not directly connected to a heteroatom, such as, for example, the group —N—X.

Preferably the groups $R^1$ and $R^2$ independently of one another denote H, $C_{1-6}$-alkyl, $C_{3-5}$-alkenyl, $C_{3-5}$-alkynyl, $C_{3-7}$-cycloalkyl, hydroxy-$C_{3-7}$-cycloalkyl, $C_{3-7}$-cycloalkyl-$C_{1-3}$-alkyl, (hydroxy-$C_{3-7}$-cycloalkyl)-$C_{1-3}$-alkyl, hydroxy-$C_{2-4}$-alkyl, NC—$C_{2-3}$-alkyl, $C_{1-4}$-alkoxy-$C_{2-4}$-alkyl, hydroxy-$C_{1-4}$-alkoxy-$C_{2-4}$-alkyl, $C_{1-4}$-alkoxy-carbonyl-$C_{1-4}$-alkyl, carboxyl-$C_{1-4}$-alkyl, amino-$C_{2-4}$-alkyl, $C_{1-4}$-alkyl-amino-$C_{2-4}$-alkyl, di-($C_{1-4}$-alkyl)-amino-$C_{2-4}$-alkyl, cyclo-$C_{3-6}$-alkyleneimino-$C_{2-4}$-alkyl, pyrrolidin-3-yl, N—($C_{1-4}$-alkyl)-pyrrolidinyl, pyrrolidinyl-$C_{1-3}$-alkyl, N—($C_{1-4}$-alkyl)-pyrrolidinyl-$C_{1-3}$-alkyl, piperidin-3-yl, or -4-yl, N—($C_{1-4}$-alkyl)-piperidin-3-yl, or -4-yl, piperidinyl-$C_{1-3}$-alkyl, N—($C_{1-4}$-alkyl)-piperidinyl-$C_{1-3}$-alkyl, tetrahydropyran-3-yl, tetrahydropyran-4-yl, tetrahydropyranyl-$C_{1-3}$-alkyl, tetrahydrofuran-3-yl, tetrahydrofuranyl-$C_{1-3}$-alkyl, phenyl, phenyl-$C_{1-3}$-alkyl, pyridyl, or pyridyl-$C_{1-3}$-alkyl, while in the abovementioned groups and residues one or more C atoms may be mono- or polysubstituted by F and/or one or two C atoms, particularly one C atom, may be monosubstituted independently of one another with Cl or Br, and the phenyl or pyridyl group may be mono- or polysubstituted by the group $R^{20}$ and/or monosubstituted by nitro. Preferably the abovementioned cycloalkyl rings may be mono- or polysubstituted by substituents selected from hydroxy, hydroxy-$C_{1-3}$-alkyl, $C_{1-3}$-alkyl, or $C_{1-3}$-alkyloxy, particularly hydroxy, hydroxymethyl, methyl, and methoxy. Preferably also, the $C_{2-4}$-alkyl bridges in the definitions hydroxy-$C_{2-4}$-alkyl and $C_{1-4}$-alkoxy-$C_{2-4}$-alkyl may additionally be monosubstituted by hydroxy, hydroxy-$C_{1-3}$-alkyl, $C_{1-3}$-alkyl, or $C_{1-3}$-alkyloxy, particularly hydroxy, hydroxymethyl, methyl, or methoxy. Preferred substituents of the abovementioned phenyl or pyridyl groups are selected from among F, Cl, Br, I, cyano, $C_{1-4}$-alkyl, $C_{1-4}$-alkoxy, difluoromethyl, trifluoromethyl, hydroxy, amino, $C_{1-3}$-alkylamino, di-($C_{1-3}$-alkyl)-amino, acetylamino, aminocarbonyl, difluoromethoxy, trifluoromethoxy, amino-$C_{1-3}$-alkyl, $C_{1-3}$-alkylamino-$C_{1-3}$-alkyl, and di-($C_{1-3}$-alkyl)-amino-$C_{1-3}$-alkyl, while a phenyl group may also be monosubstituted by nitro.

Particularly preferred definitions of the groups $R^1$ and/or $R^2$ are selected from among H, $C_{1-6}$-alkyl, $C_{3-7}$-cycloalkyl, $C_{3-7}$-cycloalkyl-$C_{1-3}$-alkyl, tetrahydropyran-3, or -4-yl, tetrahydropyranyl-$C_{1-3}$-alkyl, piperidin-3-yl or -4-yl, N—($C_{1-4}$-alkyl)-piperidin-3-yl or -4-yl, piperidinyl-$C_{1-3}$-alkyl, N—($C_{1-4}$-alkyl)-piperidinyl-$C_{1-3}$-alkyl, phenyl, pyridyl, phenyl-$C_{1-3}$-alkyl, pyridyl-$C_{1-3}$-alkyl, hydroxy-$C_{2-4}$-alkyl, $C_{1-4}$-alkoxy-$C_{2-4}$-alkyl, amino-$C_{2-4}$-alkyl, $C_{1-4}$-alkyl-amino-$C_{2-4}$-alkyl, and di-($C_{1-4}$-alkyl)-amino-$C_{2-4}$-alkyl, while cycloalkyl rings may be mono-, di-, or trisubstituted by substituents selected from hydroxy, hydroxy-$C_{1-3}$-alkyl, $C_{1-3}$-alkyl, or $C_{1-3}$-alkyloxy, particularly hydroxy, hydroxymethyl, methyl, and methoxy, and $C_{2-4}$-alkyl bridges in the definitions hydroxy-$C_{2-4}$-alkyl and $C_{1-4}$-alkoxy-$C_{2-4}$-alkyl may additionally be monosubstituted by hydroxy, hydroxy-$C_{1-3}$-alkyl, $C_{1-3}$-alkyl, or $C_{1-3}$-alkyloxy, particularly hydroxy, hydroxymethyl, methyl, or methoxy, and alkyl groups may be mono- or polysubstituted by F and/or monosubstituted by Cl.

Particularly preferred definitions of the groups $R^1$ and/or $R^2$ are also selected from among H, $C_{1-4}$-alkyl, $C_{3-5}$-alkenyl, $C_{3-5}$-alkynyl, $C_{3-7}$-cycloalkyl, $C_{3-7}$-cycloalkyl-$C_{1-3}$-alkyl, $C_{1-4}$-alkoxy-$C_{2-3}$-alkyl, pyridyl, and benzyl, while the alkyl, cycloalkyl, or cycloalkylalkyl group may be mono- or disubstituted by hydroxy, mono- or polysubstituted by F or monosubstituted by Br, Cl, or CN, and one of the groups $R^1$ and $R^2$ may also represent H.

Most particularly preferred groups $R^1$ and/or $R^2$ are selected from among H, methyl, ethyl, n-propyl, isopropyl, n-butyl, isobutyl, propen-3-yl, propin-3-yl, cyclopropyl, cyclopentyl, cyclohexyl, cyclopropylmethyl, cyclopentylmethyl, cyclohexylmethyl, phenyl, pyridyl, phenylmethyl, pyridylmethyl, tetrahydropyran-4-yl, tetrahydropyran-4-ylmethyl, piperidin-4-yl, N—($C_{1-4}$-alkyl)-piperidin-4-yl, piperidin-4-ylmethyl, N—($C_{1-4}$-alkyl)-piperidin-4-ylmethyl, while the abovementioned ethyl, propyl, and butyl groups may be monosubstituted by amino, methylamino, or dimethylamino, or mono- or disubstituted by hydroxy, methoxy, or ethoxy, and the abovementioned cycloalkyl rings may be mono- or disubstituted by hydroxy, hydroxymethyl, or methyl, and methyl groups may be mono- or polysubstituted by fluorine.

Examples of most particularly preferred definitions of the groups $R^1$ and/or $R^2$ are methyl, ethyl, n-propyl, isopropyl, 2-hydroxyethyl, 2-hydroxypropyl, 3-hydroxypropyl, 2-hydroxy-2-methylpropyl, 2-methoxyethyl, 3-aminopropyl, propen-3-yl, propin-3-yl, cyclopropyl, cyclopentyl, cyclohexyl, cyclopropylmethyl, cyclopentylmethyl, (1-hydroxycyclopropyl)methyl, phenyl, pyridyl, phenylmethyl, pyridylmethyl, tetrahydropyran-4-yl, N-methylpiperidin-4-yl, N-(methylcarbonyl)piperidin-4-yl, and N-(tert-butyloxycarbonyl)piperidin-4-yl, while hydroxyalkyl groups may additionally be substituted by hydroxy, and one of the groups $R^1$, $R^2$ may also represent H.

If the substituent $R^1$ has one of the meanings stated above as being preferred, but not H, the substituent $R^2$ most particularly preferably denotes H, methyl, ethyl, n-propyl, isopropyl, 2-hydroxyethyl, or 2-methoxyethyl.

Particularly preferably at least one of the groups $R^1$, $R^2$, and most particularly preferably both groups, have a meaning other than H.

If $R^1$ and $R^2$ form an alkylene bridge, this is preferably a $C_{3-7}$-alkylene bridge, wherein a —$CH_2$— group not adjacent to the N atom of the $R^1R^2N$— group may be replaced by —CH=CH— and/or a —$CH_2$— group which is preferably not adjacent to the N atom of the $R^1R^2N$— group may be replaced by —O—, —S—, —CO—, —C(=$CH_2$)—, or —$NR^{13}$—, particularly preferably by —O—, —S— or, —$NR^{13}$—, in such a way that heteroatoms are not directly joined together and a group —CO— is not directly linked to the group $R^1R^2N$—, while in the alkylene bridge defined hereinbefore one or more H atoms may be replaced by $R^{14}$, and the alkylene bridge defined hereinbefore may be substituted by a carbo- or heterocyclic group Cy in such a way that the bond between the alkylene bridge and the group Cy is made via a single or double bond, via a common C atom forming a spirocyclic ring system, via two common adjacent C and/or N atoms forming a fused bicyclic ring system, or via three or more C and/or N atoms forming a bridged ring system.

$R^{13}$ preferably denotes H, $C_{1-6}$-alkyl, $C_{1-4}$-alkylcarbonyl, or $C_{1-4}$-alkyloxycarbonyl. $R^{13}$ particularly preferably denotes H or $C_{1-6}$-alkyl, particularly H, methyl, ethyl, or propyl.

Preferably also $R^1$ and $R^2$ form an alkylene bridge such that $R^1R^2N$— denotes a group selected from azetidine, pyrrolidine, piperidine, azepan, 2,5-dihydro-1H-pyrrole, 1,2,3,6-tetrahydropyridine, 2,3,4,7-tetrahydro-1H-azepine, and 2,3, 6,7-tetrahydro-1H-azepine, piperazine wherein the free imine function is substituted by $R^{13}$, piperidin-4-one, morpholine, and thiomorpholine, particularly selected from pyrrolidine, piperidine, piperidin-4-one, 2,5-dihydro-1H-pyrrole, piperazine, wherein the free imine function is substituted by $R^{13}$, morpholine, and thiomorpholine, while according to the general definition of $R^1$ and $R^2$ one or more H atoms may be replaced by $R^{14}$, and/or the abovementioned groups may be substituted by one or two identical or different carbo- or heterocyclic groups Cy in a manner specified according to the general definition of $R^1$ and $R^2$. Particularly preferred groups Cy for this are phenyl, $C_{3-7}$-cycloalkyl, aza-$C_{4-7}$-cycloalkyl, particularly phenyl, $C_{3-6}$-cycloalkyl, and cyclo-$C_{3-5}$-alkyleneimino, as well as N—$C_{1-4}$-alkyl-(aza-$C_{4-6}$-cycloalkyl)-, while the cyclic groups Cy may be substituted as specified.

The alkylene bridge formed by $R^1$ and $R^2$, wherein —$CH_2$— groups may be replaced as specified, may be substituted, as described, by one or two identical or different carbo- or heterocyclic groups Cy, which may be substituted as defined hereinbefore.

In the event that the alkylene bridge is linked to a group Cy via a single bond, Cy is preferably selected from the group consisting of $C_{3-7}$-cycloalkyl, cyclo-$C_{3-6}$-alkyleneimino, piperazinyl, 1H-imidazole, thienyl, and phenyl, particularly $C_{3-6}$-cycloalkyl, pyrrolidinyl, piperidinyl, and piperazinyl, which may be substituted as specified, and particularly the N atoms may be substituted by $C_{1-4}$-alkyl in each case.

In the event that the alkylene bridge is linked to a group Cy via a common C atom forming a spirocyclic ring system, Cy is preferably selected from the group consisting of $C_{3-7}$-cycloalkyl, aza-$C_{4-8}$-cycloalkyl, oxa-$C_{4-8}$-cycloalkyl, and 2,3-dihydro-1H-quinazolin-4-one, particularly cyclopentyl and cyclohexyl, which may be substituted as specified, and particularly the N atoms may be substituted by $C_{1-4}$-alkyl in each case.

In the event that the alkylene bridge is linked to a group Cy via two common adjacent C and/or N atoms forming a fused bicyclic ring system, Cy is preferably selected from the group consisting of $C_{4-7}$-cycloalkyl, aza-$C_{4-7}$-cycloalkyl, phenyl, and thienyl, particularly phenyl and pyrrolidinyl, which may be substituted as specified, and particularly the N atoms may be substituted by $C_{1-4}$-alkyl in each case.

In the event that the alkylene bridge is linked to a group Cy via three or more C and/or N atoms forming a bridged ring system, Cy preferably denotes $C_{4-8}$-cycloalkyl or aza-$C_{4-8}$-cycloalkyl.

Particularly preferably the group

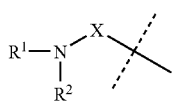

is defined according to one of the following partial formulae

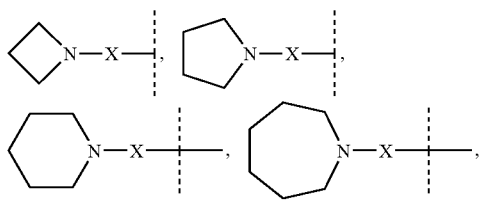

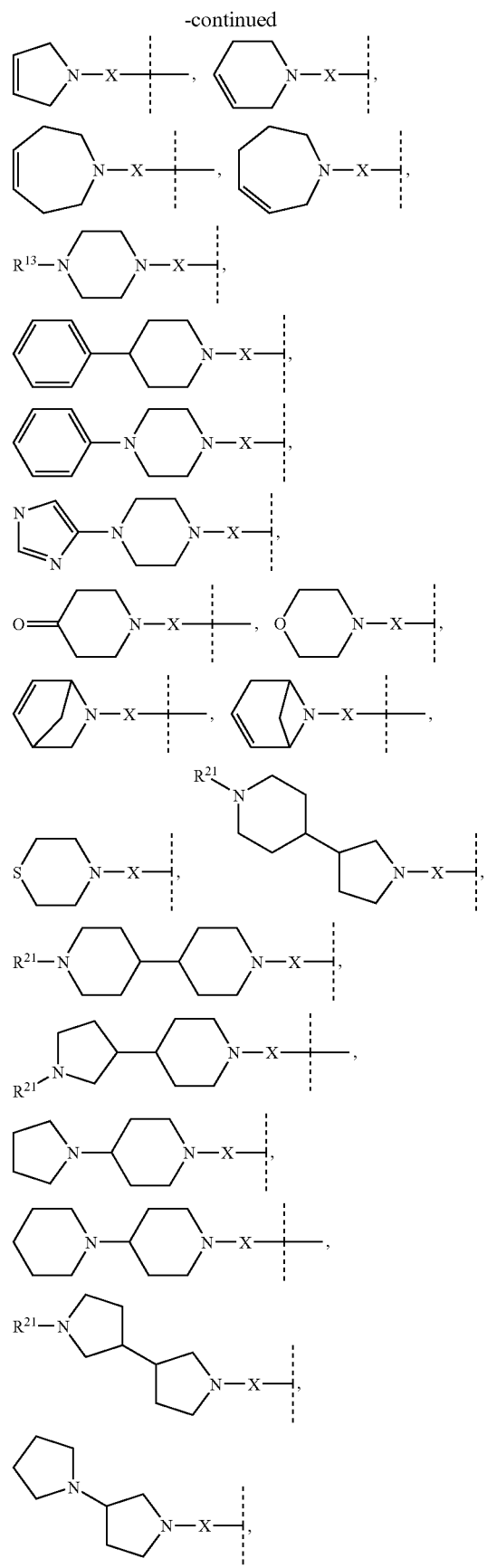

-continued

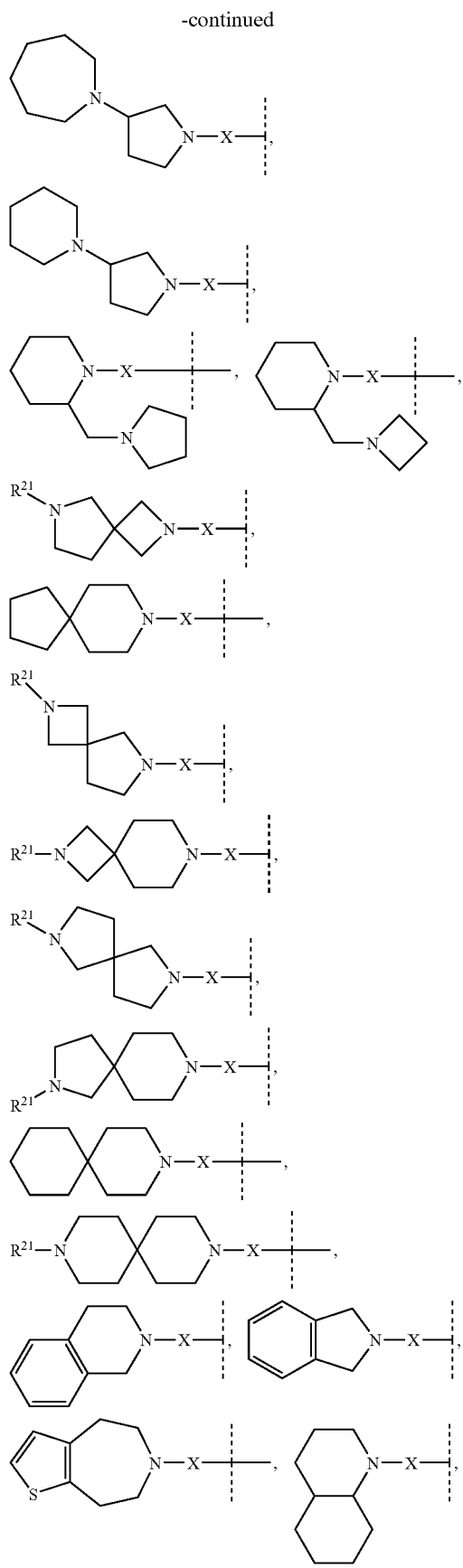

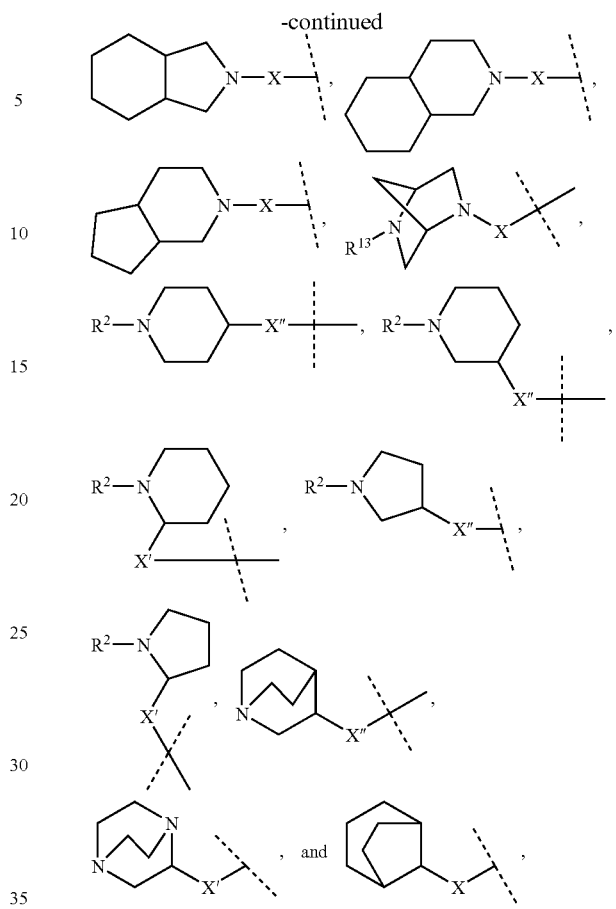

while in the heterocycle formed by the group $R^1R^2N-$ one or more H atoms may be replaced by $R^{14}$ and/or a H atom may be substituted by Cy defined as $C_{3-7}$-cycloalkyl, which may be mono- or polysubstituted by $R^{20}$, particularly by F, hydroxy, $C_{1-3}$-alkyl, $CF_3$, $C_{1-3}$-alkyloxy, $OCF_3$, or hydroxy-$C_{1-3}$-alkyl, and the ring connected to the heterocycle formed by the group $R^1R^2N-$ may be mono- or polysubstituted at one or more C atoms by $R^{20}$, and in the case of a phenyl ring may also additionally be monosubstituted by nitro; and X' and X" independently of one another denote a single bond or $C_{1-3}$-alkylene and in the event that the group Y is linked to X' or X" via a C atom (of the group Y), may also denote $-C_{1-3}$-alkylene-O$-$, $-C_{1-3}$-alkylene-NH$-$, or $-C_{1-3}$-alkylene-N($C_{1-3}$-alkyl), and X" additionally also denotes $-O-C_{1-3}$-alkylene, $-NH-C_{1-3}$-alkylene or $-N(C_{1-3}$-alkyl)-$C_{1-3}$-alkylene and in the event that the group Y is linked to X" via a C atom (of the group Y), also denotes $-NH-$, $-N(C_{1-3}$-alkyl)-, or $-O-$, while in the meanings given for X' and X" hereinbefore in each case a C atom may be substituted by $R^{10}$, preferably by a hydroxy, ω-hydroxy-$C_{1-3}$-alkyl, ω-($C_{1-4}$-alkoxy)-$C_{1-3}$-alkyl, and/or $C_{1-4}$-alkoxy group, and/or one or two C atoms in each case may be substituted by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl, and $C_{4-7}$-cycloalkenyl-$C_{1-3}$-alkyl, while two alkyl and/or alkenyl substituents may be joined together, forming a carbocyclic ring system, and in X', X" independently of one another in each case one or more C atoms may be mono- or polysubstituted by F and/or in each case one or two C atoms independently of one another may be monosubstituted by Cl or Br, wherein $R^2$, $R^{10}$, $R^{13}$, $R^{14}$, $R^{18}$, $R^{20}$, $R^{21}$, and X have the meanings given above and hereinafter.

Preferably X' and X" independently of one another represent a single bond or $C_{1-3}$-alkylene and in the event that the group Y is linked to X' or X" via a C atom, may also denote —$C_{1-3}$-alkylene-O—, —$C_{1-3}$-alkylene-NH—, or —$C_{1-3}$-alkylene-N($C_{1-3}$-alkyl)-, and X" additionally also denotes —O—$C_{1-3}$-alkylene, —NH—$C_{1-3}$-alkylene, or —N($C_{1-3}$-alkyl)-$C_{1-3}$-alkylene and in the event that the group Y is linked to X" via a C atom, X" also denotes —NH—, —N($C_{1-3}$-alkyl)-, or —O—. Particularly preferably X' and X" independently of one another represent a single bond or methylene and in the event that the group Y is linked to X' or X" via a C atom, also represent —$CH_2$—O—, —$CH_2$—NH—, or —$CH_2$—N($C_{1-3}$-alkyl)-, and in the event that the group Y is linked to X" via a C atom, X" also denotes —NH—, —N($C_{1-3}$-alkyl), or —O—.

In the preferred and particularly preferred meanings of $R^1R^2N$— listed above the following definitions of the substituent $R^{14}$ are preferred: F, Cl, Br, $C_{1-4}$-alkyl, $C_{2-4}$-alkenyl, $C_{2-4}$-alkynyl, $C_{3-7}$-cycloalkyl-$C_{1-3}$-alkyl, hydroxy, hydroxy-$C_{1-3}$-alkyl, $C_{1-4}$-alkoxy, ω-($C_{1-4}$-alkoxy)-$C_{1-3}$-alkyl, $C_{1-4}$-alkyl-carbonyl, carboxy, $C_{1-4}$-alkoxycarbonyl, hydroxy-carbonyl-$C_{1-3}$-alkyl, $C_{1-4}$-alkoxycarbonyl-$C_{1-3}$-alkyl, $C_{1-4}$-alkoxy-carbonylamino, $C_{1-4}$-alkoxy-carbonylamino-$C_{1-3}$-alkyl, amino, $C_{1-4}$-alkyl-amino, $C_{3-7}$-cycloalkyl-amino, N—($C_{3-7}$-cycloalkyl)-N—($C_{1-4}$-alkyl)-amino, di-($C_{1-4}$-alkyl)-amino, amino-$C_{1-3}$-alkyl, $C_{1-4}$-alkyl-amino-$C_{1-3}$-alkyl, $C_{3-7}$-cycloalkyl-amino-$C_{1-3}$-alkyl, N—($C_{3-7}$-cycloalkyl)-N—($C_{1-4}$-alkyl)-amino-$C_{1-3}$-alkyl, di-($C_{1-4}$-alkyl)-amino-$C_{1-3}$-alkyl, cyclo-$C_{3-6}$-alkyleneimino-$C_{1-3}$-alkyl, aminocarbonyl, $C_{1-4}$-alkyl-aminocarbonyl, $C_{3-7}$-cycloalkyl-aminocarbonyl, N—($C_{3-7}$-cycloalkyl)-N—($C_{1-4}$-alkyl)-aminocarbonyl, di-($C_{1-4}$-alkyl)-aminocarbonyl, pyridinyloxy, pyridinylamino, pyridinyl-$C_{1-3}$-alkyl-amino-. In the above meanings of the group $R^{14}$ one or more C atoms may be mono- or polysubstituted by F and/or one or two C atoms independently of one another may be monosubstituted by Cl or Br, and in particular alkyl groups may be mono- or polysubstituted by fluorine.

Most particularly preferred meanings of the substituent $R^{14}$ are F, Cl, $C_{1-4}$-alkyl, $C_{3-6}$-cycloalkyl-$C_{1-3}$-alkyl, hydroxy, hydroxy-$C_{1-3}$-alkyl, $C_{1-4}$-alkoxy, $C_{1-4}$-alkoxy-$C_{1-3}$-alkyl, amino-$C_{1-3}$-alkyl, $C_{1-4}$-alkyl-amino-$C_{1-3}$-alkyl, $C_{3-7}$-cycloalkyl-amino-$C_{1-3}$-alkyl, N—($C_{3-7}$-cycloalkyl)-N—($C_{1-4}$-alkyl)-amino-$C_{1-3}$-alkyl, di-($C_{1-4}$-alkyl)-amino-$C_{1-3}$-alkyl, cyclo-$C_{3-6}$-alkyleneimino-$C_{1-3}$-alkyl, aminocarbonyl, and pyridylamino. In the above meanings of the group $R^{14}$, one or more C atoms, and particularly alkyl groups, may be mono- or polysubstituted by fluorine. Thus, preferred meanings of $R^{14}$ also include, for example, —$CF_3$ and —$OCF_3$.

If in the heterocycle formed by the group $R^1R^2N$— an H atom is replaced by Cy representing $C_{3-7}$-cycloalkyl, which may be mono- or polysubstituted by $R^{20}$, Cy preferably denotes $C_{3-6}$-cycloalkyl and $R^{20}$ preferably denotes F, hydroxy, $C_{1-3}$-alkyl, $CF_3$, $C_{1-3}$-alkyloxy, $OCF_3$, or hydroxy-$C_{1-3}$-alkyl, particularly F, hydroxy, methyl, methoxy, $CF_3$, $OCF_3$, or hydroxymethyl. Particularly preferred meanings of Cy are $C_{3-6}$-cycloalkyl and 1-hydroxy-$C_{3-5}$-cycloalkyl.

Most particularly preferably the group

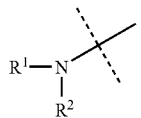

is defined according to one of the following partial formulae

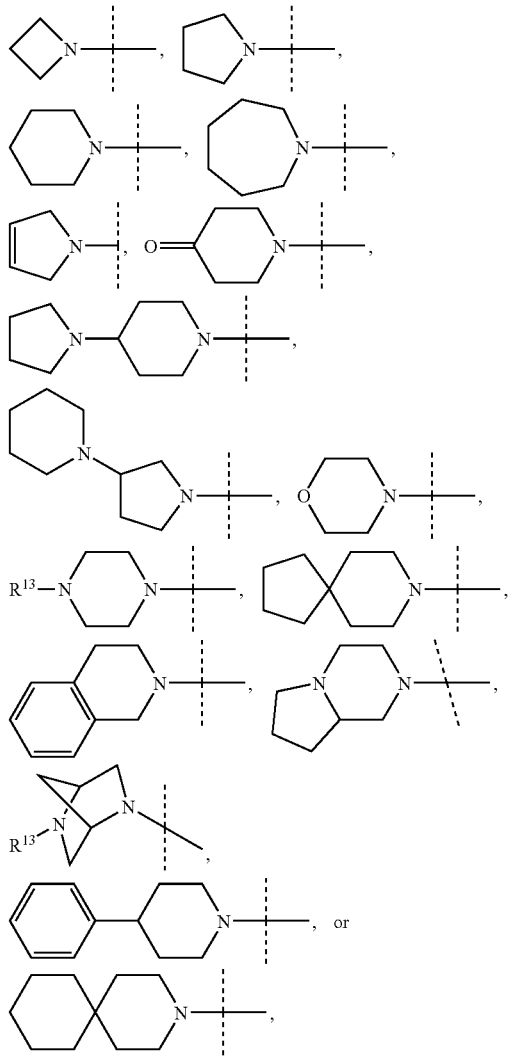

while the group $R^{13}$ has the meanings given hereinbefore and hereinafter, and in the heterocycle formed by the group $R^1R^2N$— one or more H atoms may be replaced by $R^{14}$ and/or an H atom may be replaced by Cy representing $C_{3-6}$-cycloalkyl, which may be mono- or polysubstituted by $R^{20}$, particularly by F, hydroxy, $C_{1-3}$-alkyl, $CF_3$, $C_{1-3}$-alkyloxy, $OCF_3$, or hydroxy-$C_{1-3}$-alkyl, particularly preferably by F, hydroxy, methyl, methoxy, $CF_3$, $OCF_3$, or hydroxymethyl, and the ring connected to the heterocycle formed by the group $R^1R^2N$— may be mono- or polysubstituted, preferably monosubstituted at one or more C atoms by $R^{20}$, or in the case of a phenyl ring may also additionally be monosubstituted by nitro;

$R^{14}$ in each case independently of one another denotes F, Cl, $C_{1-4}$-alkyl, $C_{3-6}$-cycloalkyl-$C_{1-3}$-alkyl, hydroxy, hydroxy-$C_{1-3}$-alkyl, $C_{1-4}$-alkyloxy, $C_{1-4}$-alkoxy-$C_{1-3}$-alkyl, pyridylamino, or aminocarbonyl, while in each case one or more C atoms, particularly alkyl groups may additionally be mono- or polysubstituted by F; most particularly preferably denotes methyl, ethyl, propyl, trifluoromethyl, hydroxy, hydroxymethyl, 1-hydroxyethyl, 2-hydroxyethyl, 1-hydroxy-1-methyl-ethyl, 1-hydroxycyclopropyl, methoxy, ethoxy, methoxymethyl, pyridylamino, or aminocarbonyl; and $R^{13}$ is as hereinbefore defined, particularly denotes H or $C_{1-3}$-alkyl.

Preferably X denotes a $C_{1-6}$-alkylene bridge, wherein a —$CH_2$— group not adjacent to the N atom of the $R^1R^2N$— group may be replaced by —CH=CH— or —C≡C— and/or a —$CH_2$— group not adjacent to the N atom of the $R^1R^2N$ group may be replaced by —O—, —S—, —CO—, or —$NR^4$—, particularly preferably by —O—, —S—, or —$NR^4$—, in such a way that in each case two O, S, or N atoms or an O and an S atom are not directly joined together, while $R^4$ may be attached to Y, forming a heterocyclic ring system with one another, while the bridge X may be connected to $R^1$ including the N atom linked to $R^1$ and X, forming a heterocyclic group, and a C atom not directly connected to a heteroatom may be substituted by $R^{10}$ and/or one or two C atoms may each be substituted by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl, and $C_{4-7}$-cycloalkenyl-$C_{1-3}$-alkyl, particularly $C_{1-4}$-alkyl, while two alkyl and/or alkenyl substituents may be joined together forming a carbocyclic ring system, particularly a cyclopropyl, cyclobutyl, or cyclopentyl group.

In the abovementioned definition of the bridge X two C atoms or a C and an N atom of the alkylene bridge may be joined together by an additional $C_{1-4}$-alkylene bridge.

Preferably, in the group X a —$CH_2$— group directly adjacent to the group $R^1R^2N$— is not replaced by —O—, —S—, —(SO)—, —(SO$_2$)—, —CO—, or —$NR^4$—.

If in the group X one or two —$CH_2$— groups independently of one another are replaced by —O—, —S—, —(SO)—, —(SO$_2$)—, —CO—, or —$NR^4$—, these groups are preferably spaced from the $R^1R^2N$— group by an alkylene bridge with at least 2 C atoms.

If in the group X two —$CH_2$ groups independently of one another are replaced by —O—, —S—, —(SO)—, —(SO$_2$)—, —CO—, or —$NR^4$—, these groups are preferably separated from one another by an alkylene bridge with at least 2 C atoms.

If in the group X a —$CH_2$— group of the alkylene bridge is replaced according to the invention, this —$CH_2$— group is preferably not directly connected to a heteroatom, a double or triple bond.

Preferably the alkylene bridge X, X', or X" has no imino groups or at most only one imino group. The position of the imino group within the alkylene bridge X, X', or X" is preferably selected so that no aminal function is formed together with the amino group $NR^1R^2$ or another adjacent amino group, or two N atoms are not adjacent to one another.

Preferably X denotes an unbranched $C_{1-4}$-alkylene bridge and in the event that the group Y is linked to X via a C atom (of the group Y), it also denotes —$CH_2$—CH=CH—, —$CH_2$—C≡C—, $C_{2-4}$-alkylenoxy, or $C_{2-4}$-alkylene-$NR^4$—, particularly $C_{2-4}$-alkylenoxy or $C_{2-4}$-alkylene-$NR^4$—, while $R^4$ may be connected to Y, forming a heterocyclic ring system, while the bridge X may be connected to $R^1$, including the N atom connected to $R^1$ and X, forming a heterocyclic group, and in X a C atom may be substituted by $R^{10}$ and/or one or two C atoms may be substituted in each case by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl, and $C_{4-7}$-cycloalkenyl-$C_{1-3}$-alkyl, particularly $C_{1-4}$-alkyl, while two alkyl and/or alkenyl substituents may be joined together, forming a carbocyclic ring system, and in the abovementioned groups and radicals one or more C atoms may be mono- or polysubstituted by F and/or one or two C atoms independently of one another may be monosubstituted by Cl or Br, and $R^1$, $R^4$, and $R^{10}$ are as hereinbefore defined.

Particularly preferably X denotes —$CH_2$—, —$CH_2$—$CH_2$—, —$CH_2$—$CH_2$—$CH_2$—, or —$CH_2$—CH=CH—$CH_2$— and in the event that the group Y is linked to X via a C atom (of the group Y), X also denotes —$CH_2$—CH=CH—, —$CH_2$—C≡C—, —$CH_2$—$CH_2$—O—, —$CH_2$—$CH_2$—$CH_2$—O—, —$CH_2$—$CH_2$—$NR^4$—, or —$CH_2$—$CH_2$—$CH_2$—$NR^4$—, particularly —$CH_2$—$CH_2$—O—, —$CH_2$—$CH_2$—$CH_2$—O—, —$CH_2$—$CH_2$—$NR^4$—, or —$CH_2$—$CH_2$—$CH_2$—$NR^4$—, while $R^4$ may be connected to Y forming a heterocyclic ring system with one another, while the bridge X may be connected to $R^1$ including the N atom connected to $R^1$ and X, forming a heterocyclic group, and in X a C atom may be substituted by $R^{10}$, preferably a hydroxy, ω-hydroxy-$C_{1-3}$-alkyl, ω-($C_{1-4}$-alkoxy)-$C_{1-3}$-alkyl and/or $C_{1-4}$-alkoxy group, and/or one or two C atoms independently of one another may each be substituted by one or two identical or different $C_{1-4}$-alkyl groups, while two alkyl groups may be joined together, forming a carbocyclic ring system, and in each case one or more C atoms may be mono- or polysubstituted by F and/or in each case one or two C atoms may independently of one another be monosubstituted by Cl or Br.

Most particularly preferably, in the event that the group Y is linked to X via a C atom (of the group Y), X denotes —$CH_2$—, —$CH_2$—$CH_2$—, —$CH_2$—$CH_2$—$CH_2$—, —$CH_2$—$CH_2$—O—, —$CH_2$—$CH_2$—$CH_2$—O—, —$CH_2$—$CH_2$—$NR^4$—, or —$CH_2$—$CH_2$—$CH_2$—$NR^4$—, which may be unsubstituted or substituted as described.

$R^4$ has one of the meanings given for $R^{17}$, preferably has one of the meanings given for $R^{16}$.

Particularly preferred meanings of the substituent $R^4$ are H, $C_{1-6}$-alkyl, and $C_{3-6}$-alkenyl. Most particularly preferably $R^4$ denotes H, methyl, or ethyl. If $R^4$ is joined to Y, forming a heterocyclic ring system, particularly preferred meanings of $R^4$ are $C_{2-6}$-alkyl and $C_{2-6}$-alkenyl.

In the event that $R^4$ is linked to Y forming a heterocyclic ring system with one another, Y preferably denotes phenyl and $R^4$ preferably denotes $C_{2-6}$-alkyl or $C_{2-6}$-alkenyl. The heterocyclic ring systems preferably formed are indole, dihydroindole, quinoline, dihydroquinoline, tetrahydroquinoline, and benzoxazole.

The group $R^4$ preferably denotes vinyl only when $R^4$ is linked to Y forming a heterocyclic ring system.

The substituent $R^{10}$ preferably denotes hydroxy, ω-hydroxy-$C_{1-3}$-alkyl, $C_{1-4}$-alkoxy, or ω-($C_{1-4}$-alkoxy)-$C_{1-3}$-alkyl, particularly hydroxy, hydroxymethyl, or methoxy.

The group X preferably does not comprise a carbonyl group.

If in X, X', or X" a C atom is substituted, preferred substituents are selected from among the $C_{1-4}$-alkyl, $C_{2-4}$-alkenyl, $C_{2-4}$-alkynyl, $C_{3-7}$-cycloalkyl, $C_{3-7}$-cycloalkyl-$C_{1-3}$-alkyl, hydroxy, ω-hydroxy-$C_{1-3}$-alkyl, ω-($C_{1-4}$-alkoxy)-$C_{1-3}$-alkyl, and $C_{1-4}$-alkoxy groups. Moreover in X, X', or X" a C atom may be disubstituted and/or one or two C atoms may be mono- or disubstituted, while preferred substituents are selected from among $C_{1-4}$-alkyl, $C_{2-4}$-alkenyl, $C_{2-4}$-alkynyl, $C_{3-7}$-cycloalkyl, and $C_{3-7}$-cycloalkyl-$C_{1-3}$-alkyl, particularly $C_{1-4}$-alkyl, and two $C_{1-4}$-alkyl and/or $C_{2-4}$-alkenyl substituents may also be joined together to form a saturated or monounsaturated carbocyclic ring.

If in the group X, X', or X" one or more C atoms are substituted by a hydroxy and/or $C_{1-4}$-alkoxy group, the substituted C atom is preferably not immediately adjacent to another heteroatom.

Most particularly preferred substituents of one or two C atoms in X, X', or X" are selected from methyl, ethyl, n-propyl, isopropyl, cyclopropyl, cyclopropylmethyl, while two alkyl substituents at a C atom may be joined together to form a carbocyclic ring.

In the definitions of the substituents of the bridges X, X', and/or X" and the definitions of the bridges X, X', and/or X" themselves mentioned above and hereinafter, in each case one or more C atoms may additionally be mono- or polysubstituted by F and/or in each case one or two C atoms independently of one another may additionally be monosubstituted by Cl or Br.

If in the group X, X', or X" one or more C atoms are substituted as specified hereinbefore, particularly preferred meanings of X, X', and X" are selected from among

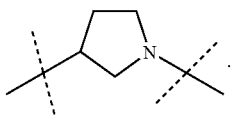

-continued

If Y denotes a fused bicyclic ring system, a preferred definition of the group X is —$CH_2$—, —$CH_2$—$CH_2$—, and —$CH_2$—$CH_2$—$CH_2$—, particularly —$CH_2$— or —$CH_2$—$CH_2$—, which may be substituted as specified.

The group Y preferably has a meaning selected from among the bivalent cyclic groups phenyl, pyridinyl, naphthyl, tetrahydronaphthyl, indolyl, dihydroindolyl, quinolinyl, dihydroquinolinyl, tetrahydroquinolinyl, isoquinolinyl, dihydroisoquinolinyl, tetrahydro-isoquinolinyl, benzimidazolyl, benzoxazolyl, chromanyl, chromen-4-onyl, thienyl, benzothienyl, pyrimidinyl, or benzofuranyl, while the above-mentioned cyclic groups may be mono- or polysubstituted at one or more C atoms by $R^{20}$, in the case of a phenyl ring may also additionally be monosubstituted by nitro, and/or at one or more N atoms may be substituted by $R^{21}$. $R^1$ may be connected to Y and/or X may be connected to Y as specified hereinbefore, while Y preferably denotes phenyl.

If the group Y denotes phenyl or pyridinyl, the bridges X and Z are preferably connected to the group Y in the para-position.

Particularly preferably the group Y has a meaning selected from among the bivalent cyclic groups

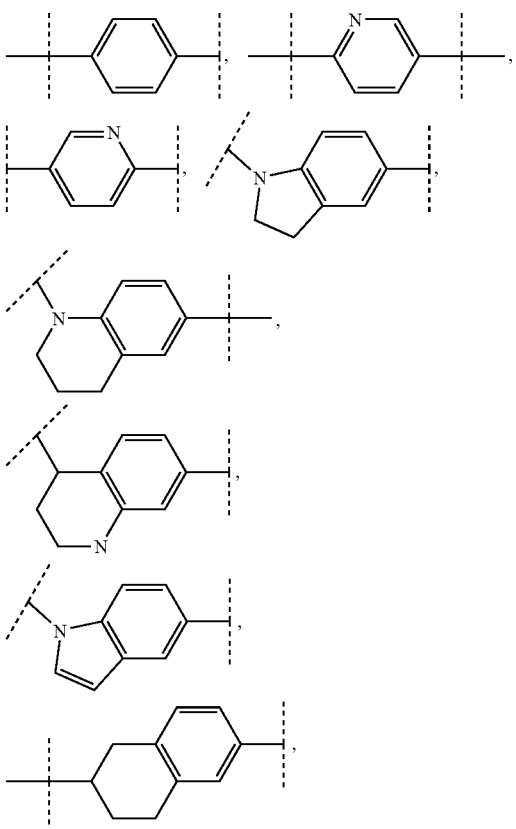

-continued

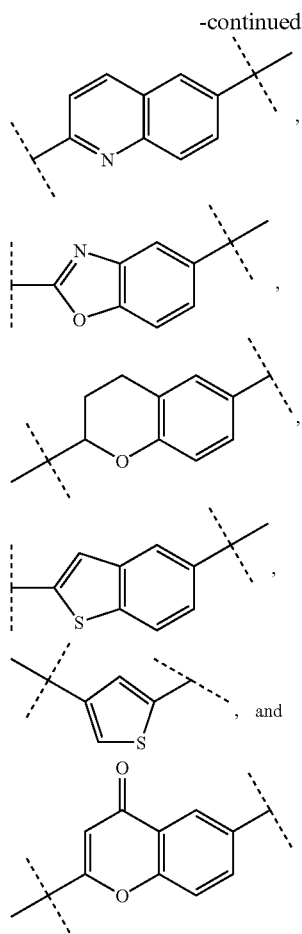

in particular Y has one of the following meanings

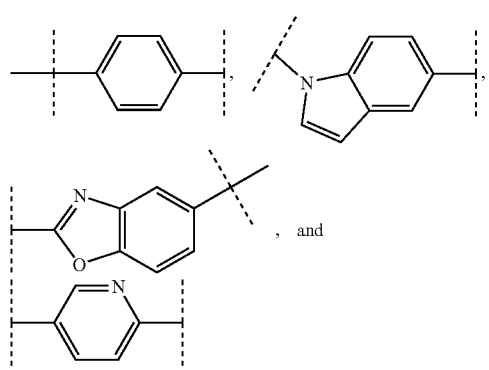

while the abovementioned cyclic groups may be mono- or polysubstituted by $R^{20}$ at one or more C atoms, and in the case of a phenyl ring may also additionally be monosubstituted by nitro, and/or one or more NH groups may be substituted by $R^{21}$.

The group Y representing phenyl may be linked to the group X forming a carbo- or heterocyclic group fused to Y. Preferred definitions of the groups —X—Y— linked to one another are selected from the list comprising

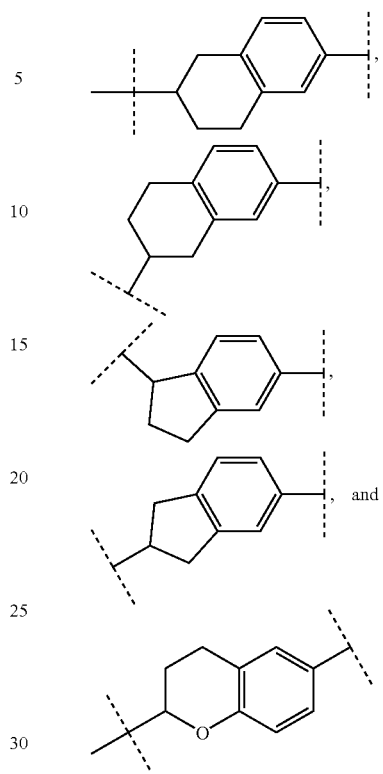

while the abovementioned cyclic groups may be mono- or polysubstituted by $R^{20}$ at one or more C atoms, and in the case of a phenyl ring may also additionally be monosubstituted by nitro.

The group Y is preferably unsubstituted or mono- or disubstituted.

Particularly preferred substituents $R^{20}$ of the group Y are selected from among fluorine, chlorine, bromine, cyano, nitro, $C_{1-4}$-alkyl, $C_{2-6}$-alkenyl, hydroxy, hydroxy-$C_{1-3}$-alkyl, $C_{1-4}$-alkoxy, trifluoromethyl, trifluoromethoxy, $C_{2-4}$-alkynyl, $C_{1-4}$-alkoxycarbonyl, $C_{1-4}$-alkoxy-$C_{1-3}$-alkyl, $C_{1-4}$-alkoxycarbonylamino, amino, $C_{1-4}$-alkyl-amino, di-($C_{1-4}$-alkyl)-amino, aminocarbonyl, $C_{1-4}$-alkyl-aminocarbonyl, and di-($C_{1-4}$-alkyl)-aminocarbonyl.

Most particularly preferred substituents $R^{20}$ of the group Y are selected from among fluorine, chlorine, bromine, cyano, $C_{1-3}$-alkyl, $C_{1-3}$-alkoxy, $C_{1-4}$-alkoxycarbonyl, trifluoromethyl, trifluoromethoxy, amino, and in the case of a phenyl ring also nitro.

Most particularly preferably the group Y denotes substituted phenylene of the partial formula

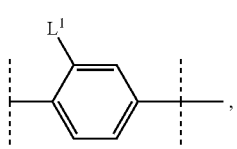

wherein $L^1$ has one of the meanings given previously for $R^{20}$, preferably F, Cl, Br, I, $CH_3$, $CF_3$, $OCH_3$, $OCF_3$, methoxycarbonyl, ethoxycarbonyl, CN, amino, or NO$_2$, or denotes H. Particularly preferred meanings of the substituent L$^1$ are H, Cl, or methoxy.

The bridge Z denotes a single bond or —CR$^{7a}$R$^{7b}$—CR$^{7c}$R$^{7d}$, wherein R$^{7a}$, R$^{7b}$, R$^{7c}$, R$^{7d}$ independently of one another preferably represent H, F, CH$_3$, or CF$_3$.

Other preferred definitions of the bridge Z are selected from:

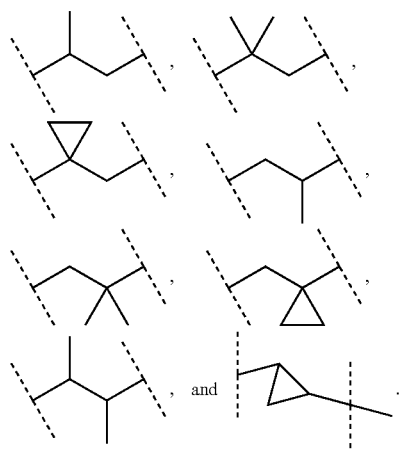

Particularly preferred definitions of the bridge Z are a single bond and —CH$_2$—CH$_2$—. Most particularly preferably Z is a single bond.

A preferred meaning of the group A is aryl or heteroaryl.

Preferably the group A is selected from among the cyclic groups phenyl, pyridinyl, or naphthyl, which may be mono- or polysubstituted by R$^{20}$ at one or more C atoms, and in the case of a phenyl ring may also additionally be monosubstituted by nitro.

If b the value 0, the group A is preferably mono-, di-, or trisubstituted.

If b has the value 1, the group A is preferably unsubstituted or mono- or disubstituted. If b has the value 1 and the group A is monosubstituted, the substituent is preferably in the ortho-position based on the β-ketoamide group.

Most particularly preferably A is one of the following groups

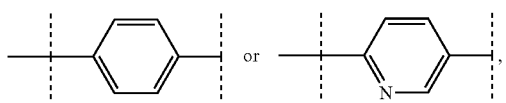

while these groups may be mono- or polysubstituted by R$^{20}$ as specified.

Particularly preferred substituents R$^{20}$ of the group A are selected from among fluorine, chlorine, bromine, cyano, C$_{1-4}$-alkyl, C$_{2-6}$-alkenyl, hydroxy, hydroxy-C$_{1-3}$-alkyl, C$_{1-4}$-alkoxy, trifluoromethyl, trifluoromethoxy, C$_{2-4}$-alkynyl, carboxy, C$_{1-4}$-alkoxycarbonyl, C$_{1-4}$-alkoxy-C$_{1-3}$-alkyl, C$_{1-4}$-alkoxy-carbonylamino, amino, C$_{1-4}$-alkyl-amino, di-(C$_{1-4}$-alkyl)-amino, cyclo-C$_{3-6}$-alkyleneimino, aminocarbonyl, C$_{1-4}$-alkyl-aminocarbonyl, and di-(C$_{1-4}$-alkyl)-aminocarbonyl.

Most particularly preferred substituents R$^{20}$ of the group A are selected from among fluorine, chlorine, bromine, cyano, C$_{1-4}$-alkyl, C$_{1-4}$-alkoxy, trifluoromethyl, trifluoromethoxy, carboxy, C$_{1-4}$-alkoxycarbonyl, C$_{1-4}$-alkyl-amino, and di-(C$_{1-4}$-alkyl)-amino.

In the event that b has the value 0, a particularly preferred definition of the group A is substituted phenyl of the partial formula

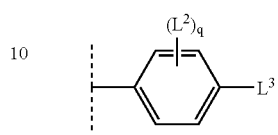

wherein:

L$^2$ has one of the meanings given for R$^{20}$ or denotes H, preferably F, Cl, Br, I, CH$_3$, CF$_3$, OCH$_3$, OCF$_3$, CN, or NO$_2$, L$^3$ has one of the meanings given for R$^{20}$ or denotes H, preferably F, Cl, Br, I, CF$_3$, OCF$_3$, CN, NO$_2$, C$_{1-4}$-alkyl, C$_{3-7}$-cycloalkyl, C$_{3-7}$-cycloalkyl-C$_{1-3}$-alkyl, C$_{1-4}$-alkoxy, C$_{3-7}$-cycloalkyl-O, C$_{3-7}$-cycloalkyl-C$_{1-3}$-alkoxy, —COO—C$_{1-4}$-alkyl, or —COOH; particularly preferably F, Cl, Br, C$_{1-4}$-alkyl, CF$_3$, methoxy, OCF$_3$, CN, or NO$_2$; most particularly preferably Cl, Br, CF$_3$, or NO$_2$;

q has the value 0, 1, or 2, with the proviso that the phenyl group can be at most monosubstituted by nitro.

Particularly preferably A is substituted phenyl according to the above partial formula, wherein q denotes 1 or 2 and/or at least one substituent L$^2$ is in the meta-position to the substituent L$^3$.

A particularly preferred definition of the substituent L$^2$ is Cl.

Particularly preferred meanings of the substituent L$^3$ are Cl, methoxy, and CF$_3$.

In the event that b is 1, the group A preferably denotes unsubstituted phenyl or phenyl substituted by L$^2$, while L$^2$ is preferably in the ortho-position to the β-ketoamide group. L$^2$ is as hereinbefore defined.

In the event that b has the value 1, a preferred definition of the group B is aryl or heteroaryl, which may be substituted as specified.

Preferred definitions of the group B are selected from among phenyl, pyridyl, thienyl, and furanyl. Particularly preferably, the group B denotes phenyl. The group B defined as specified may be mono- or polysubstituted by R$^{20}$, a phenyl group may additionally also be monosubstituted by nitro. Preferably the group B is unsubstituted or mono-, di-, or trisubstituted, particularly unsubstituted or mono- or disubstituted. In the case of a monosubstitution the substituent is preferably in the ortho- or para-position, particularly in the para-position to the group A.

Preferred substituents R$^{20}$ of the group B are selected from among fluorine, chlorine, bromine, cyano, nitro, C$_{1-4}$-alkyl, hydroxy, hydroxy-C$_{1-3}$-alkyl, C$_{1-4}$-alkoxy, trifluoromethyl, trifluoromethoxy, C$_{2-4}$-alkynyl, carboxy, C$_{1-4}$-alkoxycarbonyl, C$_{1-4}$-alkoxy-C$_{1-3}$-alkyl, C$_{1-4}$-alkoxy-carbonylamino, amino, C$_{1-4}$-alkyl-amino, di-(C$_{1-4}$-alkyl)-amino, cyclo-C$_{3-6}$-alkyleneimino, aminocarbonyl, C$_{1-4}$-alkyl-amino-carbonyl, and di-(C$_{1-4}$-alkyl)-amino-carbonyl.

Particularly preferred substituents R$^{20}$ of the group B are selected from among fluorine, chlorine, bromine, cyano, CF$_3$, C$_{1-3}$-alkyl, C$_{1-4}$-alkoxy, trifluoromethoxy, and nitro; particularly fluorine, chlorine, bromine, methoxy, CF$_3$, and trifluoromethoxy.

Most particularly preferred substituents $R^{20}$ of the group B are selected from among chlorine and methoxy.

The following are preferred definitions of other substituents according to the invention:

Preferably the substituent $R^{13}$ has one of the meanings given for $R^{16}$. Particularly preferably $R^{13}$ denotes H, $C_{1-4}$-alkyl, $C_{3-7}$-cycloalkyl, $C_{3-7}$-cycloalkyl-$C_{1-3}$-alkyl, ω-hydroxy-$C_{2-3}$-alkyl, ω-($C_{1-4}$-alkoxy)-$C_{2-3}$-alkyl. Most particularly preferably $R^{13}$ denotes H or $C_{1-4}$-alkyl. The alkyl groups mentioned above may be monosubstituted by Cl or mono- or polysubstituted by F.

Preferred meanings of the substituent $R^{15}$ are H, $C_{1-4}$-alkyl, $C_{3-7}$-cycloalkyl, $C_{3-7}$-cycloalkyl-$C_{1-3}$-alkyl, while, as hereinbefore defined, in each case one or more C atoms may additionally be mono- or polysubstituted by F and/or in each case one or two C atoms independently of one another may additionally be monosubstituted by Cl or Br. Particularly preferably $R^{15}$ denotes H, methyl, ethyl, propyl, or butyl.

The substituent $R^{16}$ preferably denotes H, $C_{1-4}$-alkyl, $C_{3-7}$-cycloalkyl, $C_{3-7}$-cycloalkyl-$C_{1-3}$-alkyl, ω-hydroxy-$C_{2-3}$-alkyl, or ω-($C_{1-4}$-alkoxy)-$C_{2-3}$-alkyl, while, as hereinbefore defined, in each case one or more C atoms may additionally be mono- or polysubstituted by F and/or in each case one or two C atoms independently of one another may additionally be monosubstituted by Cl or Br. Particularly preferably $R^{16}$ denotes H, $C_{1-3}$-alkyl, $C_{3-6}$-cycloalkyl, or $C_{3-6}$-cycloalkyl-$C_{1-3}$-alkyl.

Preferably the substituent $R^{17}$ has one of the meanings given for $R^{16}$ as preferred meanings or denotes phenyl, phenyl-$C_{1-3}$-alkyl, pyridinyl, or $C_{1-4}$-alkylcarbonyl. Particularly preferably $R^{17}$ has one of the meanings given for $R^{16}$ as preferred meanings.

The substituent $R^{20}$ preferably denotes halogen, hydroxy, cyano, $C_{1-4}$-alkyl, $C_{2-4}$-alkenyl, $C_{2-4}$-alkynyl, $C_{3-7}$-cycloalkyl, $C_{3-7}$-cycloalkyl-$C_{1-3}$-alkyl, hydroxy-$C_{1-4}$-alkyl, $R^{22}$—$C_{1-3}$-alkyl, or has one of the meanings given for $R^{22}$ as preferred meanings, while, as hereinbefore defined, in each case one or more C atoms may additionally be mono- or polysubstituted by F and/or in each case one or two C atoms independently of one another may additionally be monosubstituted by Cl or Br.

Particularly preferred definitions of the group $R^{20}$ are halogen, hydroxy, cyano, $C_{1-4}$-alkyl, $C_{3-7}$-cycloalkyl, and $C_{1-4}$-alkoxy, while, as hereinbefore defined, in each case one or more C atoms may additionally be mono- or polysubstituted by F and/or in each case one or two C atoms independently of one another may additionally be monosubstituted by Cl or Br. Most particularly preferably $R^{20}$ denotes F, Cl, Br, I, OH, cyano, methyl, difluoromethyl, trifluoromethyl, ethyl, n-propyl, isopropyl, methoxy, difluoromethoxy, trifluoromethoxy, ethoxy, n-propoxy, isopropoxy, methoxycarbonyl, ethoxycarbonyl, or amino.

The substituent $R^{22}$ preferably denotes $C_{1-4}$-alkoxy, $C_{1-4}$-alkylthio, carboxy, $C_{1-4}$-alkylcarbonyl, $C_{1-4}$-alkoxycarbonyl, aminocarbonyl, $C_{1-4}$-alkylaminocarbonyl, di-($C_{1-4}$-alkyl)-aminocarbonyl, $C_{1-4}$-alkyl-sulfonyl, $C_{1-4}$-alkyl-sulfinyl, $C_{1-4}$-alkyl-sulfonylamino, amino, $C_{1-4}$-alkylamino, di-($C_{1-4}$-alkyl)-amino, $C_{1-4}$-alkyl-carbonyl-amino, hydroxy-$C_{1-3}$-alkylaminocarbonyl, aminocarbonyl amino, or $C_{1-4}$-alkylaminocarbonyl-amino, while, as hereinbefore defined, in each case one or more C atoms may additionally be mono- or polysubstituted by F and/or in each case one or two C atoms independently of one another may additionally be monosubstituted by Cl or Br.

Preferred definitions of the group $R^{21}$ are $C_{1-4}$-alkyl, $C_{1-4}$-alkylcarbonyl, $C_{1-4}$-alkylsulfonyl, —$SO_2$—$NH_2$, —$SO_2$—NH—$C_{1-3}$-alkyl, —$SO_2$—N($C_{1-3}$-alkyl)$_2$, and cyclo-$C_{3-6}$-alkyleneimino-sulfonyl, while, as hereinbefore defined, in each case one or more C atoms may additionally be mono- or polysubstituted by F and/or in each case one or two C atoms independently of one another may additionally be monosubstituted by Cl or Br.

Most particularly preferred meanings of $R^{21}$ are H, $C_{1-4}$-alkyl, $C_{1-4}$-alkylcarbonyl, $C_{1-4}$-alkoxycarbonyl, particularly H and $C_{1-3}$-alkyl.

Cy preferably denotes a $C_{3-7}$-cycloalkyl, particularly a $C_{3-6}$-cycloalkyl group, a $C_{5-7}$-cycloalkenyl group, pyrrolidinyl, piperidinyl, piperazinyl, morpholinyl, thiomorpholinyl, a phenyl ring to which a $C_{5-7}$-cycloalkyl or aza-$C_{4-7}$-cycloalkyl group is fused, aryl or heteroaryl, while aryl or heteroaryl preferably denotes a monocyclic or fused bicyclic ring system, and the abovementioned cyclic groups may be mono- or polysubstituted by $R^{20}$ at one or more C atoms, in the case of a phenyl group may also additionally be monosubstituted by nitro, and/or one or more NH groups may be substituted by $R^{21}$.

The term aryl preferably denotes phenyl or naphthyl, particularly phenyl.

The term heteroaryl preferably comprises pyridyl, indolyl, quinolinyl, and benzoxazolyl.

Preferred compounds according to the invention are those wherein one or more of the groups, radicals, substituents and/or indices have one of the meanings specified above as being preferred.

Particularly preferred compounds according to the invention are those wherein

Y has one of the following meanings

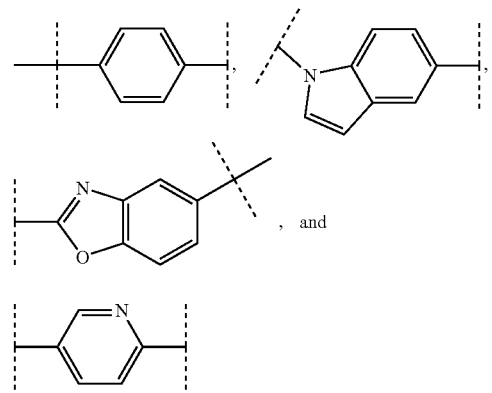

, and while the abovementioned cyclic groups may be mono- or polysubstituted by $R^{20}$ at one or more C atoms, and in the case of a phenyl ring may also additionally be monosubstituted by nitro, and/or A denotes phenyl or pyridyl, which may be mono- or polysubstituted by $R^{20}$, and may also additionally be monosubstituted by nitro, and/or B denotes phenyl which may be mono- or polysubstituted by $R^{20}$, and may also additionally be monosubstituted by nitro, and/or b has the value 0 or 1.

Most particularly preferred are those compounds according to the invention wherein A, B, b, X, Y, Z, $R^1$, $R^2$, $R^3$, $R^{5a}$, and $R^{5b}$ independently of one another have one or more of the preferred meanings mentioned above.

Preferred groups of compounds according to this invention can be described by the following formulae, particularly I.a, I.b, and I.c:

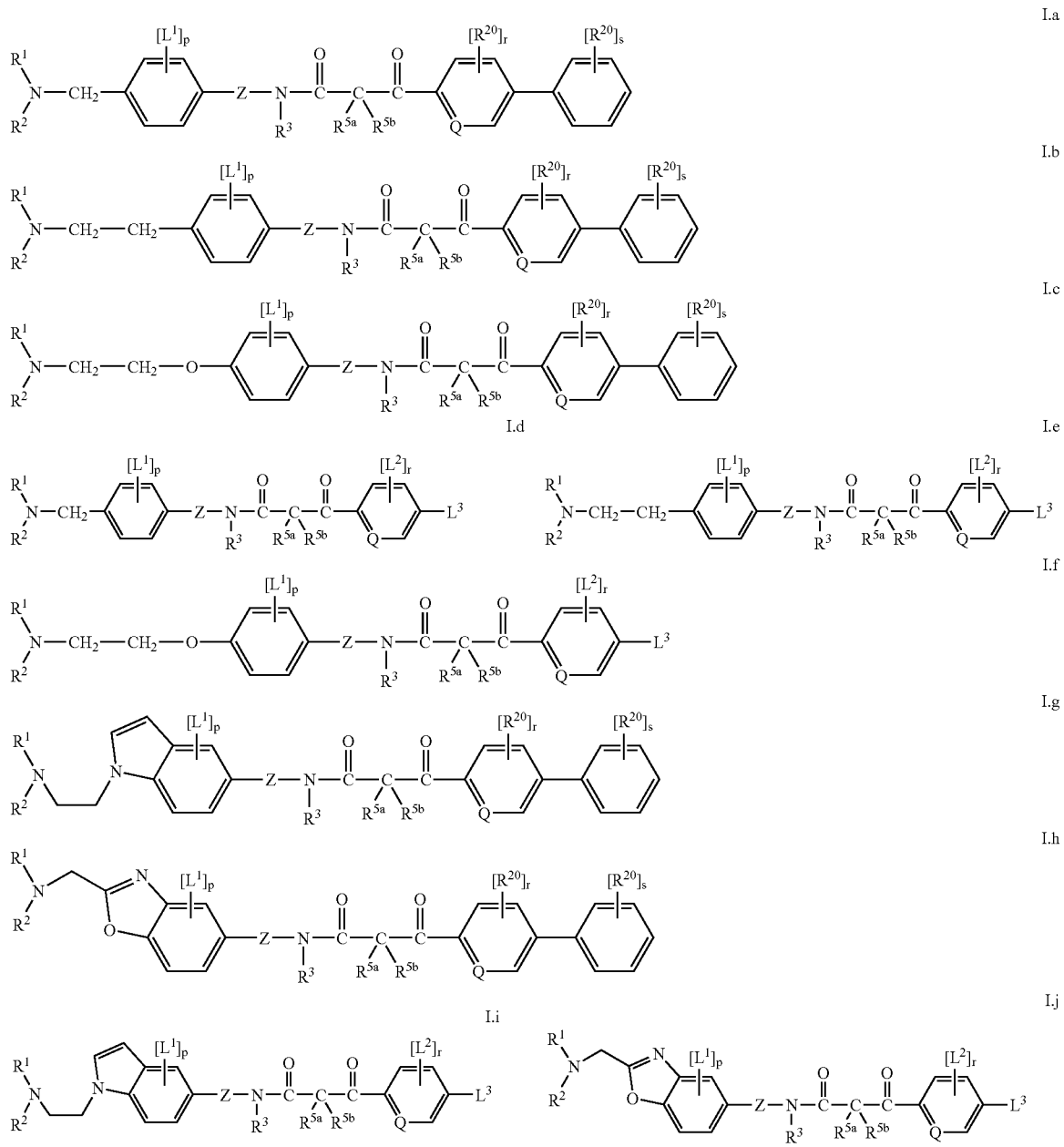

while the bridges X appearing in formulae I.a to I.j representing —$CH_2$—, —$CH_2$—$CH_2$—, and —$CH_2$—$CH_2$—O— may have one or two substituents independently of one another selected from among $C_{1-3}$-alkyl and $C_{3-5}$-cycloalkyl, while two alkyl substituents may be joined together, forming a $C_{3-6}$-cycloalkyl group; particularly preferably, the above-mentioned bridges X, particularly representing —$CH_2$—, may have one or two methyl substituents, while two methyl substituents may be joined together to form a cyclopropyl group; and $L^1$, $L^2$, $L^3$, $R^1$, $R^2$, $R^3$, $R^{5a}$, $R^{5b}$, and $R^{20}$ are as hereinbefore defined and substituents occurring several times may have the same or different meanings; particularly $R^1$ and $R^2$ independently of one another denote H, $C_{1-6}$-alkyl, $C_{3-7}$-cycloalkyl, $C_{3-7}$-cycloalkyl-$C_{1-3}$-alkyl, tetrahydropyran-3 or -4-yl, tetrahydropyranyl-$C_{1-3}$-alkyl, piperidin-3-yl or -4-yl, N—($C_{1-4}$-alkyl)-piperidin-3-yl or -4-yl, piperidinyl-$C_{1-3}$-alkyl, N—($C_{1-4}$-alkyl)-piperidinyl-$C_{1-3}$-alkyl, phenyl, pyridyl, phenyl-$C_{1-3}$-alkyl, pyridyl-$C_{1-3}$-alkyl, hydroxy-$C_{2-4}$-alkyl, $C_{1-4}$-alkoxy-$C_{2-4}$-alkyl, amino-$C_{2-4}$-alkyl, $C_{1-4}$-alkyl-amino-$C_{2-4}$-alkyl, or di-(($C_{1-4}$-alkyl)-amino-$C_{2-4}$-alkyl, while cycloalkyl rings may be mono-, di-, or trisubstituted by substituents selected from hydroxy, hydroxy-$C_{1-3}$-alkyl, $C_{1-3}$-alkyl, or $C_{1-3}$-alkyloxy, particularly hydroxy, hydroxymethyl, methyl, and methoxy, and $C_{2-4}$-alkyl bridges in the definitions hydroxy-$C_{2-4}$-alkyl and $C_{1-4}$-alkoxy-$C_{2-4}$-alkyl may additionally be monosubstituted by hydroxy, hydroxy-$C_{1-3}$-alkyl, $C_{1-3}$-alkyl, or $C_{1-3}$-alkyloxy, particularly hydroxy, hydroxymethyl, methyl, or methoxy, and alkyl groups may be monoor polysubstituted by F and/or monosubstituted by Cl; $R^1$, $R^2$ independently of one another denote methyl, ethyl, n-propyl, isopropyl, 2-hydroxyethyl, 2-hydroxy-propyl, 3-hydroxypropyl, 2-hydroxy-2-methyl-propyl, 2-methoxyethyl, 3-amino-propyl, propen-3-yl, propin-3-yl, cyclopropyl, cyclopentyl, cyclohexyl, cyclopropylmethyl, cyclopentylmethyl, (1-hydroxycyclopropyl)methyl, phenyl, pyridyl, phenylmethyl, pyridylmethyl, tetrahydropyran-4-yl, N-methyl-piperidin-4-yl, N-(methylcarbonyl)piperidin-4-yl, or N-(tert-butyloxycarbonyl)-piperidin-4-yl, while hydroxyalkyl groups may additionally be substituted by hydroxy, and one of the groups $R^1$ and $R^2$ may also represent H, or $R^1$ and $R^2$ are joined together such that the group

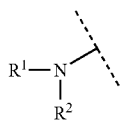

is defined according to one of the following partial formulae:

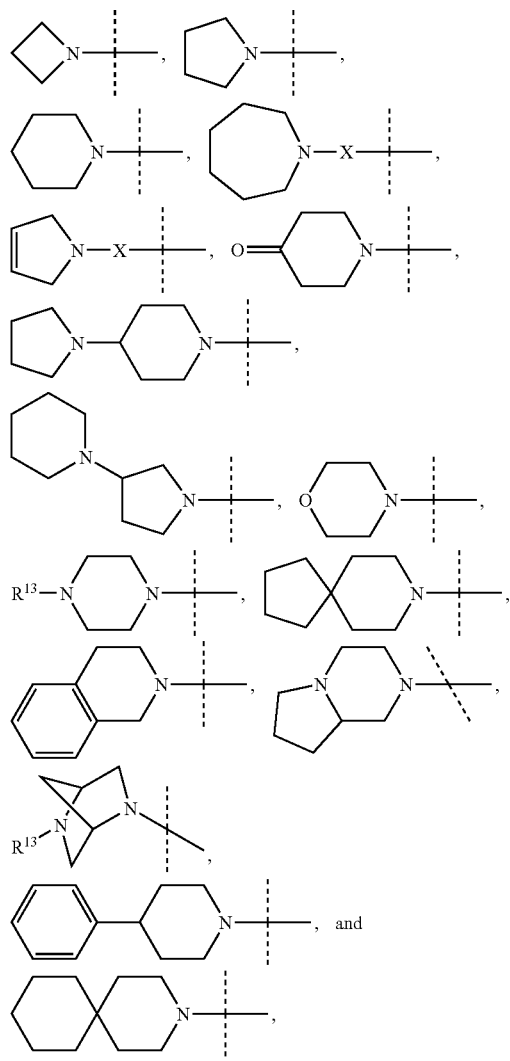

while in the heterocycle formed by the group $R^1R^2N$— one or more H atoms may be replaced by $R^{14}$ and/or a H atom may be replaced by Cy representing $C_{3-6}$-cycloalkyl, which may be mono- or polysubstituted by $R^{20}$, particularly by F, hydroxy, $C_{1-3}$-alkyl, $CF_3$, $C_{1-3}$-alkyloxy, $OCF_3$, or hydroxy-$C_{1-3}$-alkyl, particularly preferably by F, hydroxy, methyl, methoxy, $CF_3$, $OCF_3$, or hydroxymethyl, and the ring connected to the heterocycle formed by the group $R^1R^2N$— may be mono- or polysubstituted, preferably monosubstituted by $R^{20}$ at one or more C atoms, and in the case of a phenyl ring may also additionally be monosubstituted by nitro and $R^3$ preferably denotes H or methyl, $R^{14}$ in each case independently of one another denote F, Cl, $C_{1-4}$-alkyl, $C_{3-6}$-cycloalkyl-$C_{1-3}$-alkyl, hydroxy, hydroxy-$C_{1-3}$-alkyl, $C_{1-4}$-alkyloxy, $C_{1-4}$-alkoxy-$C_{1-3}$-alkyl, pyridylamino, or aminocarbonyl, while in each case one or more C atoms may additionally be mono- or polysubstituted by F or in each case a C atom may be monosubstituted by Cl; most particularly preferably denotes methyl, ethyl, propyl, trifluoromethyl, hydroxy, hydroxymethyl, 1-hydroxyethyl, 2-hydroxyethyl, 1-hydroxy-1-methyl-ethyl, methoxy, ethoxy, methoxymethyl, pyridylamino, or aminocarbonyl; and $R^{13}$ denotes H, $C_{1-4}$-alkyl, $C_{1-4}$-alkylcarbonyl, or $C_{1-4}$-alkyloxycarbonyl; particularly preferably denotes H or $C_{1-3}$-alkyl; and Q denotes CH or N, particularly denotes CH, while CH may be substituted by $R^{20}$, $L^1$, $L^2$, and $L^3$ in each case independently of one another have one of the meanings given previously for $R^{20}$, preferably denote fluorine, chlorine, bromine, cyano, $C_{1-3}$-alkyl, $C_{1-3}$-alkoxy, trifluoromethyl, trifluoromethoxy, or nitro, p has the value 0 or 1, r and s in each case independently of one another have the value 0, 1, 2, or 3, preferably 0, 1, or 2, particularly preferably 0 or 1, and Z, $R^{5a}$, $R^{5b}$, and $R^{20}$ are as hereinbefore defined and substituents occurring more than once may have the same or different meanings, and in particular Z denotes a single bond or —$CH_2$—$CH_2$—, particularly preferably a single bond, $R^{5a}$ and $R^{5b}$ independently of one another denote H, F, Cl, methyl or ethyl, particularly preferably H, $R^{20}$ in each case independently of one another preferably denote fluorine, chlorine, bromine, cyano, $C_{1-4}$-alkyl, $C_{2-6}$-alkenyl, hydroxy, hydroxy-$C_{1-3}$-alkyl, $C_{1-4}$-alkoxy, trifluoromethyl, trifluoromethoxy, $C_{2-4}$-alkynyl, carboxy, $C_{1-4}$-alkoxycarbonyl, $C_{1-4}$-alkoxy-$C_{1-3}$-alkyl, $C_{1-4}$-alkoxycarbonylamino, amino, $C_{1-4}$-alkyl-amino, di-($C_{1-4}$-alkyl)-amino, cyclo-$C_{3-6}$-alkyleneimino, aminocarbonyl, $C_{1-4}$-alkyl-amino-carbonyl and di-($C_{1-4}$-alkyl)-aminocarbonyl, particularly preferably $R^{20}$ is selected from fluorine, chlorine, bromine, cyano, nitro, $C_{1-4}$-alkyl, hydroxy, ω-hydroxy-$C_{1-3}$-alkyl, $C_{1-4}$-alkoxy, trifluoromethyl, trifluoromethoxy, $C_{2-4}$-alkynyl, carboxy, $C_{1-4}$-alkoxycarbonyl, and $C_{1-4}$-alkoxy-$C_{1-3}$-alkyl.

The compounds listed in the experimental section are preferred according to the invention. Some particularly preferred compounds are shown below:

| | |
|---|---|
| 33 | 34 |
A.1
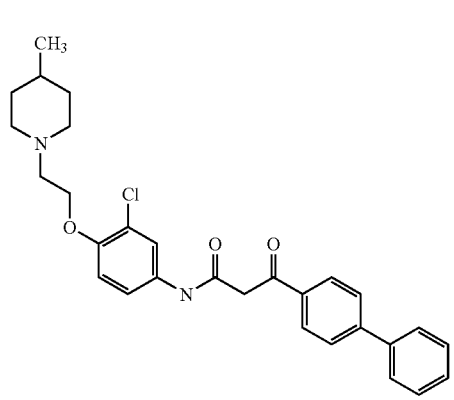
A.2
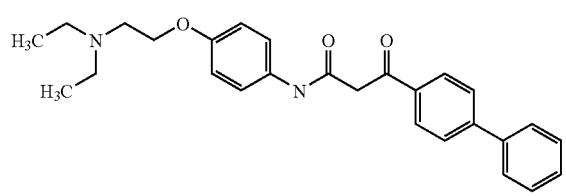
A.3
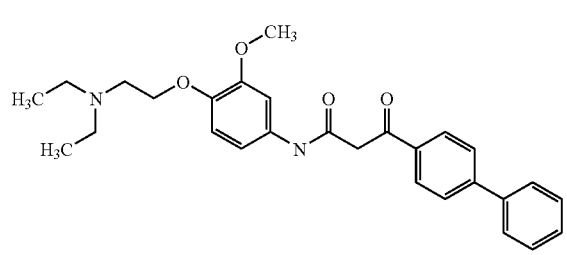
A.4
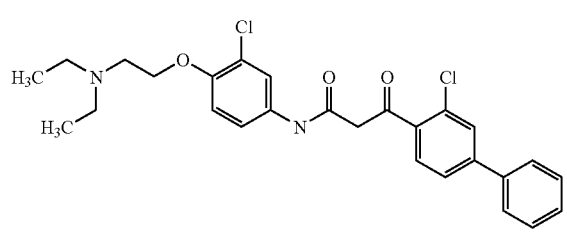
A.5
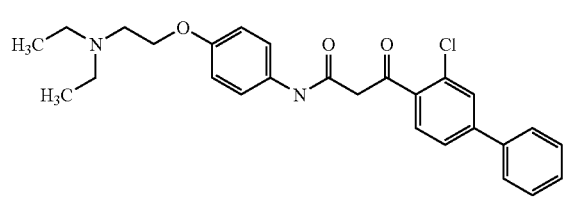
A.6
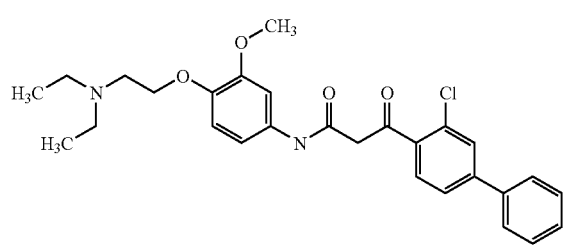
A.7
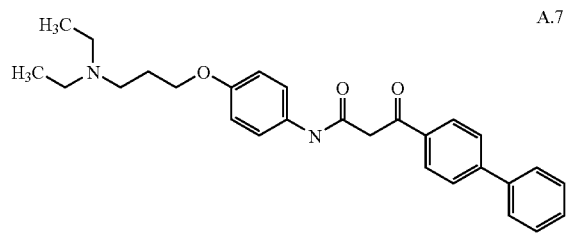
A.8
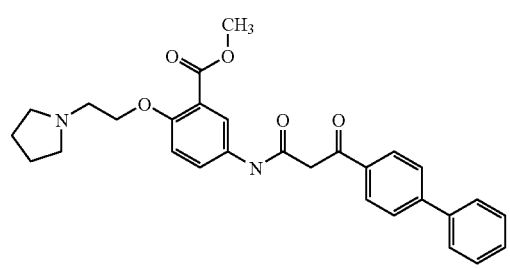
A.9
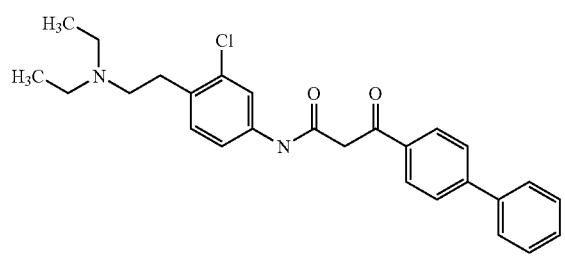
A.10
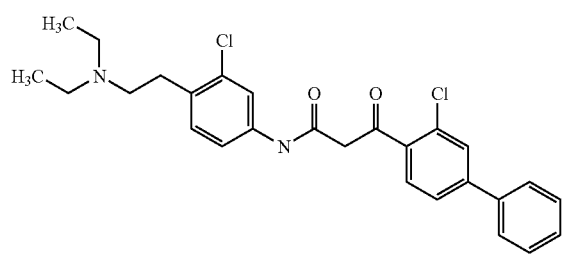

-continued
A.11
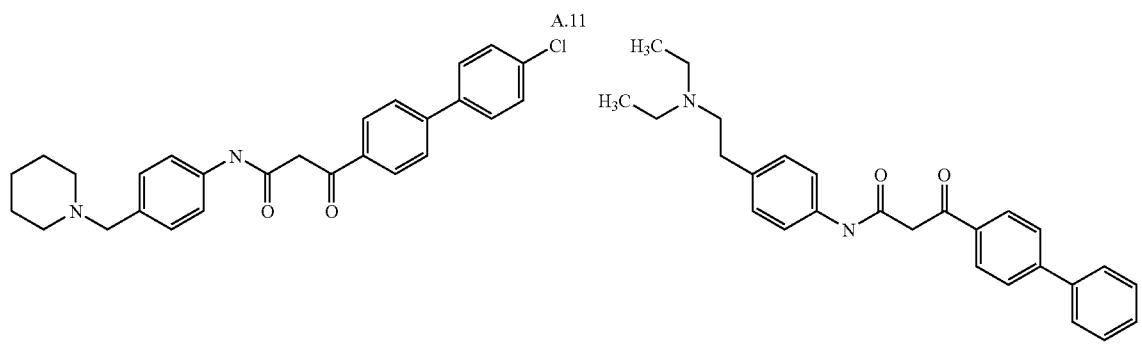
A.12
A.13
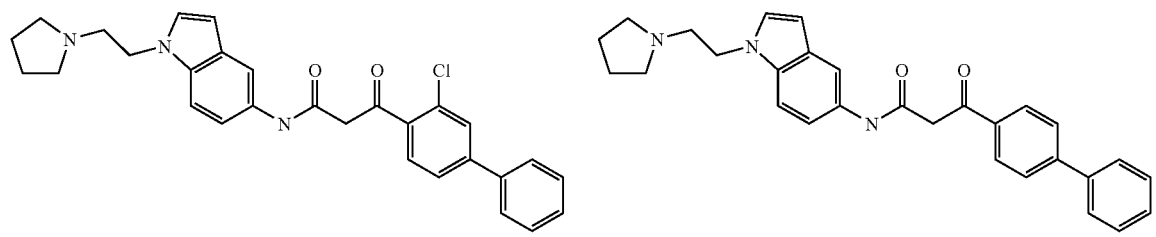
A.14
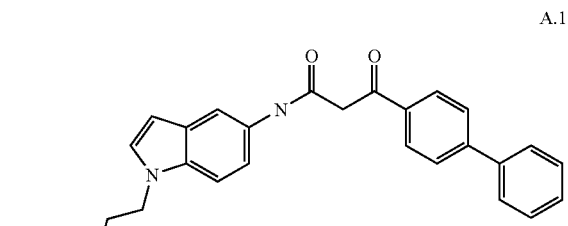
A.15
A.16
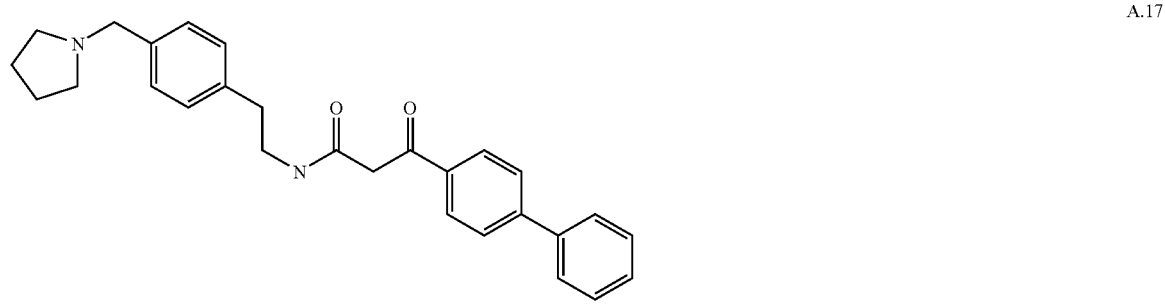
A.17
A.18
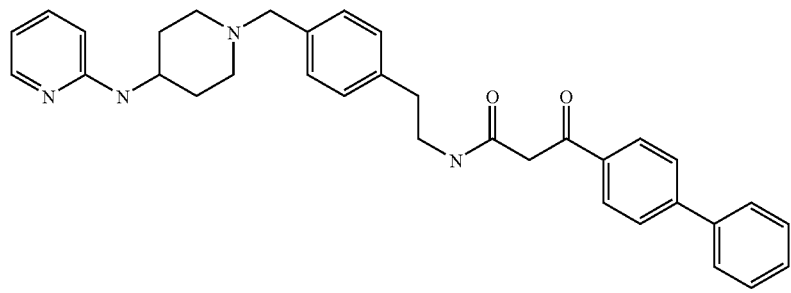

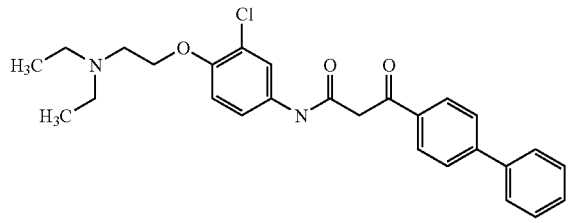

A.19

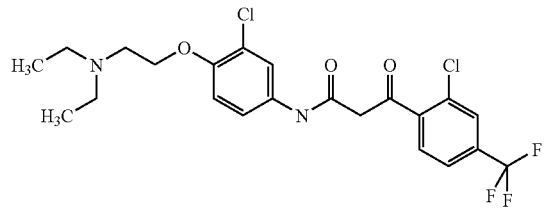

A.20

Some expressions used hereinbefore and below to describe the compounds according to the invention will now be defined more fully.

The term halogen denotes an atom selected from among F, Cl, Br, and I, particularly F, Cl, and Br.

The term $C_{1-n}$-alkyl, where n has a value of 3 to 8, denotes a saturated, branched or unbranched hydrocarbon group with 1 to n C atoms. Examples of such groups include methyl, ethyl, n-propyl, isopropyl, butyl, isobutyl, sec-butyl, tert-butyl, n-pentyl, isopentyl, neopentyl, tert-pentyl, n-hexyl, isohexyl, etc.

The term $C_{1-n}$-alkylene, where n may have a value of 1 to 8, denotes a saturated, branched or unbranched hydrocarbon bridge with 1 to n C atoms. Examples of such groups include methylene (—CH$_2$—), ethylene (—CH$_2$—CH$_2$—), 1-methylethylene (—CH(CH$_3$)—CH$_2$—), 1,1-dimethylethylene (—C(CH$_3$)$_2$—CH$_2$—), n-prop-1,3-ylene (—CH$_2$—CH$_2$—CH$_2$—), 1-methylprop-1,3-ylene (—CH(CH$_3$)—CH$_2$—CH$_2$—), 2-methylprop-1,3-ylene (—CH$_2$—CH(CH$_3$)—CH$_2$—), etc., as well as the corresponding mirror-symmetrical forms.

The term $C_{2-n}$-alkenyl, where n has a value of 3 to 6, denotes a branched or unbranched hydrocarbon group with 2 to n C atoms and at least one C═C-double bond. Examples of such groups include vinyl, 1-propenyl, 2-propenyl, isopropenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl etc.

The term $C_{2-n}$-alkynyl, where n has a value of 3 to 6, denotes a branched or unbranched hydrocarbon group with 2 to n C atoms and a C≡C triple bond. Examples of such groups include ethynyl, 1-propynyl, 2-propynyl, isopropynyl, 1-butynyl, 2-butynyl, 3-butynyl, 2-methyl-1-propynyl, 1-pentynyl, 2-pentynyl, 3-pentynyl, 4-pentynyl, 3-methyl-2-butynyl, 1-hexynyl, 2-hexynyl, 3-hexynyl, 4-hexynyl, 5-hexynyl, etc.

The term $C_{1-n}$-alkoxy denotes a $C_{1-n}$-alkyl-O— group, wherein $C_{1-n}$-alkyl is defined as above. Examples of such groups include methoxy, ethoxy, n-propoxy, isopropoxy, n-butoxy, isobutoxy, sec-butoxy, tert-butoxy, n-pentoxy, isopentoxy, neopentoxy, tert-pentoxy, n-hexoxy, isohexoxy etc.

The term $C_{1-n}$-alkylthio denotes a $C_{1-n}$-alkyl-S— group, wherein $C_{1-n}$-alkyl is defined as above. Examples of such groups include methylthio, ethylthio, n-propylthio, isopropylthio, n-butylthio, isobutylthio, sec-butylthio, tert-butylthio, n-pentylthio, isopentylthio, neopentylthio, tert-pentylthio, n-hexylthio, isohexylthio, etc.

The term $C_{1-n}$-alkylcarbonyl denotes a $C_{1-n}$-alkyl—C(═O)— group, wherein $C_{1-n}$-alkyl is defined as above. Examples of such groups include methylcarbonyl, ethylcarbonyl, n-propylcarbonyl, isopropylcarbonyl, n-butylcarbonyl, isobutylcarbonyl, sec-butylcarbonyl, tert-butylcarbonyl, n-pentylcarbonyl, isopentylcarbonyl, neopentylcarbonyl, n-pentylcarbonyl, n-hexylcarbonyl, isohexylcarbonyl, etc.

The term $C_{3-n}$-cycloalkyl denotes a saturated mono-, bi-, tri-, or spirocarbocyclic, preferably monocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term $C_{5-n}$-cycloalkenyl denotes a monounsaturated mono-, bi-, tri-, or spirocarbocyclic group with 5 to n C atoms. Examples of such groups include cyclopentenyl, cyclohexenyl, cycloheptenyl, cyclooctenyl, cyclononenyl, etc.

The term $C_{3-n}$-cycloalkylcarbonyl denotes a $C_{3-n}$-cycloalkyl-C(═O) group, wherein $C_{3-n}$-cycloalkyl is as hereinbefore defined.

The term aryl denotes a carbocyclic, aromatic ring system, such as, for example, phenyl, biphenyl, naphthyl, anthracenyl, phenanthrenyl, fluorenyl, indenyl, pentalenyl, azulenyl, biphenylenyl, etc. A particularly preferred meaning of "aryl" is phenyl.

The term cyclo-$C_{3-7}$-alkyleneimino denotes a 4- to 7-membered ring which comprises 3 to 7 methylene units as well as an imino group, while the bond to the residue of the molecule is made via the imino group.

The term cyclo-$C_{3-7}$-alkyleneimino-carbonyl denotes a cyclo-$C_{3-7}$-alkyleneimino ring as hereinbefore defined which is linked to a carbonyl group via the imino group.

The term heteroaryl used in this application denotes a heterocyclic, aromatic ring system which comprises in addition to at least one C atom one or more heteroatoms selected from N, O and/or S. Examples of such groups are furanyl, thiophenyl, pyrrolyl, oxazolyl, thiazolyl, imidazolyl, isoxazolyl, isothiazolyl, 1,2,3-triazolyl, 1,3,5-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuranyl, benzothiophenyl (thianaphthenyl), indazolyl, benzimidazolyl, benzthiazolyl, benzisothiazolyl, benzoxazolyl, benzisoxazolyl, purinyl, quinazolinyl, quinozilinyl, quinolinyl, isoquinolinyl, quinoxalinyl, naphthyridinyl, pteridinyl, carbazolyl, azepinyl, diazepinyl, acridinyl, etc. The term heteroaryl also comprises the partially hydrogenated heterocyclic, aromatic ring systems, particularly those listed above. Examples of such partially hydrogenated ring systems are 2,3-dihydrobenzofuranyl, pyrolinyl, pyrazolinyl, indolinyl, oxazolidinyl, oxazolinyl, oxazepinyl, etc. Particularly preferably heteroaryl denotes a heteroaromatic mono- or bicyclic ring system.

Terms such as $C_{3-7}$-cycloalkyl-$C_{1-n}$-alkyl, aryl-$C_{1-n}$-alkyl, heteroaryl-$C_{1-n}$-alkyl, etc. refer to $C_{1-n}$-alkyl, as defined above, which is substituted with a $C_{3-7}$-cycloalkyl, aryl or heteroaryl group.

Many of the terms given above may be used repeatedly in the definition of a formula or group and in each case have one of the meanings given above, independently of one another.

The term "unsaturated", for example, in "unsaturated carbocyclic group" or "unsaturated heterocyclic group", as used particularly in the definition of the group Cy, comprises, in addition to the mono- or polyunsaturated groups, the corresponding totally unsaturated groups, but particularly the mono- and diunsaturated groups.

The expression "optionally substituted" used in this application indicates that the group thus designated is either unsubstituted or mono- or polysubstituted by the substituents specified. If the group in question is polysubstituted, the substituents may be identical or different.

The style used hereinbefore and hereinafter, according to which in a cyclic group a bond of a substituent is shown towards the centre of this cyclic group, unless otherwise stated, indicates that this substituent may be bound to any free position of the cyclic group carrying an H atom.

Thus in the example

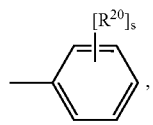

the substituent $R^{20}$ where s is 1 may be bound to any of the free positions of the phenyl ring; where s is 2, selected substituents $R^{20}$ may differently from one another be bound to different free positions of the phenyl ring.

The H atom of any carboxy group present or an H atom bound to an N atom (imino or amino group) may in each case be replaced by a group which can be cleaved in vivo. By a group which can be cleaved in vivo from an N atom is meant, for example, a hydroxy group, an acyl group such as the benzoyl or pyridinoyl group or a $C_{1-16}$-alkanoyl group such as the formyl, acetyl, propionyl, butanoyl, pentanoyl, or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert-butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl, or hexadecyloxycarbonyl group, a phenyl-$C_{1-6}$-alkoxycarbonyl group such as the benzyloxycarbonyl, phenylethoxycarbonyl, or phenylpropoxycarbonyl group, a $C_{1-3}$-alkylsulfonyl-$C_{2-4}$-alkoxycarbonyl, $C_{1-3}$-alkoxy-$C_{2-4}$-alkoxy-$C_{2-4}$-alkoxycarbonyl, or $R_eCO$—O—$(R_fCR_g)$—O—CO— group wherein $R_e$ denotes a $C_{1-8}$-alkyl, $C_{5-7}$-cycloalkyl, phenyl, or phenyl-$C_{1-3}$-alkyl group, $R_f$ denotes a hydrogen atom, a $C_{1-3}$-alkyl, $C_{5-7}$-cycloalkyl, or phenyl group, and $R_g$ denotes a hydrogen atom or a $C_{1-3}$-alkyl group, while the phthalimido group is an additional possibility for an amino group, and the abovementioned ester groups may also be used as a group which can be converted in vivo into a carboxy group.

The residues and substituents described above may be mono- or polysubstituted by fluorine as described. Preferred fluorinated alkyl groups are fluoromethyl, difluoromethyl, and trifluoromethyl. Preferred fluorinated alkoxy groups are fluoromethoxy, difluoromethoxy, and trifluoromethoxy. Preferred fluorinated alkylsulfinyl and alkylsulfonyl groups are trifluoromethylsulfinyl and trifluoromethylsulfonyl.

The compounds of general formula I according to the invention may have acid groups, predominantly carboxyl groups, and/or basic groups such as, e.g., amino functions. Compounds of general formula I may therefore be present as internal salts, as salts with pharmaceutically useable inorganic acids such as hydrochloric acid, sulfuric acid, phosphoric acid, sulfonic acid, or organic acids (such as, for example, maleic acid, fumaric acid, citric acid, tartaric acid, or acetic acid) or as salts with pharmaceutically useable bases such as alkali or alkaline earth metal hydroxides or carbonates, zinc or ammonium hydroxides or organic amines such as, e.g., diethylamine, triethylamine, triethanolamine inter alia.

The compounds according to the invention may be obtained using methods of synthesis which are known in principle. Preferably the compounds are obtained analogously to the methods of preparation explained more fully hereinafter, which are also an object of this invention. The abbreviations used hereinafter are defined in the introduction to the experimental section or are already familiar to those skilled in the art.

If the starting materials or intermediate products listed below contain groups $R^1$, $R^2$, $R^3$, X, Y, Z, A, or B with amine functions, these are preferably used in protected form, for example, with a Boc, Fmoc, or Cbz protective group, and liberated at the end of the reactions using standard methods.

Synthesis Plan A:

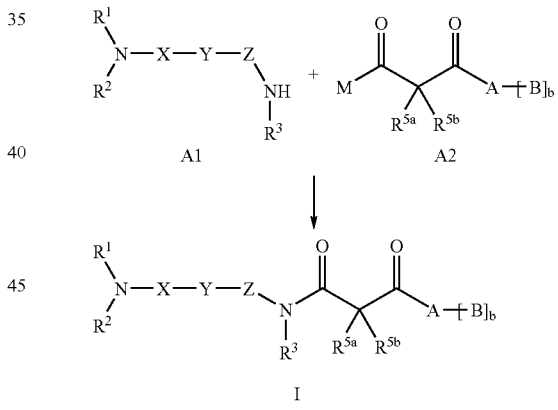

Compounds of formula I according to the invention are obtained according to Synthesis Plan A by reacting an amine of formula A1 with a carboxylic acid or a carboxylic acid derivative of formula A2 using amide synthesis methods known in the art. In the carboxylic acid derivative A2 the group M preferably has a meaning selected from OH, Cl, $C_{1-6}$-alkoxy, $C_{1-6}$-alkylthio, $C_{1-6}$-alkyl-COO, etc.

Preferably the carboxylic acid compound of formula A2 (M is OH) is reacted with at least one peptide coupling reagent, such as, for example, TBTU, in a solvent or mixture of solvents and then the reaction mixture is further reacted with the amine compound of formula A1, while the minimum of one base is added to the reaction mixture before and/or after the reaction of the carboxylic acid compound with TBTU. The peptide coupling reagent, such as TBTU, is advantageously used in an equimolar amount or in an excess relative to the carboxylic acid A2, preferably from equimolar to a 50 mol % excess. Alternatively the reaction may also be carried out in the presence of an amount of HOBt which is equimolar to the TBTU. Advantageously the carboxylic acid of formula A2 is used with TBTU and then this reaction mixture is used with the amine compound of formula A1 in a molar ratio of the carboxylic acid compound of formula A2:amine compound of formula A1:TBTU:base of 1±0.25: 1±0.25:1±0.25:1 to 4.

Instead of a carboxylic acid it is also possible to use the corresponding activated carboxylic acid derivatives, such as, for example, esters, orthoesters, or carboxylic acid chlorides or anhydrides.

Suitable bases are, in particular, tertiary amines such as triethylamine or Hünig base as well as alkali metal carbonates, for example, potassium carbonate. The reactions take place in a suitable solvent or mixture of solvents, while DMF and/or THF is preferably used. The carboxylic acid or the carboxylic acid derivative (A2) and the amine (A1) are preferably used in a molar ratio of 1.5:1 to 1:1.5. The reaction is advantageously carried out over a period of from 1 to 24 hours in a temperature range from 0° C. to 120° C., preferably 20° C. to 80° C.

If activation of the carboxylic acid compound A2 (M is OH) is desired, this can advantageously be done using a mixed anhydride. The mixed anhydride of the carboxylic acid A2 in question is preferably prepared by reacting the carboxylic acid with an excess of alkyl chloroformate, preferably isopropyl chloroformate, in a molar ratio of 1:1 to 1:1.2. Suitable bases are preferably tertiary amines, for example, N-methylmorpholines, which are used in an equimolar amount to the alkyl chloroformate in question.

The reaction is carried out in a suitable solvent such as THF at temperatures between −20° C. and 20° C., particularly −15° C. to 0° C., and takes place over a period of 10 to 2400 minutes.

The mixed anhydride thus obtained is preferably reacted with an amine compound (A1) without further purification. The amine compound (A1) is used in an excess relative to the carboxylic acid derivative (A2) in question, preferably in a 5-10 mol % excess. The reaction is carried out, for example, at 0° C. to 60° C. over a period of 1 to 4 hours.

Synthesis Plan B1:

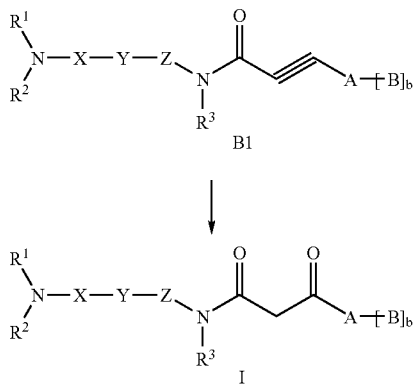

Alternatively compounds of formula I according to the invention may be obtained according to Synthesis Plan B1 by hydrolysis of the triple bond of the propynoic acid amides of formula B1. The hydrolysis of the propynoic acid amides to form the corresponding β-ketoamide is carried out by the addition of an acid or base and optionally in the presence of an activating nucleophile. Suitable acids for this purpose are particularly strong inorganic or organic acids, such as, for example, hydrochloric acid, sulfuric acid, acetic acid, formic acid, oxalic acid, methanesulfonic acid, or trifluoromethanesulfonic acid. Suitable bases are particularly alkali metal hydroxides, carbonates, or acetates, such as, for example, potassium hydroxide, sodium hydroxide, lithium hydroxide, sodium acetate, or potassium carbonate, or aqueous solutions of secondary or tertiary amines, such as, for example, triethylamine, piperidine, morpholine, diisopropylethylamine, or diethylamine.

The acid or base is advantageously used in a molar excess compared with the propynoic acid amide.

Examples of suitable activating nucleophiles include in particular secondary amines, such as, for example, piperidine, morpholine, or diethylamines or thiols, such as, for example, ethanethiol or thiophenol, or phosphines such as, for example, triphenylphosphine or tributylphosphine.

The reaction is advantageously carried out in a suitable solvent or mixture of solvents, possibly in alcohols, such as, for example, in ethanol, or in acetone, dimethylformamide, dimethylsulfoxide, or acetonitrile, optionally in each case with the addition of small amounts of water, particularly less than or equal to 10 vol-% based on the volume of solvent, at temperatures between 20° C. and 120° C., preferably in the region of the boiling temperature of the solvent. Suitable reaction times are usually in the range from 1 to 24 hours.

Synthesis Plan B2:

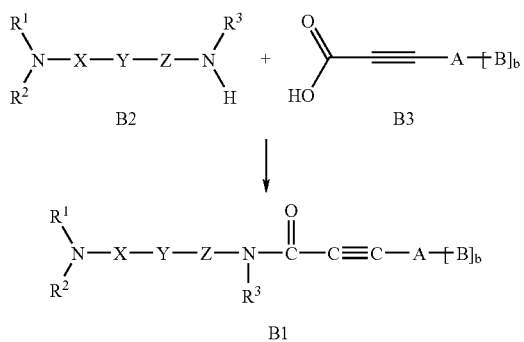

Compounds of formula B1 may be obtained by reacting an amine compound of general formula B2 with a propynoic acid compound of general formula B3 in an organic solvent such as, for example, DMF, THF, dioxane, acetonitrile, or toluene in the presence of a base such as, for example, triethylamine and activating reagents such as, for example, CDI, TBTU, or DCC. Instead of the compound B3 it is also possible to use the carboxylic acid chloride or a mixed anhydride of compound B3. The amide linking process described in connection with Synthesis Plan A may also be used here.

Synthesis Plan B3:

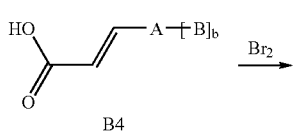

-continued

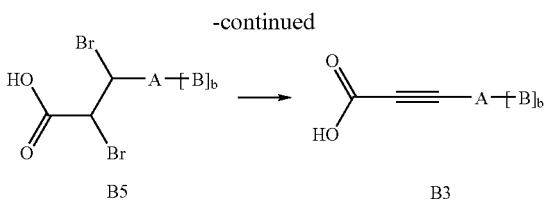

B5           B3

A compound of general formula B3 may also be prepared by reacting a compound of general formula B5 in an organic solvent such as, for example, dioxane, ethanol, or THF, with or without the addition of water, with a base such as potassium tert-butoxide, sodium hydroxide, or sodium ethoxide at temperatures from 0° C. to 150° C. However, it is also possible for this reaction to react a compound of general formula B5 with pyridine or quinoline at temperatures from 0° C. to 150° C. A compound of general formula B5 is obtained by brominating a compound of general formula B4 in a solvent such as, for example, carbon tetrachloride at temperatures between −20° C. to 100° C., preferably at temperatures between 0° C. and ambient temperature.

The compounds according to the invention may advantageously also be obtained by the methods described in the following Examples, which may also be combined with methods known to the skilled man from the literature, for example.

Stereoisomeric compounds of formula (I) may chiefly be separated by conventional methods. The diastereomers are separated on the basis of their different physico-chemical properties, e.g., by fractional crystallization from suitable solvents, by high pressure liquid or column chromatography, using chiral or preferably non-chiral stationary phases.

Racemates covered by general formula (I) may be separated, for example, by HPLC on suitable chiral stationary phases (e.g., Chiral-AGP or CHIRALPAK® AD). Racemates which contain a basic or acidic function can also be separated via the diastereomeric, optically active salts which are produced on reacting with an optically active acid, for example, (+)- or (−)-tartaric acid, (+)- or (−)-diacetyl tartaric acid, (+)- or (−)-monomethyl tartrate, or (+)-camphorsulfonic acid, or an optically active base, for example, with (R)-(+)-1-phenylethylamine, (S)-(−)-1-phenylethylamine, or (S)-brucine.

According to a conventional method of separating isomers, the racemate of a compound of general formula (I) is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example, in a ratio by volume of 50:50, are used. Then each of the optically active salts is dissolved in water, carefully neutralized with a base such as sodium carbonate or potassium carbonate, or with a suitable acid, e.g., with dilute hydrochloric acid or aqueous methanesulfonic acid and in this way the corresponding free compound is obtained in the (+) or (−) form.

The (R)- or (S)-enantiomer alone or a mixture of two optically active diastereomeric compounds covered by general formula I may also be obtained by performing the syntheses described above with a suitable reaction component in the (R)- or (S)-configuration.

As already mentioned, the compounds of formula (I) may be converted into the salts thereof, particularly for pharmaceutical use into the physiologically and pharmacologically acceptable salts thereof. These salts may be present on the one hand as physiologically and pharmacologically acceptable acid addition salts of the compounds of formula (I) with inorganic or organic acids. On the other hand, in the case of acidically bound hydrogen, the compound of formula (I) may also be converted by reaction with inorganic bases into physiologically and pharmacologically acceptable salts with alkali or alkaline earth metal cations as counter-ion. The acid addition salts may be prepared, for example, using hydrochloric acid, hydrobromic acid, sulfuric acid, phosphoric acid, methanesulfonic acid, ethanesulfonic acid, toluenesulfonic acid, benzenesulfonic acid, acetic acid, fumaric acid, succinic acid, lactic acid, citric acid, tartaric acid, or maleic acid. Moreover, mixtures of the above mentioned acids may be used. To prepare the alkali and alkaline earth metal salts of the compound of formula (I) with acidically bound hydrogen the alkali and alkaline earth metal hydroxides and hydrides are preferably used, while the hydroxides and hydrides of the alkali metals, particularly of sodium and potassium, are preferred and sodium and potassium hydroxide are most preferred.

The compounds according to the present invention, including the physiologically acceptable salts, are effective as antagonists of the MCH receptor, particularly the MCH-1 receptor, and exhibit good affinity in MCH receptor binding studies. Pharmacological test systems for MCH-antagonistic properties are described in the following experimental section.

As antagonists of the MCH receptor the compounds according to the invention are advantageously suitable as pharmaceutical active substances for the prevention and/or treatment of symptoms and/or diseases caused by MCH or causally connected with MCH in some other way. Generally the compounds according to the invention have low toxicity, they are well absorbed by oral route and have good intracerebral transitivity, particularly brain accessibility.

Therefore, MCH antagonists which contain at least one compound according to the invention are particularly suitable in mammals, such as, for example, rats, mice, guinea pigs, hares, dogs, cats, sheep, horses, pigs, cattle, monkeys, and humans, for the treatment and/or prevention of symptoms and/or diseases which are caused by MCH or are otherwise causally connected with MCH.

Diseases caused by MCH or otherwise causally connected with MCH are particularly metabolic disorders, such as, for example, obesity, and eating disorders, such as, for example, bulimia, including bulimia nervosa. The indication obesity includes in particular exogenic obesity, hyperinsulinemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity, central obesity. This range of indications also includes cachexia, anorexia, and hyperphagia.

Compounds according to the invention may be particularly suitable for reducing hunger, curbing appetite, controlling eating behaviour and/or inducing a feeling of satiation.

In addition, the diseases caused by MCH or otherwise causally connected with MCH also include hyperlipidemia, cellulitis, fatty accumulation, malignant mastocytosis, systemic mastocytosis, emotional disorders, affectivity disorders, depression, anxiety states, reproductive disorders, sexual disorders, memory disorders, epilepsy, forms of dementia, and hormonal disorders.

Compounds according to the invention are also suitable as active substances for the prevention and/or treatment of other illnesses and/or disorders, particularly those which accompany obesity, such as, for example, diabetes, diabetes mellitus, particularly type II diabetes, hyperglycemia, particularly chronic hyperglycemia, complications of diabetes including diabetic retinopathy, diabetic neuropathy, diabetic nephropathy, etc., insulin resistance, pathological glucose tolerance, encephalorrhagia, cardiac insufficiency, cardiovascular diseases, particularly arteriosclerosis and high blood pressure, arthritis, and gonitis.

MCH antagonists and formulations according to the invention may advantageously be used in combination with a dietary therapy, such as, for example, a dietary diabetes treatment, and exercise.

Another range of indications for which the compounds according to the invention are advantageously suitable is the prevention and/or treatment of micturition disorders, such as, for example, urinary incontinence, hyperactive bladder, urgency, nycturia, and enuresis, while the hyperactive bladder and urgency may or may not be connected with benign prostatic hyperplasia.

Generally speaking, the compounds according to the invention are potentially suitable for preventing and/or treating dependencies, such as, for example, alcohol and/or nicotine dependency, and/or withdrawal symptoms, such as, for example, weight gain in smokers coming off nicotine. By "dependency" it is generally meant here an irresistible urge to take an addictive substance and/or to perform certain actions, particularly in order to either achieve a feeling of wellbeing or to eliminate negative emotions. In particular, the term "dependency" is used here to denote a dependency on an addictive substance. By "withdrawal symptoms" are meant here, in general, symptoms which occur or may occur when addictive substances are withdrawn from patients dependent on one or more such substances. The compounds according to the invention are potentially suitable particularly as active substances for reducing or ending tobacco consumption, for the treatment or prevention of a nicotine dependency and/or for the treatment or prevention of nicotine withdrawal symptoms, for reducing the craving for tobacco and/or nicotine and generally as an anti-smoking agent. The compounds according to the invention may also be useful for preventing or at least reducing the weight gain typically seen when smokers are coming off nicotine. The substances may also be suitable as active substances which prevent or at least reduce the craving for and/or relapse into a dependency on addictive substances. The term addictive substances refers particularly but not exclusively to substances with a psycho-motor activity, such as narcotics or drugs, particularly alcohol, nicotine, cocaine, amphetamine, opiates, benzodiazepines, and barbiturates.

The dosage required to achieve such an effect is conveniently, by intravenous or sub-cutaneous route, 0.001 to 30 mg/kg of body weight, preferably 0.01 to 5 mg/kg of body weight, and by oral or nasal route or by inhalation, 0.01 to 50 mg/kg of body weight, preferably 0.1 to 30 mg/kg of body weight, in each case 1× to 3× daily.

For this purpose, the compounds of formula I prepared according to the invention may be formulated, optionally in conjunction with other active substances as described hereinafter, together with one or more inert conventional carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose, or fatty substances such as hard fat or suitable mixtures thereof, to produce conventional galenic preparations such as plain or coated tablets, capsules, lozenges, powders, granules, solutions, emulsions, syrups, aerosols for inhalation, ointments, or suppositories.

In addition to pharmaceutical compositions the invention also includes compositions containing at least one amide compound according to the invention and/or a salt according to the invention optionally together with one or more physiologically acceptable excipients. Such compositions may also be, for example, foodstuffs which may be solid or liquid, in which the compound according to the invention is incorporated.

For the above mentioned combinations it is possible to use as additional active substances particularly those which, for example, potentiate the therapeutic effect of an MCH antagonist according to the invention in terms of one of the indications mentioned above and/or which make it possible to reduce the dosage of an MCH antagonist according to the invention. Preferably one or more additional active substances are selected from among active substances for the treatment of diabetes, active substances for the treatment of diabetic complications, active substances for the treatment of obesity, preferably other than MCH antagonists, active substances for the treatment of high blood pressure, active substances for the treatment of hyperlipidemia, including arteriosclerosis, active substances for the treatment of dyslipidemia, including arteriosclerosis, active substances for the treatment of arthritis, active substances for the treatment of anxiety states, and active substances for the treatment of depression.

The above mentioned categories of active substances will now be explained in more detail by means of examples.

Examples of active substances for the treatment of diabetes are insulin sensitizers, insulin secretion accelerators, biguanides, insulins, α-glucosidase inhibitors, and $\beta_3$ adrenoreceptor agonists.

Insulin sensitizers include glitazones, particularly pioglitazone and its salts (preferably hydrochloride), troglitazone, rosiglitazone and its salts (preferably maleate), JTT-501, GI-262570, MCC-555, YM-440, DRF-2593, BM-13-1258, KRP-297, R-119702, and GW-1929.

Insulin secretion accelerators include sulfonylureas, such as, for example, tolbutamide, chloropropamide, tolazamide, acetohexamide, glyclopyramide and its ammonium salts, glibenclamide, gliclazide, and glimepiride. Further examples of insulin secretion accelerators are repaglinide, nateglinide, mitiglinide (KAD-1229), and JTT-608.

Biguanides include metformin, buformin, and phenformin.

Insulins include those obtained from animals, particularly cattle or pigs, semisynthetic human insulins which are synthesized enzymatically from insulin obtained from animals, human insulin obtained by genetic engineering, e.g., from *Escherichia coli* or yeasts. Moreover, the term insulin also includes insulin-zinc (containing 0.45 to 0.9 percent by weight of zinc) and protamine-insulin-zinc obtainable from zinc chloride, protamine sulfate, and insulin. Insulin may also be obtained from insulin fragments or derivatives (for example INS-1, etc.). Insulin may also include different kinds, e.g., with regard to the onset time and duration of effect ("ultra immediate action type", "immediate action type", "two phase type", "intermediate type", "prolonged action type", etc.), which are selected depending on the pathological condition of the patient.

α-Glucosidase inhibitors include acarbose, voglibose, miglitol, and emiglitate.

$\beta_3$ Adrenoreceptor agonists include AJ-9677, BMS-196085, SB-226552, and AZ40140.

Active substances for the treatment of diabetes other than those mentioned above include ergoset, pramlintide, leptin, BAY-27-9955 as well as glycogen phosphorylase inhibitors, sorbitol dehydrogenase inhibitors, protein tyrosine phosphatase 1B inhibitors, dipeptidyl protease inhibitors, glipazide, and glyburide.

Active substances for the treatment of diabetic complications include, for example, aldose reductase inhibitors, glycation inhibitors and protein kinase C inhibitors, DPP-IV blockers, GLP-1 or GLP-2 analogues, and SGLT-2 inhibitors.

Aldose reductase inhibitors are, for example, tolrestat, epalrestat, imirestat, zenarestat, SNK-860, zopolrestat, ARI-50i, and AS-3201.

An example of a glycation inhibitor is pimagedine.

Protein Kinase C inhibitors are, for example, NGF and LY-333531.

DPP-IV blockers are, for example, LAF237 (Novartis), MK431 (Merck) as well as 815541, 823093, and 825964 (all GlaxoSmithkline).

GLP-1 analogues are, for example, liraglutide (NN2211) (NovoNordisk), CJC1131 (Conjuchem), and exenatide (Amylin).

SGLT-2 inhibitors are, for example, AVE-2268 (Aventis) and T-1095 (Tanabe, Johnson & Johnson).

Active substances other than those mentioned above for the treatment of diabetic complications include alprostadil, thiapride hydrochloride, cilostazol, mexiletine hydrochloride, ethyl eicosapentate, memantine, and pimagedine (ALT-711).

Active substances for the treatment of obesity, preferably other than MCH antagonists, include lipase inhibitors and anorectics.

A preferred example of a lipase inhibitor is orlistat.

Examples of preferred anorectics are phentermine, mazindol, fluoxetine, sibutramine, baiamine, (S)-sibutramine, SR-141716, and NGD-95-1.

Active substances other than those mentioned above for the treatment of obesity include lipstatin.

Moreover for the purposes of this application the active substance group of anti-obesity active substances also includes the anorectics, of which the $\beta_3$ agonists, thyromimetic active substances and NPY antagonists should be emphasized. The range of substances which may be considered as preferred anti-obesity or anorectic active substances is indicated by the following additional list, by way of example: phenylpropanolamine, ephedrine, pseudoephedrine, phentermine, a cholecystokinin-A (hereinafter referred to as CCK-A) agonist, a monoamine reuptake inhibitor (such as, for example, sibutramine), a sympathomimetic active substance, a serotonergic active substance (such as, for example, dexfenfluramine, fenfluramine, a 5-HT2C agonist such as BVT.933 or APD356), a dopamine antagonist (such as, for example, bromocriptine or pramipexole), a melanocyte-stimulating hormone receptor agonist or mimetic, an analogue of melanocyte-stimulating hormone, a cannabinoid receptor antagonist (ACOMPLIA® (rimonabant)), an MCH antagonist, the OB protein (hereinafter referred to as leptin), a leptin analogue, a fatty acid synthase (FAS) antagonist, a leptin receptor agonist, a galanine antagonist, a GI lipase inhibitor or reducer (such as, for example, orlistat). Other anorectics include bombesin agonists, dehydroepiandrosterone or its analogues, glucocorticoid receptor agonists and antagonists, orexin receptor antagonists, urocortin binding protein antagonists, agonists of the Glucagon-like Peptide-1 receptor, such as, for example, exendin, AC 2993, CJC-1131, ZP10, or GRT0203Y, DPP-IV inhibitors, and ciliary neurotrophic factors, such as, for example, axokines. In this context mention should also be made of the forms of therapy which produce weight loss by increasing the fatty acid oxidation in the peripheral tissue, such as, for example, inhibitors of acetyl-CoA carboxylase.

Active substances for the treatment of high blood pressure include inhibitors of angiotensin converting enzyme, calcium antagonists, potassium channel openers, and angiotensin II antagonists.

Inhibitors of angiotensin converting enzyme include captopril, enalapril, alacepril, delapril (hydrochloride), lisinopril, imidapril, benazepril, cilazapril, temocapril, trandolapril, and manidipine (hydrochloride).

Examples of calcium antagonists are nifedipine, amlodipine, efonidipine, and nicardipine.

Potassium channel openers include levcromakalim, L-27152, AL0671, and NIP-121.

Angiotensin II antagonists include telmisartan, losartan, candesartan cilexetil, valsartan, irbesartan, CS-866, and E4177.

Active substances for the treatment of hyperlipidemia, including arteriosclerosis, include HMG-CoA reductase inhibitors and fibrate compounds.

HMG-CoA reductase inhibitors include pravastatin, simvastatin, lovastatin, atorvastatin, fluvastatin, lipantil, cerivastatin, itavastatin, ZD-4522, and their salts.

Fibrate compounds include bezafibrate, clinofibrate, clofibrate, and simfibrate.

Active substances for the treatment of dyslipidemia, including arteriosclerosis, include e.g., medicaments which raise the HDL level, such as, e.g., nicotinic acid and derivatives and preparations thereof, such as, e.g., niaspan, as well as agonists of the nicotinic acid receptor.

Active substances for the treatment of arthritis include NSAIDs (non-steroidal anti-inflammatory drugs), particularly COX-2 inhibitors, such as, for example, meloxicam or ibuprofen.

Active substances for the treatment of anxiety states include chlordiazepoxide, diazepam, oxozolam, medazepam, cloxazolam, bromazepam, lorazepam, alprazolam, and fludiazepam.

Active substances for the treatment of depression include fluoxetine, fluvoxamine, imipramine, paroxetine, and sertraline.

The dosage for these active substances is conveniently 1/5 of the lowest normal recommended dose up to 1/1 of the normal recommended dose.

In another embodiment the invention also relates to the use of at least one amide compound according to the invention and/or a salt according to the invention for influencing the eating behaviour of a mammal. This use is particularly based on the fact that compounds according to the invention may be suitable for reducing hunger, curbing appetite, controlling eating behaviour and/or inducing a feeling of satiety. The eating behaviour is advantageously influenced so as to reduce food intake. Therefore, the compounds according to the invention are advantageously used for reducing body weight. Another use according to the invention is the prevention of increases in body weight, for example, in people who had previously taken steps to lose weight and are interested in maintaining their lower body weight. According to this embodiment it is preferably a non-therapeutic use. Such a non-therapeutic use might be a cosmetic use, for example, to alter the external appearance, or an application to improve general health. The compounds according to the invention are preferably used non-therapeutically for mammals, particularly humans, not suffering from any diagnosed eating disorders, no diagnosed obesity, bulimia, diabetes and/or no diagnosed micturition disorders, particularly urinary incontinence. Preferably, the compounds according to the invention are suitable for non-therapeutic use in people whose BMI (body mass index), defined as their body weight in kilograms divided by their height (in meters) squared, is below a level of 30, particularly below 25.

The Examples that follow are intended to illustrate the invention.

Preliminary Remarks

As a rule, IR, $^1$H-NMR and/or mass spectra have been obtained for the compounds prepared. Unless otherwise stated the $R_f$ values were determined using ready-made silica gel 60 TLC plates $F_{254}$ (E. Merck, Darmstadt, Item No. 1.05714) without chamber saturation. The $R_f$ values obtained under the heading Alox were determined using ready-made aluminum oxide 60 TLC plates $F_{254}$ (E. Merck, Darmstadt, Item No. 1.05713) without chamber saturation. The ratios specified for the eluants are based on units by volume of the solvents in question. The units by volume specified in the case of $NH_3$ relate to a concentrated solution of $NH_3$ in water. For chromatographic purification, silica gel made by Messrs Millipore (MATREX™, 35-70 my) is used. For chromatographic purification, Alox (E. Merck, Darmstadt, standardized aluminum oxide 90, 63-200 μm, Item No. 1.01097.9050) is used.

The following abbreviations for the eluant mixtures are used hereinafter when giving the $R_f$ values:

(A): silica gel, methylene chloride/methanol/ammonia (9:1:0.01)

(B): silica gel, methylene chloride/methanol/ammonia (5:1:0.01)

(C): silica gel, methylene chloride/methanol (9:1)

(D): silica gel, methylene chloride/methanol/ammonia (9:1:0.1)

(E): aluminum oxide, methylene chloride/methanol (30:1)

If there is no specific information as to the configuration, it is not clear whether there are pure enantiomers or whether partial or even total racemization has taken place.

The following abbreviations are used above and hereinafter:

abs. absolute

Cbz benzyloxycarbonyl

DMF N,N-dimethylformamide

EII electron impact ionization ether diethyl ether

EtOAc ethyl acetate

EtOH ethanol

Fmoc 9-fluorenylmethoxycarbonyl

MeOH methanol

Ph phenyl

RT ambient (room) temperature

TBTU 2-(1H-benzotriazol-1-yl)-1,1,3,3-tetramethyluronium tetrafluoroborate

THF tetrahydrofuran

Preparation of the Starting Compounds

Example I.1

Ethyl 3-biphenyl-4-yl-3-oxopropionate

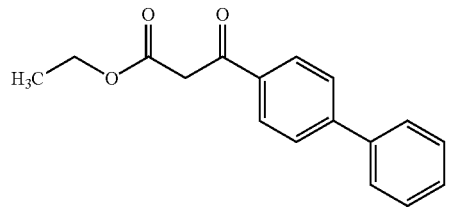

14.7 g (75.0 mmol) of 4-acetylbiphenyl is dissolved in 150 mL of diethylcarbonate. Under protective gas, a total of 6.50 g (150 mmol) sodium hydride in oil (55%) is added batchwise at 0° C. The mixture is kept for 5 minutes at 0° C., then stirred for 2 hours at 80° C. After cooling, the mixture is poured onto water and extracted with methylene chloride; the organic phase is washed with water and finally dried over sodium sulfate. The solvent is eliminated, the residue is suspended in water and neutralized with 1N hydrochloric acid. The aqueous phase is extracted with diethyl ether, the organic phase is dried over sodium sulfate, and finally the solvent is eliminated. Lastly the residue is recrystallized from petroleum ether and the product is dried in vacuo at 50° C. Yield: 15.3 g (76% of theory); $R_f$ value: 0.60 (silica gel, petroleum ether/ethyl acetate=5:2); m.p. 75° C.-77° C.; $C_{17}H_{16}O_3$; EII mass spectrum: m/z=269 [M+H]$^+$.

Example II.1

Ethyl 3-(4'-chlorobiphenyl-4-yl)-3-oxopropionate

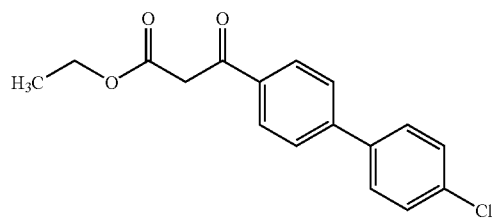

4.29 g (32.5 mmol) of monoethyl malonate is dissolved in 100 mL of THF and 42.3 mL (67.7 mmol) of butyllithium solution (1.6N in hexane) is added dropwise at −60° C. The temperature is allowed to come up to −15° C., then the mixture is cooled again to −65° C. and 3.40 g (13.5 mmol) of 4'-chlorobiphenyl-4-carboxylic acid chloride (for preparation see Gazz. Chim. Ital. 1949, 79, 453.) in 30 mL of THF is added dropwise. The mixture is kept for 5 minutes at −65° C., then heated for 2 hours to ambient temperature. The mixture is poured onto 50 mL of 1N hydrochloric acid, extracted with 300 mL of diethyl ether, and the organic phase is washed with saturated sodium hydrogen carbonate solution and water and finally dried over sodium sulfate. The solvent is eliminated, the residue is recrystallized from petroleum ether and the product is dried in vacuo. Yield: 3.10 g (76% of theory); $R_f$ value: 0.60 (silica gel, petroleum ether/ethyl acetate=5:2); m.p. 45° C.-50° C.; $C_{17}H_{15}ClO_3$; EII mass spectrum: m/z=303/305 [M+H]$^+$.

The following compounds are also synthesized analogously to the method described above:
(II.2) ethyl 3-(3-chlorobiphenyl-4-yl)-3-oxopropionate; and
(II.3) ethyl 3-(4-methoxyphenyl)-3-oxopropionate.

Example III.1

3-chloro-4-[2-(4-methylpiperidin-1-yl)ethoxy]phenylamine

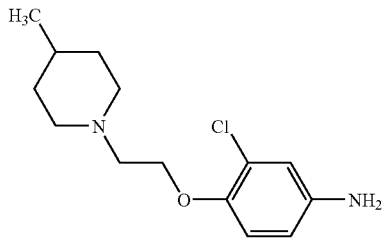

III.a: 4-(2-bromoethoxy)-3-chloronitrobenzene 36.6 mL (416 mmol) of 1,2-dibromoethane is dissolved in 200 mL of DMF and 11.5 g (83.3 mmol) of potassium carbonate is added. 7.20 g (41.6 mmol) of 2-chloro-4-nitrophenol in 40 mL of DMF is slowly added dropwise to this mixture. The mixture is stirred for 3 hours at ambient temperature. The solvent is eliminated, the residue is taken up in ethyl acetate and washed with saturated saline solution. The organic phase is dried over sodium sulfate. The solvent is eliminated and the residue is purified through a silica gel column with a gradient of petroleum ether/ethyl acetate (4:1 to 9:1). Yield: 7.9 g (68% of theory); $R_f$ value: 0.55 (silica gel, petroleum ether/ethyl acetate=3:1); $C_8H_7BrClNO_3$.

III.1.b: 3-chloro-4-[2-(4-methylpiperidin-1-yl)ethoxy]nitrobenzene 7.80 g (27.8 mmol) of 4-(2-bromoethoxy)-3-chloronitrobenzene (III.1.a) and 10.1 mL (84.0 mmol) of 4-methylpiperidine is dissolved in 100 mL of methylene chloride and stirred for 12 hours at ambient temperature. Then the mixture is filtered through 400 g of aluminum oxide (activity 2-3) with methylene chloride/methanol 49:1 as eluant. Yield: 6.9 g (83% of theory); $R_f$ value: 0.50 (aluminum oxide, petroleum ether/ethyl acetate=3:1); $C_{14}H_{19}ClN_2O_3$; EII mass spectrum: m/z=299/301 [M+H]⁺.

III.1.c: 3-chloro-4-[2-(4-methylpiperidin-1-yl)ethoxy]phenylamine 6.90 g (23.1 mmol) of 3-chloro-4-[2-(4-methylpiperidin-1-yl)ethoxy]nitrobenzene (III.1.b) are dissolved in 100 mL of THF and hydrogenated for 8 hours at ambient temperature at a pressure of 20 psi with hydrogen and 3.0 g of Raney nickel as catalyst. Then the catalyst is filtered off, the solvent is eliminated, and the residue is purified through a silica gel column with a gradient of methylene chloride/methanol (33:1 to 9:1) as eluant. Yield: 3.66 g (59% of theory); $R_f$ value: 0.50 (silica gel, methylene chloride/methanol=9:1); $C_{14}H_{21}ClN_2O$; EII mass spectrum: m/z=269/271 [M+H]⁺.

The following compounds are also synthesized analogously to the method described above:
(III.2) 4-[2-(3,5-dimethylpiperidin-1-yl)ethoxy]-3-methoxyphenylamine;
(III.3) 4-[2-(4-methylpiperidin-1-yl)ethoxy]-3-methoxyphenylamine;
(III.4) 3-chloro-4-[2-(morpholin-4-yl)ethoxy]phenylamine;
(III.5) 3-chloro-4-[2-(N-methylcyclopropylmethylamino)ethoxy]phenylamine;
(III.6) 3-chloro-4-[2-(4-methoxypiperidin-1-yl)ethoxy]phenylamine;
(III.7) 3-chloro-4-[2-(4-methylpiperazin-1-yl)ethoxy]phenylamine; and
(III.8) 3-chloro-4-[2-(4-hydroxypiperidin-1-yl)ethoxy]phenylamine.

Example IV.1

3-chloro-4-(2-diethylaminoethoxy)phenylamine

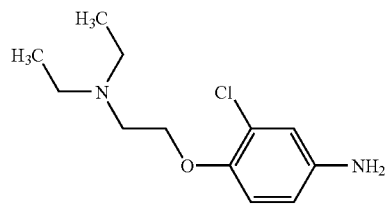

IV.1.a:
3-chloro-4-(2-diethylaminoethoxy)nitrobenzene 52.0 g (0.30 mol) of 2-chloro-4-nitrophenol is dissolved in 500 mL of DMF and 165 g (1.20 mol) of potassium carbonate is added batchwise. The mixture is stirred for 30 minutes at ambient temperature. Then 51.6 g (0.30 mol) of 2-diethylaminoethylchloride hydrochloride is added and the mixture is stirred for 3 days at ambient temperature. After this time, the mixture is filtered off, the solvent is eliminated, the residue is taken up in ethyl acetate, and washed with water. The organic phase is filtered through aluminum oxide (activity 2-3) and concentrated by evaporation. Yield: 41.0 g (50% of theory); $R_f$ value: 0.60 (silica gel, methylene chloride/methanol/ammonia=9:1:0.01); $C_{12}H_{17}ClN_2O_3$.

IV.1.b:
3-chloro-4-(2-diethylaminoethoxy)phenylamine 41.0 g (150 mmol) of 3-chloro-4-(2-diethylaminoethoxy)nitrobenzene (IV.1.a) is dissolved in 250 mL of methanol and hydrogenated for 5 hours at ambient temperature at a pressure of 50 psi with hydrogen and 4.0 g of Raney nickel as catalyst. Then the catalyst is filtered off and the solvent is eliminated. The residue is recrystallized from petroleum ether and dried in vacuo. Yield: 33.0 g (91% of theory); $R_f$ value: 0.40 (silica gel, methylene chloride/methanol/ammonia=9:1:0.01); $C_{12}H_{19}ClN_2O$; EII mass spectrum: m/z=243/245 [M+H]⁺.

The following compounds are also synthesized analogously to the method described above:
(IV.2) 4-(2-diethylaminoethoxy)phenylamine;
(IV.3) 4-(2-diethylaminoethoxy)-3-methoxyphenylamine;
(IV.4) 4-(2-pyrrolidin-1-ylethoxy)-3-trifluoromethylphenylamine; and
(IV.5) 4-(3-diethylaminopropoxy)phenylamine.

Example V.1

3-methoxycarbonyl-4-(2-pyrrolidin-1-ylethoxy)phenylamine

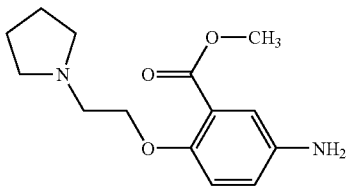

V.1.a: 3-methoxycarbonyl-4-(2-pyrrolidin-1-ylethoxy)nitrobenzene 3.43 g (29.8 mmol) of 2-pyrrolidin-1-ylethanol is dissolved in 60 mL of toluene and 575 mg (25.0 mmol) of sodium is added batchwise. The mixture is heated to 100° C. and then stirred for a further 12 hours at 50° C. After cooling, 5.00 g (22.5 mmol) of methyl 2-chloro-5-nitrobenzoate are added batchwise and the mixture is stirred for 1 day at ambient temperature. After this time, the solvent is eliminated, the residue is taken up in methylene chloride and washed with water. The organic phase is dried over sodium sulfate and concentrated by rotary evaporation. Finally the product is purified through a silica gel column with a gradient of methylene chloride/methanol/ammonia (8:2 to 8:2:0.1) as eluant. Yield: 1.65 g (25% of theory); $R_f$ value: 0.45 (silica gel, methylene chloride/methanol/ammonia=9:1:0.1); $C_{14}H_{18}N_2O_5$; EII mass spectrum: m/z=295 [M+H]$^+$.

V.1.b: 3-methoxycarbonyl-4-(2-pyrrolidin-1-ylethoxy)phenylamine 1.65 g (5.61 mmol) of 3-methoxycarbonyl-4-(2-pyrrolidin-1-ylethoxy)nitrobenzene (V.1.a) is dissolved in 100 mL of methanol and hydrogenated with hydrogen and 200 mg of Raney nickel as catalyst until the reaction is complete. Then the catalyst is filtered off and the solvent is eliminated. Yield: 1.43 g (97% of theory); $R_f$ value: 0.15 (silica gel, methylene chloride/methanol/ammonia=9:1:0.1); $C_{14}H_{20}N_2O_3$; EII mass spectrum: m/z=265 [M+H]$^+$.

Example VI.1

3-chloro-4-(2-diethylaminoethyl)phenylamine

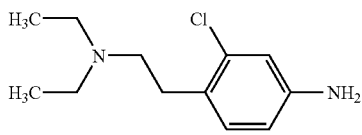

VI.1.a: (2-chloro-4-nitrophenyl)acetic acid chloride 8.10 g (37.6 mmol) of (2-chloro-4-nitrophenyl)acetic acid is suspended in 40 mL of thionyl chloride and refluxed for 2 hours. The product is reacted further without any more purification. Crude yield: 8.80 g (100% of theory); $C_8H_5Cl_2NO_3$.

VI.1.b: 2-(2-chloro-4-nitrophenyl)-N,N-diethylacetamide 5.67 mL (54.0 mmol) of diethylamine is dissolved in 50 mL of ethyl acetate and 3.20 g (13.7 mmol) of (2-chloro-4-nitrophenyl)acetic acid chloride (VI.1.a) in 50 mL of ethyl acetate is slowly added dropwise at 0° C. Then the mixture is stirred for another 2 hours at ambient temperature. After this time, some more ethyl acetate is added and the mixture is washed twice with water and twice with saturated saline solution. The organic phase is dried over sodium sulfate, the solvent is eliminated and the residue is dried in vacuo. Yield: 3.70 g (100% of theory); $R_f$ value: 0.45 (silica gel, petroleum ether/ethyl acetate=1:1); $C_{12}H_{15}ClN_2O_3$; EII mass spectrum: m/z=271/273 [M+H]$^+$.

VI.1.c: [2-(2-chloro-4-nitrophenyl)ethyl]diethylamine 65.0 mL (65.0 mmol) of a 1M borane-THF solution is added dropwise at ambient temperature to a solution of 3.70 g (13.7 mmol) 2-(2-chloro-4-nitrophenyl)-N,N-diethylacetamide (VI.1.b) in 130 mL of THF and the mixture is stirred for 4 hours. Then the reaction mixture is evaporated down and the residue is combined with 15 mL of methanol and 15 mL of dilute hydrochloric acid. The mixture is then stirred for 15 minutes at 100° C., cooled, and diluted with water. Then the mixture is made alkaline with sodium carbonate solution and extracted twice with ethyl acetate. The combined organic phases are extracted twice with water and once with saturated saline solution and dried over sodium sulfate. The purification is carried out by column chromatography on Alox (neutral, activity II-III) with petroleum ether/ethyl acetate (4:1) as eluant. Yield: 2.10 g (60% of theory); $R_f$ value: 0.65 (Alox, petroleum ether/ethyl acetate=3:1); $C_{12}H_{17}ClN_2O_2$.

VI.1.d: 3-chloro-4-(2-diethylaminoethyl)phenylamine 2.00 g (7.79 mmol) of [2-(2-chloro-4-nitrophenyl)ethyl] diethylamine (VI.1.c) is dissolved in 50 mL of THF and hydrogenated for 2.5 hours at ambient temperature at a pressure of 25 psi with hydrogen and 0.8 g of Raney nickel as catalyst. Then the catalyst is filtered off and the solvent is eliminated. Yield: 1.80 g (100% of theory); $R_f$ value: 0.45 (Alox, petroleum ether/ethyl acetate=1:1); $C_{12}H_{19}ClN_2$; EII mass spectrum: m/z=227/229 [M+H]$^+$.

The following compounds are also synthesized analogously to the method described above:
- (VI.2) 3-chloro-4-[2-(4-methylpiperidin-1-yl)ethyl]phenylamine;
- (VI.3) 3-chloro-4-[2-(4-methoxypiperidin-1-yl)ethyl]phenylamine;
- (VI.4) 3-chloro-4-[2-(N-methylisopropylamino)ethyl]phenylamine;
- (VI.5) 3-chloro-4-{2-[4-(morpholin-4-yl)piperidin-1-yl]ethyl}phenylamine;
- (VI.6) 3-chloro-4-[2-(4-hydroxy-4-trifluoromethylpiperidin-1-yl)ethyl]phenylamine;
- (VI.7) 3-chloro-4-[2-(4-tert-butoxycarbonylaminopiperidin-1-yl)ethyl]phenylamine;

(VI.8) 3-chloro-4-[2-(N-ethyl-2-hydroxyethylamino)ethyl]phenylamine; and
(VI.9) 2-amino-5-(piperidin-1-ylmethyl)pyridine.

Example VII.1

5-amino-1-(2-pyrrolidin-1-ylethyl)-1H-indole

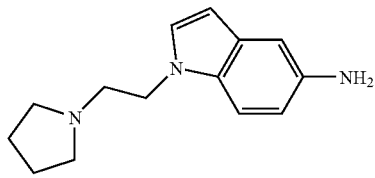

VII.1.a: 5-nitro-1-(2-pyrrolidin-1-ylethyl)-1H-indole

A reaction mixture of 16.2 g (100 mmol) of 5-nitroindole, 35.0 g (206 mmol) of 1-(2-chloroethyl)pyrrolidine hydrochloride, and 51.0 g (369 mmol) of potassium carbonate in 500 mL of DMF is stirred for 48 hours at ambient temperature and then filtered. The filtrate is evaporated down, and the residue is dissolved in dichloromethane and dried over sodium sulfate. The drying agent is filtered off and the filtrate evaporated down. Yield: 25 g (96% of theory); $R_f$ value: 0.65 (silica gel, dichloromethane/methanol/ammonia=9:1:0.1); $C_{14}H_{17}N_3O_2$; EII mass spectrum: m/z=260 [M+H]$^+$.

VII.1.b: 5-amino-1-(2-pyrrolidin-1-ylethyl)-1H-indole

Prepared analogously to Example VI.1.d from 27.0 g (104 mmol) of 5-nitro-1-(2-pyrrolidin-1-ylethyl)-1H-indole (VII.1.a) in THF as solvent. Yield: 23.2 g (97% of theory); $R_f$ value: 0.50 (silica gel, dichloromethane/methanol/ammonia=9:1:0.1); $C_{14}H_{19}N_3$; EII mass spectrum: m/z=230 [M+H]$^+$.

The following compounds are also synthesized analogously to the method described above:
(VII.2) 5-amino-1-(2-piperidin-1-ylethyl)-1H-indole;
(VII.3) 5-amino-1-(2-azepan-1-ylethyl)-1H-indole;
(VII.4) 5-amino-1-(2-diisoproylaminoethyl)-1H-indole;
(VII.5) 5-amino-1-{2-[bis-(2-methoxyethyl)amino]ethyl}-1H-indole;
(VII.6) 5-amino-1-[2-(N-benzylethylamino)ethyl]-1H-indole; and
(VII.7) 5-amino-1-(2-diethylaminoethyl)-1H-indole.

Example VIII.1

2-(pyrrolidin-1-ylmethyl)benzoxazol-6-ylamine

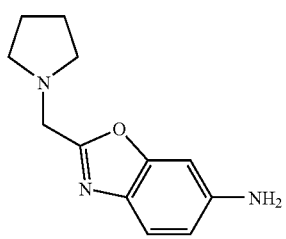

VIII.1.a: 2-chloromethyl-6-nitrobenzoxazole

A reaction mixture of 12.0 g (77.9 mmol) of 2-amino-4-nitrophenol and 10.5 mL (77.9 mmol) of 2-chloro-1.1.1-trimethoxyethane in 110 mL of ethanol is stirred for 3 hours at 80° C. After this time, the mixture is poured onto water and the precipitate formed is filtered off. The filtrate is washed with water and dried at 80° C. Yield: 14.2 g (86% of theory); $C_8H_5ClN_2O_3$; EII mass spectrum: m/z=213/215 [M+H]$^+$.

VIII.1.b: 6-nitro-2-(pyrrolidin-1-ylmethyl)benzoxazole

A reaction mixture of 3.00 g (14.1 mmol) of 2-chloromethyl-6-nitrobenzoxazole (VIII.1.a), 1.50 mL (18.0 mmol) of pyrrolidine, and 3.90 g (28.2 mmol) of potassium carbonate in 30 mL of DMF is stirred for 12 hours at 50° C. After this time, the mixture is diluted with water and covered with diethyl ether. The precipitate formed is filtered off and dried at 80° C. Yield: 1.80 g (52% of theory); $C_{12}H_{13}N_3O_3$; EII mass spectrum: m/z=248 [M+H]$^+$.

VIII.1.c: 2-(pyrrolidin-1-ylmethyl)benzoxazol-6-ylamine

Prepared analogously to Example VI.1.d from 1.80 g (7.28 mmol) of 6-nitro-2-(pyrrolidin-1-ylmethyl)benzoxazole (VIII.1.b) in methanol as solvent. Yield: 1.10 g (70% of theory); $R_f$ value: 0.60 (aluminum oxide, dichloromethane/ethanol=20:1); $C_{12}H_{15}N_3O$; EII mass spectrum: m/z=218 [M+H]$^+$.

Example IX.1

2-(4-dimethylaminomethylphenyl)ethylamine

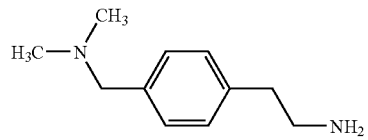

IX.1.a: (4-dimethylaminomethylphenyl)acetonitrile

A reaction mixture of 4.40 g (20.9 mmol) of (4-bromomethyl)acetonitrile (for preparation method see Magnet. Reson. Chem. 2000, 38, 129-134), 1.71 g (21.0 mmol) of dimethylamine hydrochloride, and 9.12 g (66.0 mmol) of potassium carbonate in 30 mL of acetone is stirred for 4 hours at ambient temperature. After this time, the mixture is concentrated by evaporation, taken up in methylene chloride, and washed with water. The organic phase is dried over sodium sulfate and then the solvent is eliminated. Yield: 3.60 g (99% of theory); $C_{11}H_{14}N_2$; EII mass spectrum: m/z=175 [M+H]$^+$.

IX.1.b: 2-(4-dimethylaminomethylphenyl)ethylamine 3.60 g (20.7 mmol) of (4-dimethylaminomethylphenyl)acetonitrile (IX.1.a) is dissolved in 50 mL of methanolic ammonia and hydrogenated for 5 hours at 50° C. at a pressure of 3 bar with hydrogen and 0.45 g of Raney nickel as catalyst. Then the catalyst is filtered off and the solvent is eliminated. Yield: 3.60 g (98% of theory); $R_f$ value: 0.20 (silica gel, methylene chloride/methanol=9:1); $C_{11}H_{18}N_2$; EII mass spectrum: m/z=179 [M+H]$^+$.

The following compounds are also synthesized analogously to the method described above:
(IX.2) 2-[4-(pyrrolidin-1-ylmethyl)phenyl]ethylamine;
(IX.3) 2-[4-(3-azaspiro[5.5]undec-3-ylmethyl)phenyl]ethylamine;
(IX.4) 2-[4-(4-hydroxy-4-phenylpiperidin-1-ylmethyl)phenyl]ethylamine;
(IX.5) {1-[4-(2-aminoethyl)benzyl]piperidin-4-yl}pyridin-2-ylamine; and
(IX.6) 2-methyl-2-[4-(pyrrolidin-1-ylmethyl)phenyl]propylamine.

Example X

The following compounds are synthesized using methods already described in international Patent Application WO 01/27081 or may at least be prepared analogously to methods described therein:
(X.1) 4-(piperidin-1-ylmethyl)phenylamine;
(X.2) 4-(diethylaminomethyl)phenylamine;
(X.3) 4-(2-diethylaminoethyl)phenylamine;
(X.4) 3-chloro-4-(piperidin-1-ylmethyl)phenylamine;
(X.5) 3-chloro-4-[(cis-3,5-dimethylpiperidin-1-yl)methyl]phenylamine;
(X.6) 4-[(3,5-dimethylpiperidin-1-yl)methyl]phenylamine;
(X.7) 4-[(4-methoxypiperidin-1-yl)methyl]phenylamine;
(X.8) 4-[(4-methylpiperidin-1-yl)methyl]phenylamine;
(X.9) 4-[(4-methylpiperazin-1-yl)methyl]phenylamine;
(X.10) 4-[(N-methylcyclopropylmethylamino)methyl]phenylamine;
(X.11) 4-[(2,6-dimethylpiperidin-1-yl)methyl]phenylamine;
(X.12) 4-(pyrrolidin-1-ylmethyl)phenylamine;
(X.13) 4-(morpholin-4-ylmethyl)phenylamine; and
(X.14) 4-[(4-hydroxypiperidin-4-yl)methyl]phenylamine.

Example XI.1

N-methyl-4-(2-diethylaminoethoxy)phenylamine

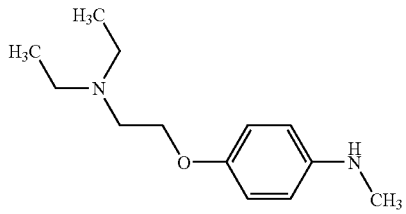

XI.1.a: N-methoxycarbonyl-4-(2-diethylaminoethoxy)phenylamine 76.4 g (0.367 mol) of 4-(2-diethylaminoethoxy)phenylamine (compound IV.2) and 102 mL (0.733 mol) of triethylamine are dissolved in 400 mL of THF and 49.2 g (0.367 mol) of dimethylpyrocarbonate in 200 mL of THF is added over 45 minutes at ambient temperature. The mixture is stirred for a further 2 hours at ambient temperature. After this time, the solvent is evaporated down, the residue is taken up in ethyl acetate and water and the organic phase is washed twice with water. The solvent is eliminated and the residue is purified through an aluminum oxide column with petroleum ether/ethyl acetate (3:1) as eluant. Yield: 63.3 g (65% of theory); $R_f$ value: 0.60 (aluminum oxide, petroleum ether/ethyl acetate=1:3); $C_{14}H_{22}N_2O_3$; EII mass spectrum: m/z=267 [M+H]$^+$.

XI.1.b:
N-methyl-4-(2-diethylaminoethoxy)phenylamine 10.7 g (280 mmol) of lithium aluminum hydride is placed in 600 mL of THF and 30.0 g (113 mmol) of N-methoxycarbonyl-4-(2-diethylaminoethoxy)phenylamine (compound XI.1.a) in 300 mL of THF is carefully added dropwise at 0° C. The mixture is stirred for 12 hours at ambient temperature. After this time, a further 7.00 g (183 mmol) of lithium aluminum hydride is added and the mixture is stirred for a further 24 hours at ambient temperature. After this time, it is carefully neutralized with sodium hydroxide solution. The mixture is filtered, the filtrate is dried over sodium sulfate, and finally the solvent is eliminated. Yield: 24.7 g (99% of theory); $R_f$ value: 0.45 (silica gel, methylene chloride/methanol/ammonia=9:1:0.1); $C_{13}H_{22}N_2O$; EII mass spectrum: m/z=223 [M+H]$^+$.

The following compound is also synthesized analogously to the preparation method described above: (XI.2) N-methyl-4-(piperidin-1-ylmethyl)phenylamine.

Example XII.1

3-biphenyl-4-ylpropynoic acid-[3-chloro-4-(2-diethylaminoethoxy)phenyl]amide

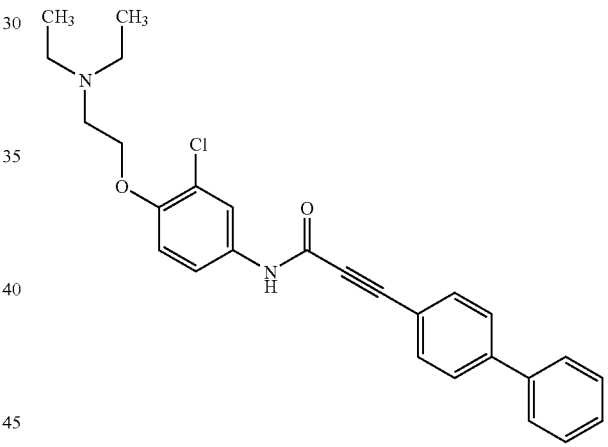

0.48 g (2.0 mmol) of biphenyl-4-ylpropynoic acid chloride (for preparation method see Bioorg. Med. Chem. 1996, 4, 851) is dissolved in 15 mL of toluene and 0.58 g (2.4 mmol) of [2-(2-chloro-4-aminophenoxy)ethyl]diethylamine (educt IV.1) in 10 mL of toluene at ambient temperature is added dropwise. The mixture is stirred for 8 hours at ambient temperature, the solvent is eliminated, and the residue is taken up in ethyl acetate and washed with water. The organic phase is dried over sodium sulfate, the solvent is eliminated and the residue is purified through a silica gel column with dichloromethane/methanol/ammonia (9:1:0.01) as eluant. Yield: 0.28 g (31% of theory); m.p.: 105-108° C.; $R_f$ value: 0.50 (silica gel, dichloromethane/methanol/ammonia=9:1:0.1); $C_{27}H_{27}ClN_2O_2$; EII mass spectrum: m/z=447/449 [M+H]$^+$.

The following compounds are also synthesized analogously to the method described above:
(XII.2) 3-(2-chloro-4-trifluoromethylphenyl)propynoic acid-[3-chloro-4-(2-diethylaminoethoxy)phenyl]amide; and
(XII.3) 3-(3-bromobiphenyl-4-yl)propynoic acid-{3-chloro-4-[2-(4-methylpiperidin-1-yl)ethyl]phenyl}amide.

Preparation of the Final Compounds

Example 1

3-biphenyl-4-yl-N-{3-chloro-4-[2-(4-methylpiperidin-1-yl)ethoxy]phenyl}-3-oxopropionamide

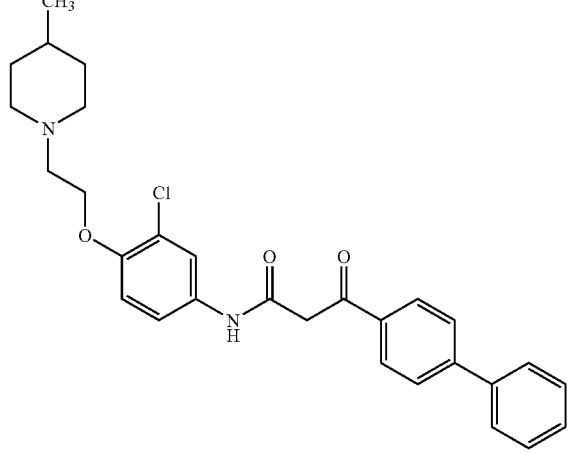

300 mg (1.00 mmol) of ethyl 3-biphenyl-4-yl-3-oxopropynoate (educt I.1) and 269 mg (1.00 mmol) of 3-chloro-4-[2-(4-methylpiperidin-1-yl)ethoxy]phenylamine (educt III.1) are dissolved in 5 mL of toluene and stirred for 8 hours at 120° C. in the open test tube, while ethanol is distilled off. After cooling, petroleum ether is added, and the precipitate formed is suction filtered and dried in vacuo at 80° C. Yield: 300 mg (61% of theory); $R_f$ value: 0.60 (silica gel, methylene chloride/methanol/ammonia=9:1:0.1); m.p. 135-139° C.; $C_{29}H_{31}ClN_2O_3$; EII mass spectrum: m/z=491/493 $[M+H]^+$.

The following compounds of general formula I-1 are prepared analogously to Example 1.0, the educts used being shown in the column headed "Educts":

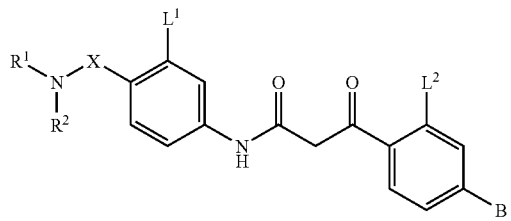

(I-1)

| Ex. # | $R^1R^2NX$ | $L^1$ | $L^2$ | B | Educts | mass spectrum | m.p. [° C.] | $R_f$-value* |
|---|---|---|---|---|---|---|---|---|
| 1.1 | Et₂N–⁀O–⁀ | —Cl | —H | –⁀–C₆H₄–Cl | II.1 IV.1 | 499/501/503 $[M+H]^+$ | 175-180 | 0.50 (A) |
| 1.2 | Et₂N–⁀O–⁀ | —H | —H | –⁀–C₆H₄–H | I.1 IV.2 | 431 $[M+H]^+$ | 140-142 | 0.40 (A) |
| 1.3 | Et₂N–⁀O–⁀ | —OCH₃ | —H | –⁀–C₆H₄–H | I.1 IV.3 | 461 $[M+H]^+$ | 108-110 | 0.60 (B) |
| 1.4 | Et₂N–⁀O–⁀ | —Cl | —Cl | –⁀–C₆H₄–H | II.2 IV.1 | 499/501/503 $[M+H]^+$ | 108-111 | 0.40 (C) |
| 1.5 | Et₂N–⁀O–⁀ | —H | —Cl | –⁀–C₆H₄–H | II.2 IV.2 | 465/467 $[M+H]^+$ | 108-112 | 0.40 (A) |

-continued (I-1)

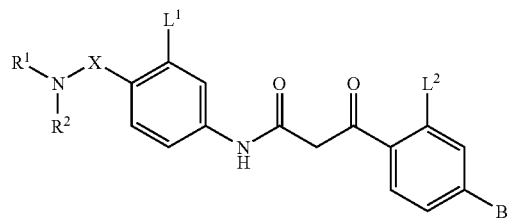

| Ex. # | R¹R²NX | L¹ | L² | B | Educts | mass spectrum | m.p. [° C.] | R$_f$-value* |
|---|---|---|---|---|---|---|---|---|
| 1.6 | Et₂N~~O~~ | —OCH₃ | —Cl | ⌬H | II.2 IV.3 | 495/497 [M + H]⁺ | 157-160 | 0.70 (B) |
| 1.7 | pyrrolidine-CH₂CH₂-O- | —CF₃ | —H | ⌬H | I.1 IV.4 | 497 [M + H]⁺ | 130-135 | 0.45 (D) |
| 1.8 | Et₂N~~~O~~ | —H | —H | ⌬H | I.1 IV.5 | 445 [M + H]⁺ | 152-157 | 0.45 (D) |
| 1.9 | pyrrolidine-CH₂CH₂-O- | —COO—CH₃ | —H | ⌬H | I.1 V.1 | 487 [M + H]⁺ | 131-135 | 0.45 (D) |
| 1.10 | Et₂N~~~ | —Cl | —H | ⌬H | I.1 VI.1 | 449/451 [M + H]⁺ | 118-122 | 0.20 (A) |
| 1.11 | Et₂N~~~ | —Cl | —Cl | ⌬H | II.2 VI.1 | 483/485/ 487 [M + H]⁺ | 132-136 | 0.20 (A) |
| 1.12 | piperidine-CH₂- | —H | —H | ⌬H | I.1 X.1 | 413 [M + H]⁺ | 157-160 | 0.50 (A) |
| 1.13 | (H₃C-CH₂)₂N-CH₂- | —H | —H | ⌬H | I.1 X.2 | 401 [M + H]⁺ | 126-130 | 0.60 (A) |
| 1.14 | piperidine-CH₂- | —H | —Cl | ⌬H | II.2 X.1 | 447/449 [M + H]⁺ | 72-75 | 0.50 (A) |
| 1.15 | (H₃C-CH₂)₂N-CH₂- | —H | —Cl | ⌬H | II.2 X.2 | 435/437 [M + H]⁺ | 155-160 | 0.50 (A) |

-continued

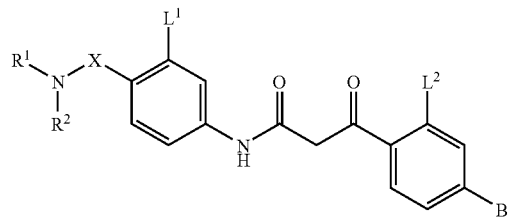
(I-1)

| Ex. # | R¹R²NX | L¹ | L² | B | Educts | mass spectrum | m.p. [° C.] | $R_f$-value* |
|---|---|---|---|---|---|---|---|---|
| 1.16 | piperidinyl-CH₂C(CH₃)₂- | —H | —H | 4-Cl-C₆H₄-C(CH₃)₂- | II.1 X.1 | 447/449 [M + H]⁺ | 202-204 | 0.40 (A) |
| 1.17 | (H₃CCH₂)₂N-CH₂CH₂C(CH₃)₂- | —H | —H | C₆H₅-C(CH₃)₂- | 1.1 X.3 | 415 [M + H]⁺ | 144-148 | 0.50 (D) |
| 1.18 | 3,5-diMe-piperidinyl-CH₂CH₂O-C(CH₃)₂- | —OCH₃ | —H | C₆H₅-C(CH₃)₂- | I.1 III.2 | 501 [M + H]⁺ | 224-228 | 0.60 (D) |
| 1.19 | 4-Me-piperidinyl-CH₂CH₂O-C(CH₃)₂- | —OCH₃ | —H | C₆H₅-C(CH₃)₂- | I.1 III.3 | 487 [M + H]⁺ | 106-110 | 0.60 (D) |
| 1.20 | piperidinyl-CH₂C(CH₃)₂- | —Cl | —H | 4-Cl-C₆H₄-C(CH₃)₂- | II.1 X.4 | 482 [M + H]⁺ | 175-177 | 0.45 (C) |
| 1.21 | (3R,5S)-3,5-diMe-piperidinyl-CH₂C(CH₃)₂- | —Cl | —H | 4-Cl-C₆H₄-C(CH₃)₂- | II.1 X.5 | 509/511/513 [M + H]⁺ | 174-177 | 0.80 (C) |
| 1.22 | 3,5-diMe-piperidinyl-CH₂C(CH₃)₂- | —H | —H | 4-Cl-C₆H₄-C(CH₃)₂- | II.1 X.6 | 475/477 [M + H]⁺ | 175-178 | 0.45 (D) |
| 1.23 | 4-MeO-piperidinyl-CH₂C(CH₃)₂- | —H | —H | 4-Cl-C₆H₄-C(CH₃)₂- | II.1 X.7 | 477/479 [M + H]⁺ | 178-181 | 0.50 (C) |

-continued

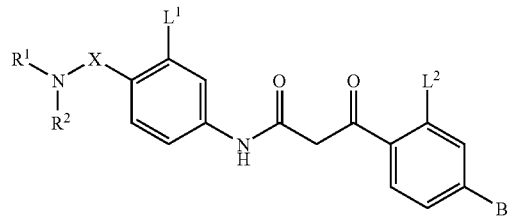
(I-1)

| Ex. # | R¹R²NX | L¹ | L² | B | Educts | mass spectrum | m.p. [° C.] | R$_f$-value* |
|---|---|---|---|---|---|---|---|---|
| 1.24 | 4-methylpiperidin-1-yl-CH₂C(CH₃)₂– | —H | —H | 4-Cl-C₆H₄– | II.1 X.8 | 461/463 [M + H]⁺ | 168-170 | 0.35 (C) |
| 1.25 | 4-methylpiperazin-1-yl-CH₂C(CH₃)₂– | —H | —H | 4-Cl-C₆H₄– | II.1 X.9 | 462/464 [M + H]⁺ | 176-178 | 0.30 (D) |
| 1.26 | (cyclopropylmethyl)(methyl)N-CH₂C(CH₃)₂– | —H | —H | 4-Cl-C₆H₄– | II.1 X.10 | 447/449 [M + H]⁺ | 167-170 | 0.50 (C) |
| 1.27 | 2,6-dimethylpiperidin-1-yl-CH₂C(CH₃)₂– | —H | —H | 4-Cl-C₆H₄– | II.1 X.11 | 475/477 [M + H]⁺ | 168-171 | 0.45 (C) |
| 1.28 | pyrrolidin-1-yl-CH₂C(CH₃)₂– | —H | —H | 4-Cl-C₆H₄– | II.1 X.12 | 433/435 [M + H]⁺ | 187-189 | 0.35 (C) |
| 1.29 | (H₃C-CH₂)₂N-CH₂C(CH₃)₂– | —H | —H | 4-Cl-C₆H₄– | II.1 X.2 | 435/437 [M + H]⁺ | 175-178 | 0.35 (C) |
| 1.30 | morpholin-4-yl-CH₂C(CH₃)₂– | —H | —H | 4-Cl-C₆H₄– | II.1 X.13 | 449/451 [M + H]⁺ | 188-190 | 0.45 (C) |
| 1.31 | 4-hydroxypiperidin-1-yl-CH₂C(CH₃)₂– | —H | —H | 4-Cl-C₆H₄– | II.1 X.14 | 463/465 [M + H]⁺ | 146-149 | 0.30 (C) |
| 1.32 | morpholin-4-yl-CH₂CH₂-O-C(CH₃)₂– | —Cl | —H | 4-H-C₆H₄– | I.1 III.4 | 479/481 [M + H]⁺ | 120-126 | 0.70 (D) |

-continued (I-1)

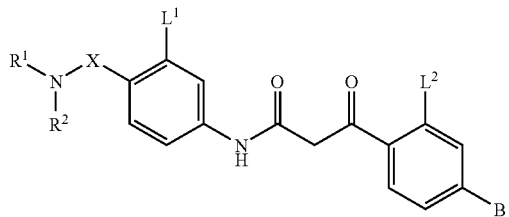

| Ex. # | R¹R²NX | L¹ | L² | B | Educts | mass spectrum | m.p. [° C.] | R$_f$-value* |
|---|---|---|---|---|---|---|---|---|
| 1.33 | cyclopropylmethyl-N(CH₃)-CH₂CH₂-O-C(CH₃)₃ | —Cl | —H | 4-tert-butylphenyl | I.1 III.5 | 477/479 [M + H]⁺ | 130-132 | 0.40 (C) |
| 1.34 | 4-MeO-piperidinyl-CH₂CH₂-O-C(CH₃)₃ | —Cl | —H | 4-tert-butylphenyl | I.1 III.6 | 507/509 [M + H]⁺ | 120-125 | 0.40 (C) |
| 1.35 | 4-Me-piperazinyl-CH₂CH₂-O-C(CH₃)₃ | —Cl | —H | 4-tert-butylphenyl | I.1 III.7 | 492/494 [M + H]⁺ | 130-135 | 0.30 (C) |
| 1.36 | 4-HO-piperidinyl-CH₂CH₂-O-C(CH₃)₃ | —Cl | —H | 4-tert-butylphenyl | I.1 III.8 | 493/495 [M + H]⁺ | 115-118 | 0.30 (C) |
| 1.37 | 4-Me-piperidinyl-CH₂-C(CH₃)₂- | —Cl | —H | 4-tert-butylphenyl | I.1 VI.2 | 475/477 [M + H]⁺ | 227-232 | 0.44 (C) |
| 1.38 | 4-MeO-piperidinyl-CH₂-C(CH₃)₂- | —Cl | —H | 4-tert-butylphenyl | I.1 VI.3 | 491/493 [M + H]⁺ | >130 | 0.53 (C) |
| 1.39 | (iPr)₂N-CH₃ with CH₂-C(CH₃)₂- | —Cl | —H | 4-tert-butylphenyl | I.1 VI.4 | 449/451 [M + H]⁺ | 81-85 | 0.32 (C) |

-continued

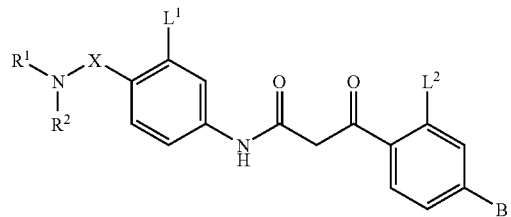
(I-1)

| Ex. # | R¹R²NX | L¹ | L² | B | Educts | mass spectrum | m.p. [° C.] | R$_f$-value* |
|---|---|---|---|---|---|---|---|---|
| 1.40 | (morpholine-piperidine with neopentyl linker) | —Cl | —H | (4-tert-butylphenyl) H | I.1 VI.5 | 546/548 [M + H]⁺ | 171-175 | 0.24 (C) |
| 1.41 | (4-hydroxy-4-trifluoromethylpiperidine with neopentyl linker) | —Cl | —H | (4-tert-butylphenyl) H | I.1 VI.6 | 545/547 [M + H]⁺ | 187-191 | 0.38 (C) |
| 1.42 | (Boc-amino piperidine with neopentyl linker) | —Cl | —H | (4-tert-butylphenyl) H | I.1 VI.7 | 576/578 [M + H]⁺ | 157-159 | 0.42 (C) |
| 1.43 | (N-ethyl-N-(2-hydroxyethyl)amino with neopentyl linker) | —Cl | —H | (4-tert-butylphenyl) H | I.1 VI.8 | | | |

Example 2

The following compounds of general formula II-1 are prepared analogously to Example 1.0, the educts used being shown in the column headed "Educts":

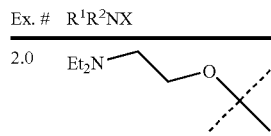
(II-1)

| Ex. # | R¹R²NX | L¹ | L² | L³ | Educts | mass spectrum | m.p. [° C.] | $R_f$-value* |
|---|---|---|---|---|---|---|---|---|
| 2.0 | Et₂N–⟨⟩–O–⟨⟩ | —Cl | —H | —OCH₃ | II.3 IV.1 | 419/421 [M + H]⁺ | 120-122 | 0.40 (A) |

Example 3

The following compounds of general formula III-1 are prepared analogously to Example 1.0, the educts used being shown in the column headed "Educts":

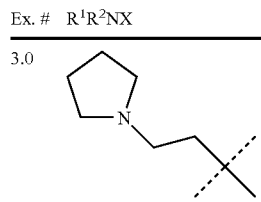
(III-1)

| Ex. # | R¹R²NX | L² | B | Educts | mass spectrum | m.p. [° C.] | $R_f$-value* |
|---|---|---|---|---|---|---|---|
| 3.0 | pyrrolidine-propyl | —Cl | phenyl-H | II.2 VII.1 | 419/421 [M + H]⁺ | 120-122 | 0.40 (A) |
| 3.1 | pyrrolidine-propyl | —H | phenyl-H | I.1 VII.1 | 452 [M + H]⁺ | 135-142 | 0.50 (A) |
| 3.2 | piperidine-propyl | —H | phenyl-H | I.1 VII.2 | 466 [M + H]⁺ | 60-65 | 0.50 (D) |

-continued
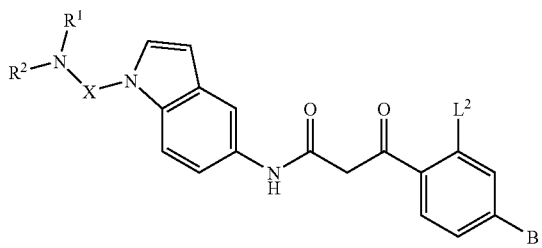
(III-1)
| Ex. # | R¹R²NX | L² | B | Educts | mass spectrum | m.p. [° C.] | $R_f$-value* |
|---|---|---|---|---|---|---|---|
| 3.3 | azepane-CH₂C(CH₃)₂- | —H | 4-tBu-C₆H₄— | I.1 VII.3 | 480 [M + H]⁺ | 127-129 | 0.50 (D) |
| 3.4 | (iPr)₂N-CH₂C(CH₃)₂- | —H | 4-tBu-C₆H₄— | I.1 VII.4 | 482 [M + H]⁺ | 139-144 | 0.65 (D) |
| 3.5 | (MeOCH₂CH₂)₂N-CH₂C(CH₃)₂- | —H | 4-tBu-C₆H₄— | I.1 VII.5 | 514 [M + H]⁺ | 83-86 | 0.60 (D) |
| 3.6 | PhCH₂(Et)N-CH₂C(CH₃)₂- | —H | 4-tBu-C₆H₄— | I.1 VII.6 | 516 [M + H]⁺ | 85-90 | 0.70 (D) |
| 3.7 | Et₂N-CH₂C(CH₃)₂- | —H | 4-tBu-C₆H₄— | I.1 VII.7 | 454 [M + H]⁺ | 99-104 | 0.55 (D) |

Example 4

The following compound of general formula IV-1 is prepared analogously to Example 1.0, the educts used being shown in the column headed "Educts":

(IV-1)

| Ex. # | $R^1R^2NX$ | $L^2$ | B | Educts | mass spectrum | m.p. [° C.] | $R_f$-value* |
|---|---|---|---|---|---|---|---|
| 4.0 | pyrrolidine-CH2- | —H | 4-tBu-phenyl-H | I.1 VIII.1 | 440 [M + H]$^+$ | 135-138 | 0.55 (D) |

Example 5

The following compounds of general formula V-1 are prepared analogously to Example 1.0, the educts used being shown in the column headed "Educts":

(V-1)

| Ex. # | $R^1R^2NX$ | $R^{7a}/R^{7b}$ | B | Educts | mass spectrum | m.p. [° C.] | $R_f$-value* |
|---|---|---|---|---|---|---|---|
| 5.0 | (H3C)2N-CH2- | —H | 4-tBu-phenyl-H | I.1 IX.1 | 401 [M + H]$^+$ | 120-125 | 0.40 (D) |
| 5.1 | pyrrolidine-CH2- | —H | 4-tBu-phenyl-H | I.1 IX.2 | 427 [M + H]$^+$ | 121-125 | 0.55 (D) |
| 5.2 | spiro-piperidine-CH2- | —H | 4-tBu-phenyl-H | I.1 IX.3 | 509 [M + H]$^+$ | 107-111 | 0.40 (D) |

-continued

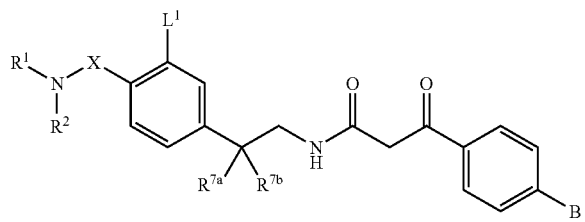

(V-1)

| Ex. # | R¹R²NX | R⁷ᵃ/R⁷ᵇ | B | Educts | mass spectrum | m.p. [° C.] | R_f-value* |
|---|---|---|---|---|---|---|---|
| 5.3 | 4-hydroxy-4-phenylpiperidine-N-neopentyl | —H | 4-tert-butylphenyl | I.1 IX.4 | 533 [M + H]⁺ | 98-103 | 0.40 (D) |
| 5.4 | 4-(pyridin-2-ylamino)piperidine-N-neopentyl | —H | 4-tert-butylphenyl | I.1 IX.5 | 533 [M + H]⁺ | 109-112 | 0.30 (D) |
| 5.5 | pyrrolidin-1-yl-neopentyl | —CH₃ | 4-tert-butylphenyl | I.1 IX.6 | 455 [M + H]⁺ | 100-106 | 0.40 (D) |

Example 6

The following compounds of general formula VI-1 are prepared analogously to Example 1.0, the educts used being shown in the column headed "Educts":

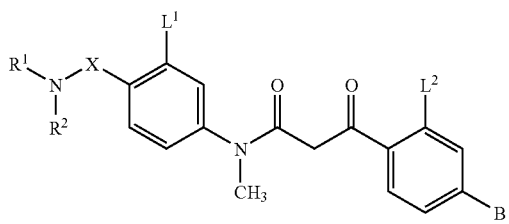

(VI-1)

| Ex. # | R¹R²NX | L¹ | L² | B | Educts | mass spectrum | m.p. [° C.] | R_f-value* |
|---|---|---|---|---|---|---|---|---|
| 6.0 | Et₂N-CH₂CH₂-O- | —H | —H | 4-tert-butylphenyl | I.1 XI.1 | 445 [M + H]⁺ | 108-112 | 0.50 (D) |
| 6.1 | piperidin-1-yl-neopentyl | —H | —H | 4-tert-butylphenyl | I.1 XI.1 | 427 [M + H]⁺ | 175 | 0.70 (A) |

Example 7

3-biphenyl-4-yl-N-[3-chloro-4-(2-diethylaminoethoxy)phenyl]-3-oxopropionamide

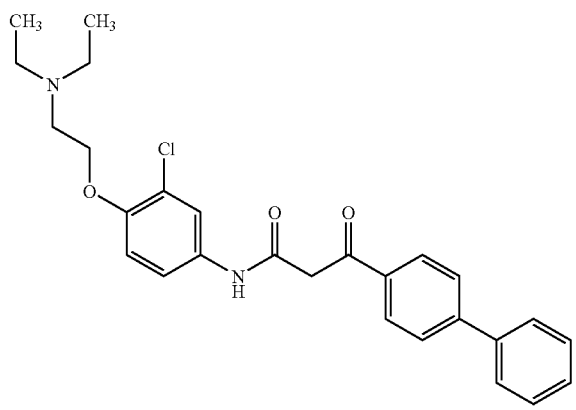

0.16 g (0.36 mmol) of 3-biphenyl-4-ylpropynoic acid-[3-chloro-4-(2-diethylaminoethoxy)phenyl]amide (educt XII.1) is dissolved in 10 mL of aqueous ethanol and 0.10 mL (1.0 mmol) of piperidine is added. The mixture is stirred for 8 hours at reflux temperature. After cooling, the solvent is eliminated, and the residue is suspended in ether and filtered off. The residue is dried in vacuo at 50° C. Yield: 75 mg (45% of theory); $R_f$ value: 0.40 (silica gel, methylene chloride/methanol/ammonia=9:1:0.01); m.p. 148° C.-151° C.; $C_{27}H_{29}ClN_2O_3$; EII mass spectrum: m/z=465/467 [M+H]$^+$.

The following compounds of general formula VII-1 are prepared analogously to Example 7.0, the educts used being shown in the column headed "Educts":

Example 8

5-(3-biphenyl-4-yl-3-oxopropionylamino)-2-(2-pyrrolidin-1-ylethoxy)benzoic acid

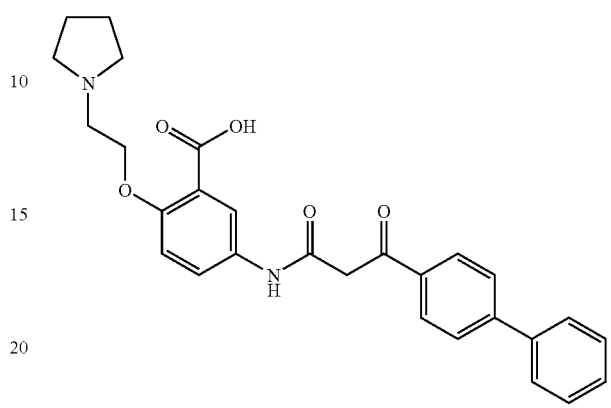

0.25 g (0.51 mmol) of methyl 5-(3-biphenyl-4-yl-3-oxopropionylamino)-2-(2-pyrrolidin-1-ylethoxy)benzoate (compound 1.9) is dissolved in 20 mL of methanol, 2.0 mL of 1N sodium hydroxide solution is added, and the mixture is stirred for 3 hours at 50° C. and 12 hours at ambient temperature. After this time, another 1.0 mL of 1N sodium hydroxide solution is added and the mixture is stirred for another 3 hours at 50° C. After cooling, 3.0 mL of 1N hydrochloric acid is added and the mixture is stirred for 1 hour at ambient temperature. The solvent is evaporated down, and the residue is taken up in a little methanol and the precipitate obtained is suction filtered and dried in vacuo at 80° C. Yield: 240 mg (100% of theory); $R_f$ value: 0.20 (silica gel, methylene chlo-

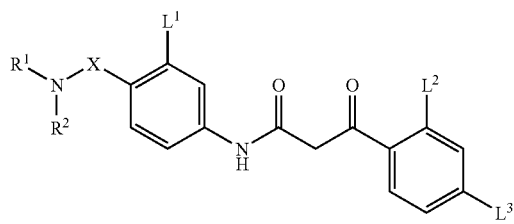

(VII-1)

| Ex. # | R¹R²NX | L¹ | L² | L³ | Educts | mass spectrum | m.p. [° C.] | $R_f$-value* |
|---|---|---|---|---|---|---|---|---|
| 7.1 | Et₂N—⁀O—⁀ | —Cl | —Cl | —CF₃ | XII.2 | 491/493/495 [M + H]$^+$ | n.b. | 0.40 (E) |
| 7.2 | H₃C—⟨piperidine⟩—⁀ | —Cl | —Br | ⟨phenyl-H⟩ | XII.3 | 553/555/557 [M + H]$^+$ | 139-144 | 0.48 (C) | ride/methanol/ammonia=9:1:0.1); m.p. 236° C.-240° C.; $C_{28}H_{28}N_2O_5$; EII mass spectrum: m/z=473 [M+H]$^+$.

Example 9

N-{4-[2-(4-aminopiperidin-1-yl)ethyl]-3-chlorophenyl}-3-biphenyl-4-yl-3-oxopropionamide

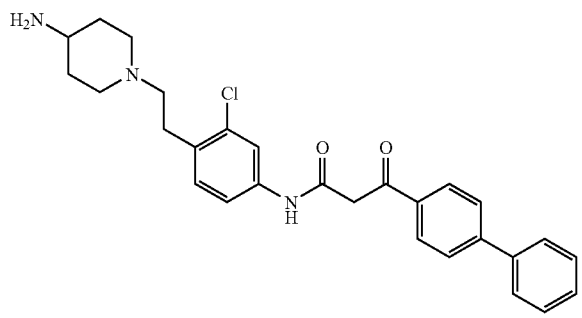

0.19 g (0.33 mmol) of N-{4-[2-(4-tert-butoxycarbonylaminopiperidin-1-yl)ethyl]-3-chlorophenyl}-3-biphenyl-4-yl-3-oxopropionamide (compound 1.41) is dissolved in 7 mL of methylene chloride, 500 mL of trifluoroacetic acid is added, and the mixture is stirred for 12 hours at ambient temperature. After this time, saturated sodium hydrogen carbonate solution is added and the precipitate formed is suction filtered. The residue is dried in vacuo over sodium hydroxide. Yield: 160 mg (100% of theory); $R_f$ value: 0.10 (silica gel, methylene chloride/methanol=9:1); m.p. above 144° C. (decomposition); $C_{28}H_{30}ClN_3O_2$; EII mass spectrum: m/z=476/478 [M+H]$^+$.

Example 10

The following compounds of general formula VIII-1 are prepared analogously to Example 1.0, the educts used being shown in the column headed "Educts":

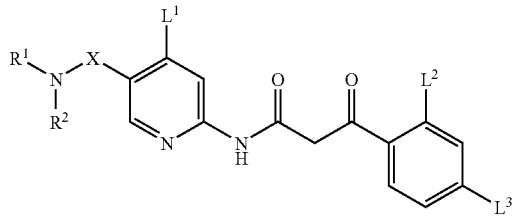

| Ex. # | R$^1$R$^2$NX | L$^1$ | L$^2$ | L$^3$ | Educts | mass spectrum | m.p. [° C.] | R$_f$-value* |
|---|---|---|---|---|---|---|---|---|
| 10.0 | (piperidinylethyl) | —H | —H | (4-substituted phenyl)-H | I.1 VI.9 | 414 [M + H]$^+$ | 178-182 | 0.40 (A) |

The following compounds are prepared analogously to the foregoing Examples:

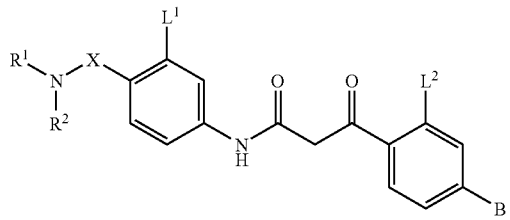

| Example | R$^1$R$^2$NX | L$^1$ | L$^2$ | B |
|---|---|---|---|---|
| 11 | (4-methylpiperidinyl-ethoxy) | —Cl | —H | (phenyl)-H |

-continued

| Example | R¹R²NX | L¹ | L² | B |
|---|---|---|---|---|
| 12 | 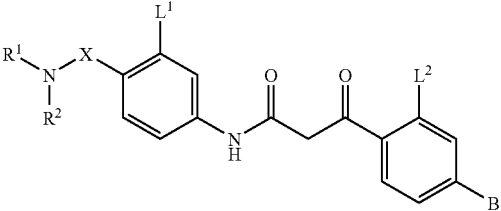 3,5-dimethylpiperidine-N-CH₂CH₂-O- | —Cl | —H | 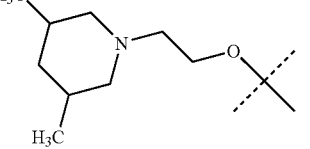 4-tert-butylphenyl |
| 13 | 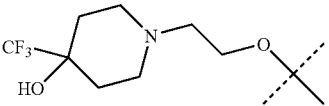 4-CF₃-4-OH-piperidine-N-CH₂CH₂-O- | —Cl | —H | 4-tert-butylphenyl |
| 14 | 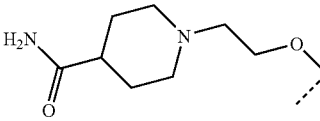 4-carbamoylpiperidine-N-CH₂CH₂-O- | —Cl | —H | 4-tert-butylphenyl |
| 15 | 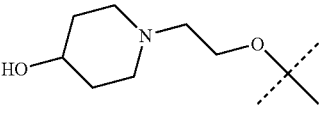 4-hydroxypiperidine-N-CH₂CH₂-O- | —Cl | —H | 4-tert-butylphenyl |
| 16 | 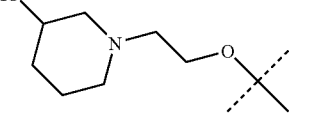 3-hydroxypiperidine-N-CH₂CH₂-O- | —Cl | —H | 4-tert-butylphenyl |
| 17 | 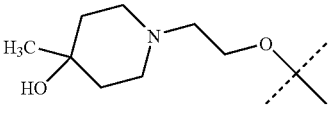 4-methyl-4-hydroxypiperidine-N-CH₂CH₂-O- | —Cl | —H | 4-tert-butylphenyl |
| 18 | 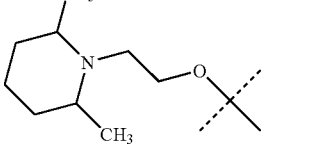 2,6-dimethylpiperidine-N-CH₂CH₂-O- | —Cl | —H | 4-tert-butylphenyl |
| 19 | 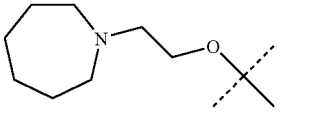 azepane-N-CH₂CH₂-O- | —Cl | —H | 4-tert-butylphenyl |
| 20 | 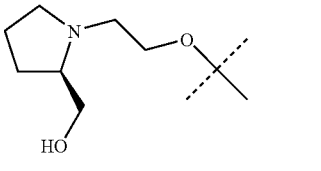 2-(hydroxymethyl)pyrrolidine-N-CH₂CH₂-O- | —Cl | —H | 4-tert-butylphenyl |

-continued

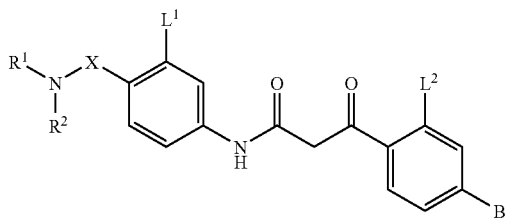

| Example | R¹R²NX | L¹ | L² | B |
|---|---|---|---|---|
| 21 | (S)-2-(hydroxymethyl)pyrrolidin-1-yl ethoxy- | —Cl | —H | 4-H-phenyl |
| 22 | diisopropylamino ethoxy- | —Cl | —H | 4-H-phenyl |
| 23 | N-propyl-N-(cyclopropylmethyl)amino ethoxy- | —Cl | —H | 4-H-phenyl |
| 24 | piperidin-1-yl propyl- | —Cl | —H | 4-H-phenyl |
| 25 | pyrrolidin-1-yl propyl- | —Cl | —H | 4-H-phenyl |
| 26 | 3,5-dimethylpiperidin-1-yl propyl- | —Cl | —H | 4-H-phenyl |
| 27 | 4-carbamoylpiperidin-1-yl propyl- | —Cl | —H | 4-H-phenyl |
| 28 | 4-hydroxypiperidin-1-yl propyl- | —Cl | —H | 4-H-phenyl |

-continued
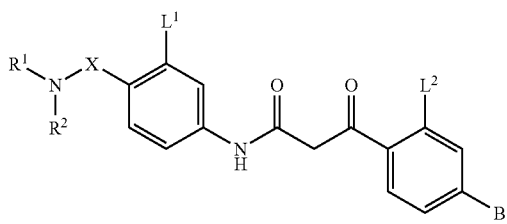
| Example | R¹R²NX | L¹ | L² | B |
|---|---|---|---|---|
| 29 | 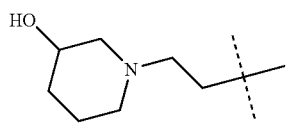 | —Cl | —H | 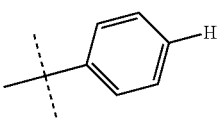 |
| 30 | 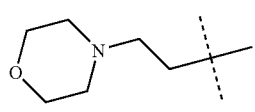 | —Cl | —H | 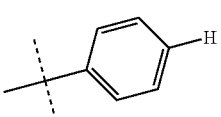 |
| 31 | 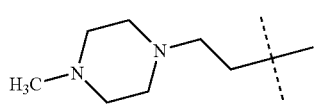 | —Cl | —H | 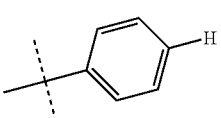 |
| 32 | 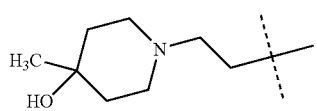 | —Cl | —H | 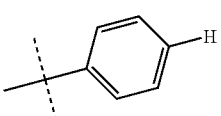 |
| 33 | 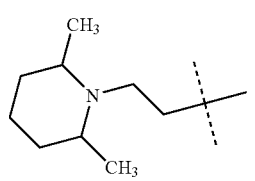 | —Cl | —H | 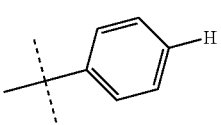 |
| 34 | 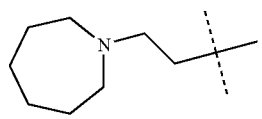 | —Cl | —H | 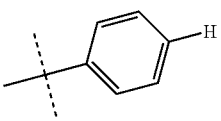 |
| 35 | 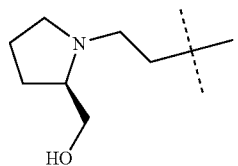 | —Cl | —H | 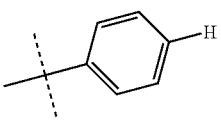 |
| 36 | 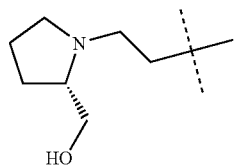 | —Cl | —H | 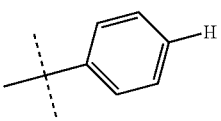 |

-continued
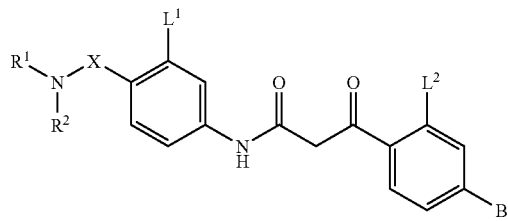
| Example | R¹R²NX | L¹ | L² | B |
|---|---|---|---|---|
| 37 | N(iPr)₂-CH₂CH₂C(CH₃)₂- | —Cl | —H | 4-H-C₆H₄— |
| 38 | N(CH₃)(CH₂-cyclopropyl)-CH₂CH₂C(CH₃)₂- | —Cl | —H | 4-H-C₆H₄— |
| 39 | N(n-Pr)(CH₂-cyclopropyl)-CH₂CH₂C(CH₃)₂- | —Cl | —H | 4-H-C₆H₄— |
| 40 | azetidin-1-yl-CH₂CH₂C(CH₃)₂- | —Cl | —H | 4-H-C₆H₄— |
| 41 | 2,5-dihydropyrrol-1-yl-CH₂CH₂C(CH₃)₂- | —Cl | —H | 4-H-C₆H₄— |
| 42 | N(Et)(iPr)-CH₂CH₂C(CH₃)₂- | —Cl | —H | 4-H-C₆H₄— |
| 43 | N(CH₃)(iPr)-CH₂CH₂C(CH₃)₂- | —Cl | —H | 4-H-C₆H₄— |
| 44 | N(CH₃)(iBu)-CH₂CH₂C(CH₃)₂- | —Cl | —H | 4-H-C₆H₄— |

-continued

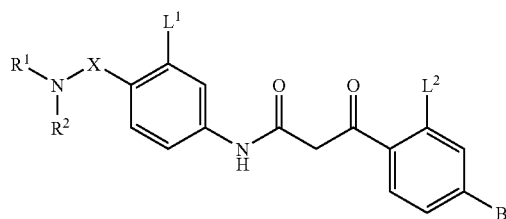

| Example | R¹R²NX | L¹ | L² | B |
|---|---|---|---|---|
| 45 | (N-ethyl, N-isobutyl aminoalkyl) | —Cl | —H | 4-tert-butylphenyl |
| 46 | (1-hydroxycyclopropylmethylamino alkyl) | —Cl | —H | 4-tert-butylphenyl |
| 47 | (piperidin-1-yl alkyl) | —Cl | —Cl | —CF₃ |
| 48 | (pyrrolidin-1-yl alkyl) | —Cl | —Cl | —CF₃ |
| 49 | (4-methylpiperidin-1-yl alkyl) | —Cl | —Cl | —CF₃ |
| 50 | (3,5-dimethylpiperidin-1-yl alkyl) | —Cl | —Cl | —CF₃ |
| 51 | (4-hydroxy-4-trifluoromethylpiperidin-1-yl alkyl) | —Cl | —Cl | —CF₃ |
| 52 | (4-carbamoylpiperidin-1-yl alkyl) | —Cl | —Cl | —CF₃ |
| 53 | (4-hydroxypiperidin-1-yl alkyl) | —Cl | —Cl | —CF₃ |

-continued

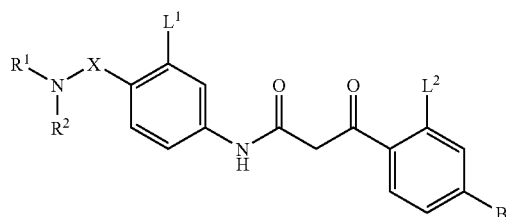

| Example | R¹R²NX | L¹ | L² | B |
|---|---|---|---|---|
| 54 | 3-hydroxypiperidin-1-yl-neopentyl | —Cl | —Cl | —CF₃ |
| 55 | morpholin-4-yl-neopentyl | —Cl | —Cl | —CF₃ |
| 56 | 4-methylpiperazin-1-yl-neopentyl | —Cl | —Cl | —CF₃ |
| 57 | 4-hydroxy-4-methylpiperidin-1-yl-neopentyl | —Cl | —Cl | —CF₃ |
| 58 | 2,6-dimethylpiperidin-1-yl-neopentyl | —Cl | —Cl | —CF₃ |
| 59 | azepan-1-yl-neopentyl | —Cl | —Cl | —CF₃ |
| 60 | (2S)-2-(hydroxymethyl)pyrrolidin-1-yl-neopentyl | —Cl | —Cl | —CF₃ |
| 61 | (2R)-2-(hydroxymethyl)pyrrolidin-1-yl-neopentyl | —Cl | —Cl | —CF₃ |
| 62 | N,N-diisopropylamino-neopentyl | —Cl | —Cl | —CF₃ |

-continued
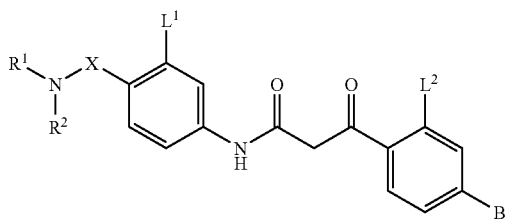
| Example | R¹R²NX | L¹ | L² | B |
|---|---|---|---|---|
| 63 | 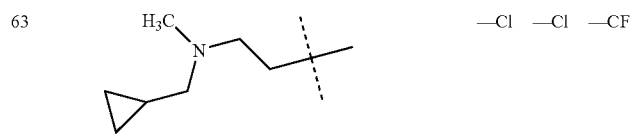 | —Cl | —Cl | —CF₃ |
| 64 | 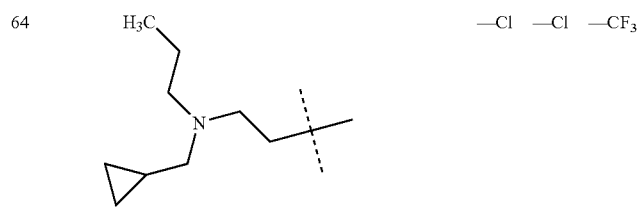 | —Cl | —Cl | —CF₃ |
| 65 |  | —Cl | —Cl | —CF₃ |
| 66 | 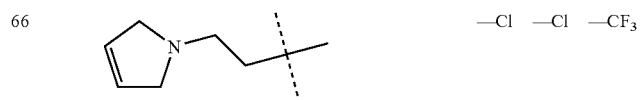 | —Cl | —Cl | —CF₃ |
| 67 | 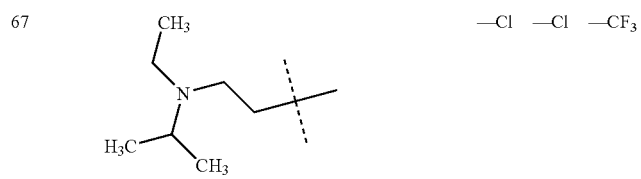 | —Cl | —Cl | —CF₃ |
| 68 | 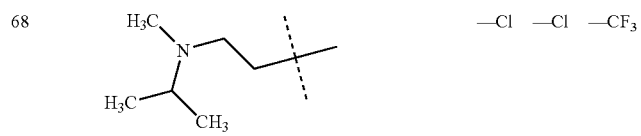 | —Cl | —Cl | —CF₃ |
| 69 | 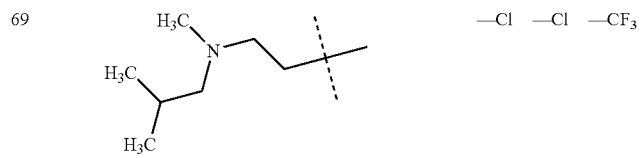 | —Cl | —Cl | —CF₃ |
| 70 | 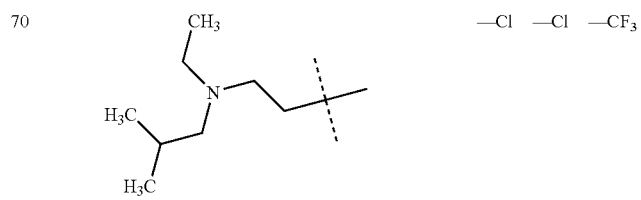 | —Cl | —Cl | —CF₃ |

-continued

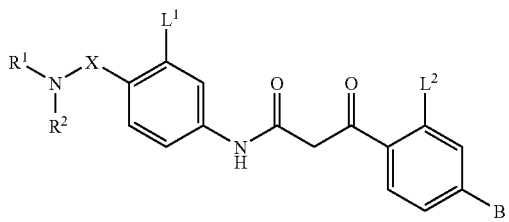

| Example | R¹R²NX | L¹ | L² | B |
|---|---|---|---|---|
| 71 | 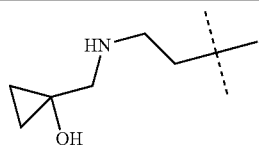 | —Cl | —Cl | —CF₃ |
| 72 | 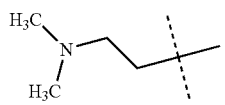 | —Cl | —H | 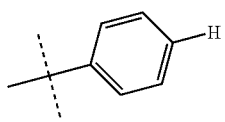 |
| 73 | 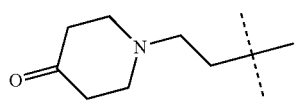 | —Cl | —H | 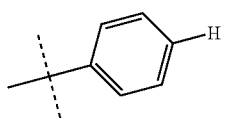 |
| 74 | 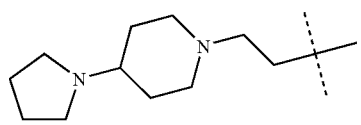 | —Cl | —H | 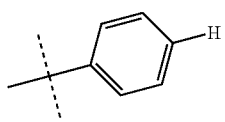 |
| 75 | 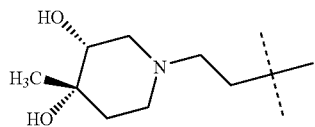 | —Cl | —H | 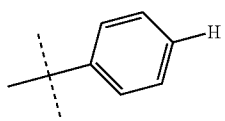 |
| 76 | 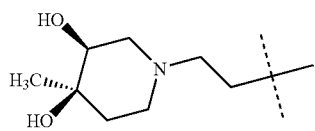 | —Cl | —H | 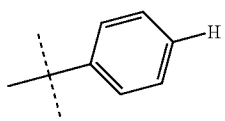 |
| 77 | 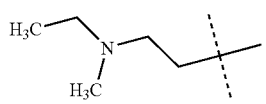 | —Cl | —H | 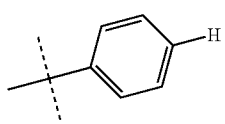 |

Some test methods for determining an MCH-receptor antagonistic activity will now be described. In addition, other test methods known to the skilled man may be used, e.g., by inhibiting the MCH-receptor-mediated inhibition of cAMP production, as described by M. Hoogduijn, et al., Melanin-Concentrating Hormone and its Receptor are Expressed and Functional in Human Skin, Biochem. Biophys. Res Commun. 296 (2002) pp. 698-701, and by biosensory measurement of the binding of MCH to the MCH receptor in the presence of antagonistic substances by plasmon resonance, as described by O. P Karlsson and S. Lofas, Flow-Mediated On-Surface Reconstitution of G-Protein Coupled Receptors for Applications in Surface Plasmon Resonance Biosensors, Anal. Biochem. 300 (2002), 132-138. Other methods of testing antagonistic activity to MCH receptors are contained in the references and patent documents mentioned hereinbefore, and the description of the test methods used is hereby incorporated in this application.

| MCH-1 Receptor Binding Test | |
|---|---|
| Method: | MCH binding to hMCH-1R transfected cells |
| Species: | Human |
| Test cell: | hMCH-1R stably transfected into CHO/Galpha 16 cells |
| Results: | IC₅₀ values |

Membranes from CHO/Galpha16 cells stably transfected with human hMCH-1R are resuspended using a syringe (needle 0.6×25 mm) and diluted in test buffer (50 mM HEPES, 10 mM MgCl$_2$, 2 mM EGTA, pH 7.00; 0.1% bovine serum albumin (protease-free), 0.021% bacitracin, 1 μg/mL aprotinin, 1 μg/mL leupeptin, and 1 μM phosphoramidone) to a concentration of 5 to 15 μg/mL.

200 microliters of this membrane fraction (contains 1 to 3 μg of protein) are incubated for 60 minutes at ambient temperature with 100 pM of $^{125}$I-tyrosyl melanin concentrating hormone ($^{125}$I-MCH commercially obtainable from NEN) and increasing concentrations of the test compound in a final volume of 250 microliters. After the incubation the reaction is filtered using a cell harvester through 0.5% PEI treated fiberglass filters (GF/B, Unifilter Packard). The membrane-bound radioactivity retained on the filter is then determined after the addition of scintillator substance (Packard Microscint 20) in a measuring device (TopCount of Packard).

The non-specific binding is defined as bound radioactivity in the presence of 1 micromolar MCH during the incubation period. The analysis of the concentration binding curve is carried out on the assumption of one receptor binding site.

Standard:

Non-labelled MCH competes with labelled $^{125}$I-MCH for the receptor binding with an IC$_{50}$ value of between 0.06 and 0.15 nM. The KD value of the radioligand is 0.156 nM.

| MCH-1 Receptor-Coupled Ca$^{2+}$ Mobilization Test | |
|---|---|
| Method: | Calcium mobilization test with human MCH (FLIPR$^{384}$) |
| Species: | Human |
| Test cells: | CHO/Galpha 16 cells stably transfected with hMCH-R1 |
| Results: | 1st measurement: % stimulation of the reference (MCH 10$^{-6}$ M) |
|  | 2nd measurement: pKB value |
| Reagents: | HBSS (10×) (GIBCO) |
|  | HEPES buffer (1 M) (GIBCO) |
|  | Pluronic F-127 (Molecular Probes) |
|  | Fluo-4 (Molecular Probes) |
|  | Probenecid (Sigma) |
|  | MCH (Bachem) |
|  | bovine serum albumin (protease-free) (Serva) |
|  | DMSO (Serva) |
|  | Ham's F12 (BioWhittaker) |
|  | FCS (BioWhittaker) |
|  | L-Glutamine (GIBCO) |
|  | Hygromycin B (GIBCO) |
|  | PENStrep (BioWhittaker) |
|  | Zeocin (Invitrogen) |

Clonal CHO/Galpha16 hMCH-R1 cells are cultivated in Ham's F12 cell culture medium (with L-glutamine; BioWhittaker; Cat. No.: BE12-615F). This contains per 500 mL 10% FCS, 1% PENStrep, 5 mL L-glutamine (200 mM stock solution), 3 mL hygromycin B (50 mg/ml in PBS), and 1.25 mL zeocin (100 μg/ml stock solution). One day before the experiment, the cells are plated on a 384-well microtiter plate (black-walled with a transparent base, made by Costar) in a density of 2500 cells per cavity and cultivated in the above medium overnight at 37° C., 5% CO$_2$, and 95% relative humidity. On the day of the experiment the cells are incubated with cell culture medium to which 2 mM Fluo-4 and 4.6 mM Probenicid have been added, at 37° C. for 45 minutes. After charging with fluorescent dye the cells are washed four times with Hanks buffer solution (1×HBSS, 20 mM HEPES), which has been combined with 0.07% Probenicid. The test substances are diluted in Hanks buffer solution, combined with 2.5% DMSO. The background fluorescence of non-stimulated cells is measured in the presence of substance in the 384-well microtiter plate five minutes after the last washing step in the FLIPR$^{384}$ apparatus (Molecular Devices; excitation wavelength: 488 nm; emission wavelength: bandpass 510 to 570 nm). To stimulate the cells, MCH is diluted in Hanks buffer with 0.1% BSA, pipetted into the 384-well cell culture plate 35 minutes after the last washing step and the MCH-stimulated fluorescence is then measured in the FLIPR$^{384}$ apparatus.

Data Analysis:

1st measurement: The cellular Ca$^{2+}$ mobilization is measured as the peak of the relative fluorescence minus the background and is expressed as the percentage of the maximum signal of the reference (MCH 10$^{-6}$M). This measurement serves to identify any possible agonistic effect of a test substance.

2nd measurement: The cellular Ca$^{2+}$ mobilization is measured as the peak of the relative fluorescence minus the background and is expressed as the percentage of the maximum signal of the reference (MCH 10$^{-6}$M, signal is standardized to 100%). The EC50 values of the MCH dosage activity curve with and without test substance (defined concentration) are determined graphically by the GraphPad Prism 2.01 curve program. MCH antagonists cause the MCH stimulation curve to shift to the right in the graph plotted.

The inhibition is expressed as a pKB value:

$$pKB = \log(EC_{50(testsubstance+MCH)}/EC_{50(MCH)}-1) - \log c_{(testsubstance)}$$

The compounds according to the invention, including their salts, exhibit an MCH-receptor antagonistic activity in the tests mentioned above. Using the MCH-1 receptor binding test described above an antagonistic activity is obtained in a dosage range from about 10$^{-10}$ to 10$^{-5}$ M, particularly from 10$^{-9}$ to 10$^{-6}$ M.

The following IC$_{50}$ values were determined using the MCH-1 receptor binding test described above:

| Compound according to Example No. | Structure | IC$_{50}$ value |
|---|---|---|
| 5.1 | 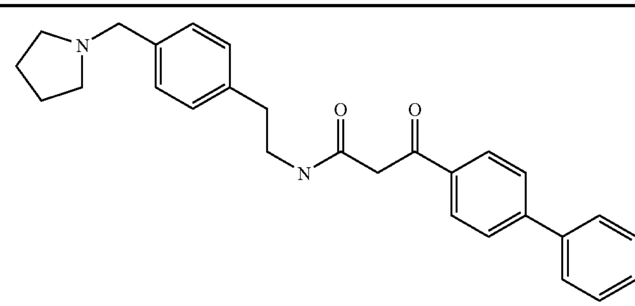 | 63.7 nM |

-continued

| Compound according to Example No. | Structure | IC$_{50}$ value |
|---|---|---|
| 7.1 | (H$_3$C-CH$_2$)$_2$N-CH$_2$CH$_2$-O-C$_6$H$_3$(Cl)-NH-C(O)-CH$_2$-C(O)-C$_6$H$_3$(Cl)(CF$_3$) | 34.8 nM |

Some examples of formulations will be described hereinafter, wherein the term "active substance" denotes one or more compounds according to the invention, including their salts. In the case of one of the combinations with one or more active substances described, the term "active substance" also includes the additional active substances.

Example A

Capsules for Powder Inhalation Containing 1 mg Active Substance

Composition:
1 capsule for powder inhalation contains:

| | |
|---|---|
| active substance | 1.0 mg |
| lactose | 20.0 mg |
| hard gelatin capsules | 50.0 mg |
| | 71.0 mg |

Method of Preparation:
The active substance is ground to the particle size required for inhalation. The ground active substance is homogeneously mixed with the lactose. The mixture is packed into hard gelatin capsules.

Example B

Inhalable Solution for RESPIMAT® Containing 1 mg Active Substance

Composition:
1 spray contains:

| | |
|---|---|
| active substance | 1.0 mg |
| benzalkonium chloride | 0.002 mg |
| disodium edetate | 0.0075 mg |
| purified water | to 15.0 µL |

Method of Preparation:
The active substance and benzalkonium chloride are dissolved in water and packed into RESPIMAT® cartridges.

Example C

Inhalable Solution for Nebulizer Containing 1 mg Active Substance

Composition:
1 vial contains:

| | |
|---|---|
| active substance | 0.1 g |
| sodium chloride | 0.18 g |
| benzalkonium chloride | 0.002 g |
| purified water | to 20.0 mL |

Method of Preparation:
The active substance, sodium chloride, and benzalkonium chloride are dissolved in water.

Example D

Propellant Type Metered Dose Aerosol Containing 1 mg Active Substance

Composition:
1 spray contains:

| | |
|---|---|
| active substance | 1.0 mg |
| lecithin | 0.1% |
| propellant gas | to 50.0 µL |

Method of Preparation:
The micronized active substance is homogeneously suspended in the mixture of lecithin and propellant gas. The suspension is transferred into a pressurised container with a metering valve.

Example E

Nasal Spray Containing 1 mg Active Substance

Composition:

| | |
|---|---|
| active substance | 1.0 mg |
| sodium chloride | 0.9 mg |
| benzalkonium chloride | 0.025 mg |
| disodium edetate | 0.05 mg |
| purified water | to 0.1 mL |

Method of Preparation:

The active substance and the excipients are dissolved in water and transferred into a corresponding container.

Example F

Injectable Solution Containing 5 mg of Active Substance Per 5 mL

Composition:

| | |
|---|---|
| active substance | 5 mg |
| glucose | 250 mg |
| human serum albumin | 10 mg |
| glycofurol | 250 mg |
| water for injections | to 5 mL |

Method of Preparation:

Glycofurol and glucose are dissolved in water for injections (WfI) and human serum albumin is added. The active ingredient is dissolved with heating, made up to specified volume with WfI, and transferred into ampoules under nitrogen gas.

Example G

Injectable Solution Containing 100 mg of Active Substance Per 20 mL

Composition:

| | |
|---|---|
| active substance | 100 mg |
| monopotassium dihydrogen phosphate ($KH_2PO_4$) | 12 mg |
| disodium hydrogen phosphate ($Na_2HPO_4 \cdot 2H_2O$) | 2 mg |
| sodium chloride | 180 mg |
| human serum albumin | 50 mg |
| Polysorbate 80 | 20 mg |
| water for injections | to 20 mL |

Method of Preparation:

Polysorbate 80, sodium chloride, monopotassium dihydrogen phosphate, and disodium hydrogen phosphate are dissolved in water for injections (WfI) and human serum albumin is added. The active ingredient is dissolved with heating, made up to specified volume with WfI, and transferred into ampoules.

Example H

Lyophilisate Containing 10 mg of Active Substance

Composition:

| | |
|---|---|
| Active substance | 10 mg |
| Mannitol | 300 mg |
| human serum albumin | 20 mg |

Method of Preparation:

Mannitol is dissolved in water for injections (WfI) and human serum albumin is added. The active ingredient is dissolved with heating, made up to specified volume with WfI, transferred into vials, and freeze-dried.

Solvent for Lyophilisate:

| | |
|---|---|
| Polysorbate 80 = Tween 80 | 20 mg |
| mannitol | 200 mg |
| water for injections | to 10 mL |

Method of Preparation:

Polysorbate 80 and mannitol are dissolved in water for injections (WfI) and transferred into ampoules.

Example I

Tablets Containing 20 mg of Active Substance

Composition:

| | |
|---|---|
| active substance | 20 mg |
| lactose | 120 mg |
| maize starch | 40 mg |
| magnesium stearate | 2 mg |
| Povidone K 25 | 18 mg |

Method of Preparation:

Active substance, lactose, and maize starch are homogeneously mixed, granulated with an aqueous solution of Povidone, mixed with magnesium stearate, and compressed in a tablet press (weight of tablet: 200 mg).

Example J

Capsules Containing 20 mg Active Substance

Composition:

| | |
|---|---|
| active substance | 20 mg |
| maize starch | 80 mg |
| highly dispersed silica | 5 mg |
| magnesium stearate | 2.5 mg |

Method of Preparation:

Active substance, maize starch, and silica are homogeneously mixed, mixed with magnesium stearate, and the mixture is packed into size 3 hard gelatin capsules in a capsule filling machine.

Example K

Suppositories Containing 50 mg of Active Substance

Composition:

| | |
|---|---|
| active substance | 50 mg |
| hard fat (Adeps solidus) q.s. | to 1700 mg |

Method of Preparation:

Hard fat is melted at about 38° C. and ground active substance is homogeneously dispersed in the molten hard fat; after cooling to about 35° C. it is poured into chilled moulds.

Example L

Injectable Solution Containing 10 mg of Active Substance Per 1 mL

Composition:

| | |
|---|---|
| active substance | 10 mg |
| mannitol | 50 mg |
| human serum albumin | 10 mg |
| water for injections | to 1 mL |

Method of Preparation:

Mannitol is dissolved in water for injections (WfI) and human serum albumin is added. The active ingredient is dissolved with heating, made up to specified volume with WfI, and transferred into ampoules under nitrogen gas.

We claim:

1. A compound of formula I

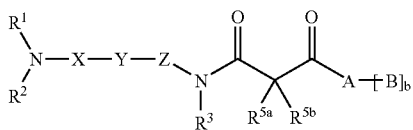

wherein:

$R^1$ and $R^2$ form an alkylene bridge, such that $R^1R^2N$— denotes pyrrolidine, wherein in the alkylene bridge one or more H atoms are optionally replaced by $R^{14}$, and the alkylene bridge is optionally independently substituted by one or two Cy groups such that the bond between the alkylene bridge and the Cy group is made via a single or double bond;

$R^3$ is H, $C_{1-6}$-alkyl, $C_{3-7}$-cycloalkyl, $C_{3-7}$-cycloalkyl-$C_{1-4}$-alkyl, or phenyl-$C_{1-3}$-alkyl;

X is a $C_{1-8}$-alkylene bridge, wherein a —$CH_2$— group which is not directly linked to the group $R^1R^2N$— is optionally replaced by —CH=CH— or —C≡C— wherein two C atoms of the bridge X are optionally joined together by an additional $C_{1-4}$-alkylene bridge, and a C atom not directly connected to a heteroatom is optionally substituted by $R^{10}$ and/or one or two C atoms are optionally independently substituted by one or two identical or different substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl, and $C_{4-7}$-cycloalkenyl-$C_{1-3}$-alkyl, wherein two alkyl and/or alkenyl substituents are optionally joined together, forming a carbocyclic ring system;

Z is a single bond or —$CR^{7a}R^{7b}$—$CR^{7c}R^{7d}$—;

Y denotes indolyl, which may be mono- or polysubstituted at one or more C atoms by $R^{20}$, and A denotes phenyl, which may be mono- or polysubstituted by $R^{20}$ and may also additionally be monosubstituted by nitro; and B denotes phenyl, which may be mono- or polysubstituted by $R^{20}$ and may also additionally be monosubstituted by nitro; and b has the value 0 or 1, Cy is a saturated 3- to 7-membered carbocyclic group, an unsaturated 4- to 7-membered carbocyclic group, a phenyl group, a saturated 4- to 7-membered or unsaturated 5- to 7-membered heterocyclic group with an N, O, or S atom as heteroatom, a saturated or unsaturated 5- to 7-membered heterocyclic group with two or more N atoms or with one or two N atoms and one O or S atom as heteroatoms, an aromatic heterocyclic 5- or 6-membered group with one or more identical or different heteroatoms selected from N, O, and/or S, wherein the 4-, 5-, 6-, or 7-membered groups of Cy are optionally fused to a phenyl or pyridine ring via two common adjacent C atoms, and in the 5-, 6-, or 7-membered groups of Cy one or two non-adjacent —$CH_2$ groups are optionally independently replaced by a —CO—, —C(=$CH_2$)—, —(SO)—, or —($SO_2$)— group, and the saturated 6- or 7-membered groups of Cy are optionally bridged ring systems with an imino, N—($C_{1-4}$-alkyl)-imino, methylene, $C_{1-4}$-alkyl-methylene, or di-($C_{1-4}$-alkyl)-methylene bridge, and the cyclic groups of Cy are optionally mono- or polysubstituted by $R^{20}$ at one or more C atoms, and in the case of a phenyl group are optionally additionally monosubstituted by nitro, and/or one or more NH groups is optionally substituted by $R^{21}$, $R^4$ has one of the meanings given for $R^{17}$ or denotes $C_{3-6}$-alkenyl, or $C_{3-6}$-alkynyl;

$R^{5a}$ and $R^{5b}$ are each independently H, $C_{1-3}$-alkyl, $C_{3-7}$-cycloalkyl, $C_{3-7}$-cycloalkyl-$C_{1-3}$-alkyl, $CF_3$, F, or Cl, wherein if $R^{5a}$ and $R^{5b}$ are each an alkyl, they are optionally joined together such that a $C_{3-7}$-cycloalkyl group is formed together with the C atom to which $R^{5a}$ and $R^{5b}$ are linked;

$R^{7a}$ and $R^{7c}$ are each independently H, F, Cl, $C_{1-4}$-alkyl, or $CF_3$;

$R^{7b}$ and $R^{7d}$ are each independently H, F, $C_{1-4}$-alkyl, $C_{3-7}$-cycloalkyl, $C_{3-7}$-cycloalkyl-$C_{1-3}$-alkyl, or $CF_3$, wherein if $R^{7a}$ and $R^{7b}$ are each alkyl, they are optionally joined together such that a $C_{3-7}$-cycloalkyl group is formed together with the C atom to which $R^{7a}$ and $R^{7b}$ are linked, and/or if $R^{7c}$ and $R^{7d}$ are each alkyl, they are optionally joined together such that a $C_{3-7}$-cycloalkyl group is formed together with the C atom to which $R^{7c}$ and $R^{7d}$ are linked, or $R^{7b}$ and $R^{7d}$ are each alkyl, they are optionally joined together such that a $C_{3-7}$-cycloalkyl group is formed together with the two C atoms to which $R^{7b}$ and $R^{7d}$ are linked;

$R^{10}$ is hydroxy, hydroxy-$C_{1-3}$-alkyl, $C_{1-4}$-alkoxy, ($C_{1-4}$-alkoxy)-$C_{1-3}$-alkyl, carboxy, $C_{1-4}$-alkoxycarbonyl, amino, $C_{1-4}$-alkyl-amino, di-($C_{1-4}$-alkyl)-amino, cyclo-$C_{3-6}$-alkyleneimino, amino-$C_{1-3}$-alkyl, $C_{1-4}$-alkyl-amino-$C_{1-3}$-alkyl, di-($C_{1-4}$-alkyl)-amino-$C_{1-3}$-alkyl, cyclo-$C_{3-6}$-alkyleneimino-$C_{1-3}$-alkyl, amino-$C_{1-3}$-alkoxy, $C_{1-4}$-alkyl-amino-$C_{1-3}$-alkoxy, di-($C_{1-4}$-alkyl)-amino-$C_{1-3}$-alkoxy, cyclo-$C_{3-6}$-alkyleneimino-$C_{1-3}$-alkoxy, aminocarbonyl, $C_{1-4}$-alkyl-aminocarbonyl, di-($C_{1-4}$-alkyl)-aminocarbonyl, or cyclo-$C_{3-6}$-alkyleneimino-carbonyl;

$R^{11}$ is $C_{1-3}$-alkyl, $C_{2-6}$-alkenyl, $C_{2-6}$-alkynyl, $R^{15}$—O—, $R^{15}$—O—$C_{1-3}$-alkyl-, $R^{15}$—O—CO—, $R^{15}$—CO—O, cyano, $R^{16}R^{17}N$—, $R^{18}R^{19}N$—CO—, or Cy;

$R^{13}$ has one of the meanings given for $R^{17}$;

$R^{14}$ is halogen, $C_{1-6}$-alkyl, $C_{2-6}$-alkenyl, $C_{2-6}$-alkynyl, $R^{15}$—O—, $R^{15}$—O—CO—, $R^{15}$—CO, $R^{15}$—CO—O—, $R^{16}R^{17}N$—, $R^{18}R^{19}N$—CO—$R^{15}$—O—$C_{1-3}$-alkyl, $R^{15}$—O—CO—$C_{1-3}$-alkyl, $R^{15}$—O—CO—

NH—, $R^{15}$—$SO_2$—NH—, $R^{15}$—O—CO—NH—$C_{1-3}$-alkyl, $R^{15}$—$SO_2$—NH—$C_{1-3}$-alkyl, $R^{15}$—CO—$C_{1-3}$-alkyl, $R^{15}$—CO—O—$C_{1-3}$-alkyl, $R^{16}R^{17}N$—$C_{1-3}$-alkyl, $R^{18}R^{19}N$—CO—$C_{1-3}$-alkyl, or Cy—$C_{1-3}$-alkyl-;

$R^{15}$ is H, $C_{1-4}$-alkyl, $C_{3-7}$-cycloalkyl, $C_{3-7}$-cycloalkyl-$C_{1-3}$-alkyl, phenyl, phenyl-$C_{1-3}$-alkyl, pyridinyl, or pyridinyl-$C_{1-3}$-alkyl;

$R^{16}$ is H, $C_{1-6}$-alkyl, $C_{3-7}$-cycloalkyl, $C_{3-7}$-cycloalkyl-$C_{1-3}$-alkyl, $C_{4-7}$-cycloalkenyl, $C_{4-7}$-cycloalkenyl-$C_{1-3}$-alkyl, hydroxy-$C_{2-3}$-alkyl, $C_{1-4}$-alkoxy-$C_{2-3}$-alkyl, amino-$C_{2-6}$-alkyl, $C_{1-4}$-alkyl-amino-$C_{2-6}$-alkyl, di-($C_{1-4}$-alkyl)-amino-$C_{2-6}$-alkyl, or cyclo-$C_{3-6}$-alkyleneimino-$C_{2-6}$-alkyl;

$R^{17}$ has one of the meanings given for $R^{16}$ or denotes phenyl, phenyl-$C_{1-3}$-alkyl, pyridinyl, dioxolan-2-yl, $C_{1-4}$-alkylcarbonyl, hydroxy-carbonyl-$C_{1-3}$-alkyl, $C_{1-4}$-alkoxycarbonyl, $C_{1-4}$-alkoxycarbonyl-$C_{1-3}$-alkyl, $C_{1-4}$-alkylcarbonylamino-$C_{2-3}$-alkyl, N—($C_{1-4}$-alkylcarbonyl)-N—($C_{1-4}$-alkyl)-amino-$C_{2-3}$-alkyl, $C_{1-4}$-alkylsulfonyl, $C_{1-4}$-alkylsulfonylamino-$C_{2-3}$-alkyl, or N—($C_{1-4}$-alkylsulfonyl)-N—($C_{1-4}$-alkyl)-amino-$C_{2-3}$-alkyl-;

$R^{18}$ and $R^{19}$ are each independently H or $C_{1-6}$-alkyl;

$R^{20}$ is halogen, hydroxy, cyano, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, hydroxy-$C_{1-4}$-alkyl, $R^{22}$—$C_{1-3}$-alkyl, or has one of the meanings given for $R^{22}$;

$R^{21}$ is $C_{1-4}$-alkyl, hydroxy-$C_{2-3}$-alkyl, $C_{1-4}$-alkoxy-$C_{2-6}$-alkyl, $C_{1-4}$-alkyl-amino-$C_{2-6}$-alkyl, di-($C_{1-4}$-alkyl)-amino-$C_{2-6}$-alkyl, cyclo-$C_{3-6}$-alkyleneimino-$C_{2-6}$-alkyl, phenyl-$C_{1-3}$-alkyl, $C_{1-4}$-alkyl-carbonyl, $C_{1-4}$-alkoxy-carbonyl, or $C_{1-4}$-alkylsulfonyl;

$R^{22}$ is phenyl-$C_{1-3}$-alkoxy, cyclo-$C_{3-6}$-alkyleneimino-$C_{2-4}$-alkoxy, $C_{1-4}$-alkoxy, $C_{1-4}$-alkylthio, carboxy, $C_{1-4}$-alkylcarbonyl, $C_{1-4}$-alkoxycarbonyl, aminocarbonyl, $C_{1-4}$-alkylamino-carbonyl, di-($C_{1-4}$-alkyl)-aminocarbonyl, cyclo-$C_{3-6}$-alkyl-amino-carbonyl, cyclo-$C_{3-6}$-alkyleneimino-carbonyl, cyclo-$C_{3-6}$-alkyleneimino-$C_{2-4}$-alkyl-aminocarbonyl, phenyl-amino-carbonyl, $C_{1-4}$-alkyl-sulfonyl, $C_{1-4}$-alkyl-sulfinyl, $C_{1-4}$-alkyl-sulfonylamino, amino, $C_{1-4}$-alkylamino, di-($C_{1-4}$-alkyl)-amino, $C_{1-4}$-alkyl-carbonyl-amino, cyclo-$C_{3-6}$-alkyleneimino, phenyl-$C_{1-3}$-alkylamino, N—($C_{1-4}$-alkyl)-phenyl-$C_{1-3}$-alkylamino, acetylamino, propionylamino, phenylcarbonylamino, phenylcarbonylmethylamino, hydroxy-$C_{1-3}$-alkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, aminocarbonylamino, or $C_{1-4}$-alkylaminocarbonylamino, wherein in each of the abovementioned groups and radicals one or more C atoms are optionally additionally mono- or polysubstituted by F and/or in each case one or two C atoms are optionally independently additionally monosubstituted by Cl or Br and/or one or more phenyl rings optionally independently additionally comprise one, two, or three substituents selected from the group F, Cl, Br, I, $C_{1-4}$-alkyl, $C_{1-4}$-alkoxy, difluoromethyl, trifluoromethyl, hydroxy, amino, $C_{1-3}$-alkylamino, di-($C_{1-3}$-alkyl)-amino, acetylamino, aminocarbonyl, cyano, difluoromethoxy, trifluoromethoxy, amino-$C_{1-3}$-alkyl, $C_{1-3}$-alkylamino-$C_{1-3}$-alkyl, and di-($C_{1-3}$-alkyl)-amino-$C_{1-3}$-alkyl and/or are optionally monosubstituted by nitro, and the H atom of a carboxy group or an H atom bound to an N atom are each optionally replaced by a group which can be cleaved in vivo, or a tautomer, enantiomer, salt, or mixture thereof.

2. The compound according to claim 1, wherein $R^1R^2N$— denotes a pyrrolidine ring wherein one or more H atoms may be replaced by $R^{14}$ and/or an H atom may be replaced by Cy representing $C_{3-6}$-cycloalkyl, which may be mono- or polysubstituted by $R^{20}$.

3. The compound according to claim 2, wherein $R^{20}$ is selected from F, hydroxy, $C_{1-3}$-alkyl, $CF_3$, $C_{1-3}$-alkyloxy, $OCF_3$, or hydroxy-$C_{1-3}$-alkyl.

4. The compound according to claim 2, wherein $R^{14}$ in each case independently of one another denotes F, Cl, $C_{1-4}$-alkyl, $C_{3-6}$-cycloalkyl-$C_{1-3}$-alkyl, hydroxy, hydroxy-$C_{1-3}$-alkyl, $C_{1-4}$-alkyloxy, $C_{1-4}$-alkoxy-$C_{1-3}$-alkyl, pyridylamino, or aminocarbonyl, while in each case one or more C atoms are optionally additionally mono- or polysubstituted by F.

5. The compound according to claim 1, wherein X is an unbranched $C_{1-4}$-alkylene bridge and, if Y is linked to X via a C atom, is also —$CH_2$—CH=CH—, —$CH_2$—C≡C—, wherein in X a C atom is optionally substituted by $R^{10}$ and/or one or two C atoms are optionally independently substituted by one or two substituents selected from $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{4-7}$-cycloalkenyl and $C_{4-7}$-cycloalkenyl-$C_{1-3}$-alkyl, while two alkyl and/or alkenyl substituents are optionally joined together, forming a carbocyclic ring system, and wherein in the abovementioned groups and radicals one or more C atoms are optionally mono- or polysubstituted by F and/or one or two C atoms are optionally independently monosubstituted by Cl or Br.

6. The compound according to claim 5, wherein X is —$CH_2$—, —$CH_2$—$CH_2$—, —$CH_2$—$CH_2$—$CH_2$—, or —$CH_2$—CH=CH—$CH_2$— and, if Y is linked to X via a C atom, X is also —$CH_2$—CH=CH— or —$CH_2$—C≡C— wherein one or two C atoms are optionally independently substituted by one or two $C_{1-4}$-alkyl groups, wherein two alkyl groups are optionally joined together, forming a carbocyclic ring system, and one or more C atoms are optionally mono- or polysubstituted by F and/or one or two C atoms are optionally independently monosubstituted by Cl or Br.

7. The compound according to claim 2, wherein $R^{14}$ in each case independently of one another denotes F, Cl, $C_{1-4}$-alkyl, $C_{3-6}$-cycloalkyl-$C_{1-3}$-alkyl, hydroxy, hydroxy-$C_{1-3}$-alkyl, $C_{1-4}$-alkyloxy, $C_{1-4}$-alkoxy-$C_{1-3}$-alkyl, pyridylamino, or aminocarbonyl, while in each case one or more C atoms of the alkyl groups are optionally additionally mono- or polysubstituted by F.

8. The compound according to claim 1, wherein Y is

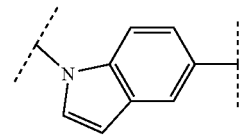

which is optionally mono- or polysubstituted at one or more C atoms by $R^{20}$.

9. The compound according to claim 1, wherein b is 0.

10. The compound according to claim 1, wherein b is 1.

11. The compound according claim 1, wherein Z is a single bond or —$CH_2$—$CH_2$—.

12. The compound according to claim 1, wherein $R^3$ is H or methyl.

13. The compound according to claim 1, wherein:

$R^{20}$ is halogen, hydroxy, cyano, $C_{1-4}$-alkyl, $C_{2-4}$-alkenyl, $C_{2-4}$-alkynyl, $C_{3-7}$-cycloalkyl, $C_{3-7}$-cycloalkyl-$C_{1-3}$- alkyl, hydroxy-$C_{1-4}$-alkyl, and $R^{22}$—$C_{1-3}$-alkyl, or has one of the meanings given for $R^{22}$, and $R^{22}$ is $C_{1-4}$-alkoxy, $C_{1-4}$-alkylthio, carboxy, $C_{1-4}$-alkylcarbonyl, $C_{1-4}$-alkoxycarbonyl, aminocarbonyl, $C_{1-4}$-alkylaminocarbonyl, di-($C_{1-4}$-alkyl)-aminocarbonyl, $C_{1-4}$-alkyl-sulfonyl, $C_{1-4}$-alkyl-sulfinyl, $C_{1-4}$-alkyl-sulfonylamino, amino, $C_{1-4}$-alkylamino-, di-($C_{1-4}$-alkyl)-amino, $C_{1-4}$-alkyl-carbonylamino, hydroxy-$C_{1-3}$-alkylaminocarbonyl, aminocarbonylamino, or $C_{1-4}$-alkylaminocarbonylamino, wherein in each of $R^{20}$ and $R^{22}$ one or more C atoms are optionally mono- or polysubstituted by F and/or one or two C atoms are optionally independently additionally monosubstituted by Cl or Br.

14. A physiologically acceptable salt of the compound according to one of claims 1-8, 9-12 or 13.

15. A pharmaceutical composition comprising the compound according to one of claims 1-8, 9-12 or 13 and one or more physiologically acceptable excipients, inert carriers, or diluents.

16. A method of reducing the body weight of a mammal comprising administering to the mammal an effective amount of the compound according to claim 1.

17. A method of treating eating disorders in a patient, comprising administering to the patient an effective amount of the compound according to claim 1, wherein the eating disorder is obesity.

18. A compound selected from the group consisting of:

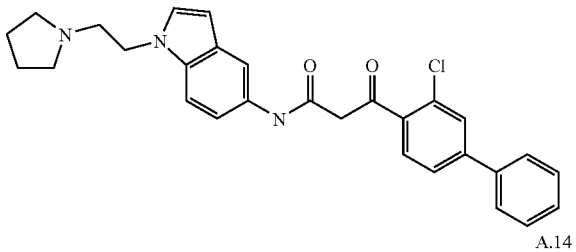

A.13

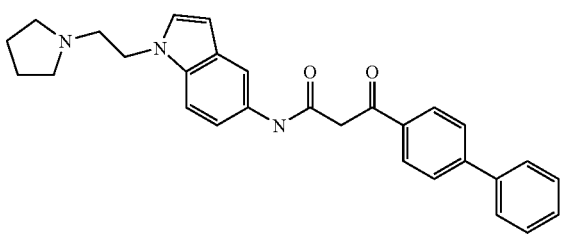

A.14 or a tautomer, enantiomer, salt, or mixture thereof.

* * * * *